(12) United States Patent
Zenkoh et al.

(10) Patent No.: US 8,030,489 B2
(45) Date of Patent: Oct. 4, 2011

(54) ORNITHINE DERIVATIVE

(75) Inventors: Tatsuya Zenkoh, Tokyo (JP); Eisuke Nozawa, Tokyo (JP); Keisuke Matsuura, Tokyo (JP); Ryushi Seo, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 12/531,713

(22) PCT Filed: Mar. 25, 2008

(86) PCT No.: PCT/JP2008/055474
§ 371 (c)(1),
(2), (4) Date: Sep. 17, 2009

(87) PCT Pub. No.: WO2008/123207
PCT Pub. Date: Oct. 16, 2008

(65) Prior Publication Data
US 2010/0216803 A1    Aug. 26, 2010

(30) Foreign Application Priority Data
Mar. 26, 2007   (JP) .................................. 2007-078315

(51) Int. Cl.
*A61P 13/12*   (2006.01)

(52) U.S. Cl. ........ 544/355; 544/393; 546/121; 546/156; 546/169; 546/175; 548/374.1; 548/491; 548/537; 514/249; 514/255.03; 514/300; 514/311; 514/312; 514/423

(58) Field of Classification Search .................. None
See application file for complete search history.

(56) References Cited

FOREIGN PATENT DOCUMENTS
WO    2005 061475    7/2005

OTHER PUBLICATIONS

Dr. Florencio Zaragoza Dörwald, Side Reactions in Organic Synthesis, WILEY, p. IX, 1-15 (Jul. 25, 2005).*
Martin et. al., Do Structurally Similar Molecules Have Similar Biological Activity?, 45(19) J. Med. Chem. 4350-4358 (2002).*
Regan, EP2 and EP4 Prostanoid Receptor Signaling, 74 Life Sciences 143-153 (2003).*

* cited by examiner

*Primary Examiner* — Janet Andres
*Assistant Examiner* — Timothy R Rozof
(74) *Attorney, Agent, or Firm* — Oblon, Spivak, McClelland, Maier & Neustadt, L.L.P.

(57) ABSTRACT

Provided is a compound which is useful as a therapeutic agent for chronic renal insufficiency and a therapeutic agent for diabetic nephropathy.

The present inventors have made extensive studies on an ornithine derivative having an antagonistic action against an EP4 receptor, and as a result, they have found that by introducing cycloalkanediyl at a C terminal of the ornithine part of the compound of the present invention, the physicochemical properties such as solubility, and the like can be improved, thereby giving further preferred properties as a pharmaceutical. Therefore, they have completed the present invention.

The compound of the present invention exhibits a good antagonistic action against an EP4 receptor, and thus, it is useful as a therapeutic agent for chronic renal insufficiency and diabetic nephropathy.

5 Claims, No Drawings

ORNITHINE DERIVATIVE

CROSS-REFERENCE TO RELATED APPLICATIONS

The present application is a 35 U.S.C. §371 National Stage patent application of International patent application PCT/JP2008/055474, filed on Mar. 25, 2008, which claims priority to Japanese patent application JP 2007-078315, filed on Mar. 26, 2007.

TECHNICAL FIELD

The present invention relates to a pharmaceutical, and particularly a compound useful as a therapeutic agent for chronic renal insufficiency and diabetic nephropathy.

BACKGROUND ART

PGE2 is known as one of the metabolites in an arachidonic acid cascade. The PGE2 exhibits various activities such as a pain inducing and increasing action, a pro- or anti-inflammatory action, an uterine contractile action, a digestive peristalsis promoting action, an awaking action, a suppressive effect on gastric acid secretion, a hypotensive action, a platelet aggregation inhibition action, a bone-resorption promoting action, an angiogenic action, and the like.

PGE2 receptors are divided into four subtypes, EP1, EP2, EP3 and EP4, which have a wide distribution in various tissues. The activation of the EP 1 receptor is believed to increase intracellular $Ca^{2+}$. The EP3 receptor is one of the receptors having different routes for second-messenger systems. Further, the activation of the EP2 and EP4 receptors is believed to cause the activation of an adenylate cyclase, and thus increase the intracellular cAMP level. Especially, the EP4 receptor is considered to be associated with smooth muscle relaxation, pro- or anti-inflammatory reactions, lymphocyte differentiation, mesangial cell relaxation or proliferation, gastric or enteric mucus secretion, or the like.

The inhibitors of the PGE2 receptor, that is, the "PGE2 antagonists", exhibit binding activities to the PGE2 receptors. That is, the PGE2 antagonists exhibit a PGE2-antagonistic or PGE2-inhibiting action. Therefore, the PGE2 antagonists are expected as pharmaceuticals to treat PGE2-mediated diseases. It is expected that these PGE2 antagonists can be used as therapeutic drugs to treat EP4 receptors-related diseases, such as renal diseases, inflammatory diseases, various pains, or the like, by acting on the EP4 receptors, in humans or animals.

As a compound having a PGE2 antagonistic action, there has been reported a compound represented by the following formula, and particularly, such a compound is useful as an EP4 receptor agonist (Patent Document 1).

[Chem. 1]

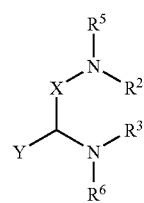

(wherein particularly X represents —CO— or lower alkylene, $R^5$ represents H or lower alkyl, and $R^2$ represents lower alkyl or aryl which may be substituted. Refer to the following publication for the details.)

[Patent Document 1] Pamphlet of International Publication No. WO 2005/061475

DISCLOSURE OF THE INVENTION

Problem that the Invention is to Solve

It is an object of the present invention to provide a novel pharmaceutical having a selective antagonistic action to an EP4 receptor, and particularly a novel compound useful as a therapeutic agent for chronic renal insufficiency and diabetic nephropathy.

Means for Solving the Problem

At first, the present applicants have made studies on a compound having an antagonistic action against an EP4 receptor, and as a result, they have found that the compound as disclosed in Patent Document 1 has a good antagonistic action against an EP4 receptor. Then, the present inventors have made further studies, and thus, they have found that by the introduction of a cycloalkanediyl structure, physicochemical properties such as solubility, and the like can be improved, thereby giving further preferred properties as a pharmaceutical, thereby completing the present invention.

Specifically, the present invention relates to a compound of the formula (I) or a pharmaceutically acceptable salt thereof, and a pharmaceutical composition containing the compound of the formula (I) or a pharmaceutically acceptable salt thereof, and a pharmaceutically acceptable excipient.

[Chem. 2]

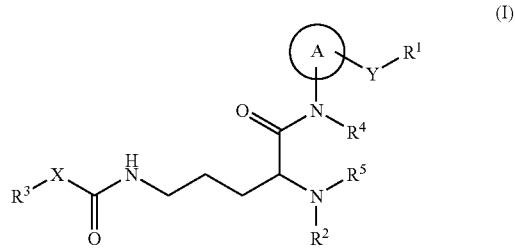

(wherein
A represents cycloalkanediyl,
X represents a single bond, —O—, —NH—, or —NR⁰—,
Y represents a single bond, —R⁰⁰—, or —Y¹—R⁰⁰—,
Y¹ represents —O—, —S—, —S(O)—, —S(O)₂—, or —NHS(O)₂—,
R¹ represents —CO₂H or a biological equivalent thereof,
R² represents —R⁰, —C(O)—R⁰, —R²¹, —C(O)—R²¹,
R²¹ represents -(aryl which may be substituted), -(hetero ring which may be substituted), —R⁰⁰-(aryl which may be substituted), —R⁰⁰-(hetero ring which may be substituted), -(lower alkenylene)-(aryl which may be substituted), or -(lower alkenylene)-(hetero ring which may be substituted),
R³ represents —R⁰, -(aryl which may be substituted), -(cycloalkyl which may be substituted), —R⁰⁰-(aryl which may be substituted), or —R⁰⁰-(cycloalkyl which may be substituted), $R^4$ and $R^5$ each represent H or $R^0$, $R^0$ represents lower alkyl, and $R^{00}$ represents lower alkylene.

Hereinbelow, these symbols have the same meanings as defined above unless otherwise specifically mentioned in the present specification).

Further, the present invention relates to a pharmaceutical composition for treating chronic renal insufficiency or diabetic nephropathy, containing the compound of the formula (I) or a pharmaceutically acceptable salt thereof, specifically, to a prophylactic or therapeutic agent for chronic renal insufficiency or diabetic nephropathy, containing the compound of the formula (I) or a pharmaceutically acceptable salt thereof.

In addition, the present invention further relates to use of the compound of the formula (I) or a pharmaceutically acceptable salt thereof for the production of a therapeutic agent for chronic renal insufficiency or a therapeutic agent for diabetic nephropathy, and a method for treating chronic renal insufficiency or diabetic nephropathy, comprising administering to a patient an effective amount of the compound of the formula (I) or a pharmaceutically acceptable salt thereof.

EFFECT OF THE INVENTION

The compound of the formula (I) or a pharmaceutically acceptable salt thereof has an antagonistic action against an EP4 receptor, and therefore, it can be used as a prophylactic and/or therapeutic agent for renal diseases, particularly chronic renal insufficiency or diabetic nephropathy, or the like.

BEST MODE FOR CARRYING OUT THE INVENTION

Hereinbelow, the present invention will be described in detail.

In the present specification, the "lower alkyl" preferably refers to a linear or branched alkyl group having 1 to 6 carbon atoms (which is hereinafter simply referred to as $C_{1-6}$), for example, a methyl group, an ethyl group, an n-propyl group, an isopropyl group, an n-butyl group, an isobutyl group, a sec-butyl group, a tert-butyl group, an n-pentyl group, an n-hexyl group, or the like. In an embodiment, it is a $C_{1-4}$ alkyl group, and in another embodiment, a methyl group, an ethyl group, or a tert-butyl group.

The "lower alkenyl" refers to a linear or branched $C_{2-6}$ alkenyl group, for example, a vinyl group, a propenyl group, a butenyl group, a pentenyl group, a 1-methylvinyl group, a 1-methyl-2-propenyl group, a 1,3-butadienyl group, a 1,3-pentadienyl group, or the like. In another embodiment, it is $C_{2-4}$ alkenyl, in a further embodiment, vinyl or propenyl, and in yet another embodiment, propenyl.

The "lower alkylene" refers to a divalent group ($C_{1-6}$ alkylene) formed by the removal of one hydrogen atom at any position of the above-described "lower alkyl". In an embodiment, it is a $C_{1-4}$ alkylene group, in another embodiment, a $C_{1-3}$ alkylene group, and in a further embodiment, a $C_{1-2}$ alkylene group.

The "lower alkenylene" refers to a linear or branched $C_{2-6}$ alkenylene group, for example, a vinylene group, an ethylidene group, a propenylene group, a butenylene group, a pentenylene group, a hexenylene group, a 1,3-butadienylene group, a 1,3-pentadienylene group, or the like. In an embodiment, it is a $C_{2-4}$ alkenylene group, and in another embodiment, an ethylidene group or a propenylene group.

The "halogen" means F, Cl, Br, or I.

The "halogeno-lower alkyl" refers to a $C_{1-6}$ alkyl group substituted with one or more halogen atoms. In an embodiment, it is a lower alkyl group substituted with 1 to 5 halogen atoms, and in another embodiment, a trifluoromethyl group, a 2-fluoroethyl group, or a 3-fluoropropyl group.

The "cycloalkyl" refers to a $C_{3-10}$ saturated hydrocarbon ring group, which may have a bridge. It is, for example, a cyclopropyl group, a cyclobutyl group, a cyclopentyl group, a cyclohexyl group, a cycloheptyl group, a cyclooctyl group, an adamantyl group, or the like. In an embodiment, it is a $C_{3-8}$ cycloalkyl group, in another embodiment, a $C_{3-6}$ cycloalkyl group, and in an even further embodiment, a cyclopentyl group or a cyclohexyl group.

The "cycloalkanediyl" and the "cycloalkylene" each refer to a divalent group ($C_{3-8}$ cycloalkanediyl) formed by removal of any two hydrogen atoms of the $C_{3-8}$ cycloalkane, and the binding position may be any one of 1,1-, 1,2-, 1,3-, or 1,4-diyl. In an embodiment, it is cyclobutanediyl, cyclopentanediyl, or cyclohexanediyl, and in another embodiment, 1,2-cyclobutanediyl, 1,2-cyclopentanediyl, or 1,2-cyclohexanediyl.

The "aryl" refers to a $C_{6-14}$ mono- to tricyclic aromatic hydrocarbon ring group, which contains a partially hydrogenated ring group. It is, for example, a phenyl group, a naphthyl group, a 5-tetrahydronaphthyl group, a 4-indenyl group, a 1-fluorenyl group, or the like. In an embodiment, it is phenyl or naphthyl, and in another embodiment, phenyl.

The "hetero ring" means a ring group containing i) a monocyclic 3- to 8-membered, and in another embodiment, 5- to 7-membered hetero ring, containing 1 to 4 hetero atoms selected from oxygen, sulfur, and nitrogen, and ii) a bi- to tricyclic hetero ring containing 1 to 5 hetero atoms selected from oxygen, sulfur, and nitrogen, formed by condensation with one or two rings in which the monocyclic hetero ring is selected from a monocyclic hetero ring, a benzene ring, $C_{5-8}$ cycloalkane, and $C_{5-8}$ cycloalkene. The ring atom, sulfur or nitrogen, may be oxidized to form an oxide or a dioxide.

As the "hetero ring", the following embodiments may be mentioned:

(1) Monocyclic saturated hetero ring i) those containing 1 to 4 nitrogen atoms, for example, azepanyl, diazepanyl, aziridinyl, azetidinyl, pyrrolidinyl, imidazolyldinyl, piperidinyl, pyrazolidinyl, piperazinyl, azocanyl, and the like;

ii) those containing 1 to 3 nitrogen atoms and 1 to 2 sulfur atoms and/or 1 to 2 oxygen atoms, for example, thiomorpholinyl, thiazolidinyl, isothiazolidinyl, oxazolidinyl, morpholinyl, and the like;

iii) those containing 1 to 2 sulfur atoms, for example, tetrahydrothiinyl and the like;

iv) those containing 1 to 2 sulfur atoms and 1 to 2 oxygen atoms, for example, oxathiolane, and the like;

v) those containing 1 to 2 oxygen atoms, for example, oxiranyl, dioxoranyl, oxoranyl, tetrahydropyranyl, 1,4-dioxanyl, and the like;

(2) Monocyclic unsaturated hetero ring group i) those containing 1 to 4 nitrogen atoms, for example, pyrrolyl, imidazolyl, pyrazolyl, pyridyl, dihydropyridyl, pyrimidinyl, pyrazinyl, pyridazinyl, triazolyl, tetrazolyl, dihydrotriazinyl, azepinyl, and the like;

ii) those containing 1 to 3 nitrogen atoms and 1 to 2 sulfur atoms and/or 1 to 2 oxygen atoms, for example, thiazolyl, isothiazolyl, thiadiazolyl, dihydrothiazinyl, oxazolyl, isooxazolyl, oxadiazolyl, oxadinyl, and the like;

iii) those containing 1 to 2 sulfur atoms, for example, thienyl, thiepinyl, dihydrodithiinyl, dihydrodithionyl, and the like;

iv) those containing 1 to 2 sulfur atoms and 1 to 2 oxygen atoms, for example, dihydrooxathiinyl, and the like;

v) those containing 1 to 2 oxygen atoms, for example, furyl, pyranyl, oxepinyl, dioxolyl, and the like;

(3) Condensed polycyclic saturated hetero ring group i) those containing 1 to 5 nitrogen atoms, for example, quinuclidine, 7-azabicyclo[2.2.1]heptyl, 3-azabicyclo[3.2.2] nonanyl, and the like;

ii) those containing 1 to 4 nitrogen atoms and 1 to 3 sulfur atoms and/or 1 to 3 oxygen atoms, for example, trithiadiaza-indenyldioxoloimidazolidinyl, and the like;

iii) those containing 1 to 3 sulfur atoms and/or 1 to 3 oxygen atoms, for example, 2,6-dioxabicyclo[3.2.2]octo-7-yl, and the like;

(4) Condensed polycyclic unsaturated hetero ring i) those containing 1 to 5 nitrogen atoms, for example, indolyl, isoindolyl, indolinyl, indolidinyl, benzoimidazolyl, quinolyl, tetrahydroquinolyl, isoquinolyl, tetrahydroisoquinolyl, indazolyl, imidazopyridyl, benzotriazolyl, tetrazolopyridazinyl, carbazolyl, quinoxalinyl, dihydroindazolyl, benzopyrimidinyl, naphthyridinyl, quinazolinyl, cinnolinyl, and the like;

ii) those containing 1 to 4 nitrogen atoms and 1 to 3 sulfur atoms and/or 1 to 3 oxygen atoms, for example, benzothiazolyl, dihydrobenzothiazolyl, benzothiadiazolyl, imidazothiazolyl, imidazothiadiazolyl, benzooxazolyl, benzooxadiazolyl, and the like;

iii) those containing 1 to 3 sulfur atoms, for example, benzothienyl, benzodithiinyl, and the like;

iv) 1 to 3 sulfur atoms and 1 to 3 oxygen atoms, for example, benzooxathiinyl, phenoxadinyl, and the like;

v) those containing 1 to 3 oxygen atoms, for example, benzodioxolyl, benzofuranyl, isobenzofuranyl, chromenyl, benzodihydrofuranyl, and the like;

The "nitrogen-containing hetero ring" means that at least one nitrogen atom is contained in the hetero ring, as in i) and ii) of (1), i) and ii) of (2), i) and ii) of (3), i) and ii) of (4), and the like.

The "—$CO_2H$ or a biological equivalent thereof" means —$CO_2H$, or another atom or atom group having an electronic or steric configuration that is equivalent to —$CO_2H$ and having common biological properties, and includes a carboxylic acid bioisostere, a protected carboxylic group, or a prodrug of a carboxylic acid, in the narrow meaning usually used by a skilled person in the art.

The —$CO_2H$ or the "carboxylic acid bioisostere in a narrow meaning" means a group capable of releasing acidic protons, in an embodiment, examples thereof include —$CO_2H$, hydroxamic acid (R—CO—NH—OH), acylcyanamide (R—CO—NH—CN), acylsulfonamide (R—CO—NH—$SO_2$—R'), tetrazole, oxadiazolone, oxadiazolthione, oxathiadiazole, thiadiazolone, triazolthione, hydroxyisoxazole, and the like, and in another embodiment, include —$CO_2H$, acylsulfonamide, tetrazole, oxadiazolone, oxadiazolthione, and thiadiazolone.

Examples of the "protected carboxylic" group can include the following:

(1) Esterified carboxylic group, specifically a —CO—O—$R^0$ group, a —CO—O-(lower alkenyl) group, a —CO—O-(lower alkynyl) group, a —CO—$R^{00}$—O—$R^0$ group, a —CO—O—$R^{00}$-(aryl) group, a —CO—O—$R^{00}$—O-(aryl) group, or the like; and (2) Amidated carboxylic group, specifically a —CO—$NH_2$ group, a —CO—NH—$R^0$ group, a —CO—$NR^0{}_2$ group, a —CO—N($R^0$)-(aryl) group, a —CO—N($R^0$)—$R^{00}$-(aryl) group, a —CO—NH—$R^{00}$—OH group, a —CO—NH—$R^{00}$—$CO_2H$ group, or the like.

In (1) and (2) above, the "aryl" may be substituted with a methoxy group.

The "prodrug of a carboxylic acid" means a substituent that can be converted into —$CO_2H$ by solvolysis or under a physiological condition.

The expression "which may be substituted" means that it is "not substituted" or "substituted with 1 to 5 substituents which are the same as or different from each other". Further, if it has a plurality of substituents, the substituents may be the same as or different from each other.

The substituent for the "aryl which may be substituted", the "hetero ring which may be substituted", and the "cycloalkyl which may be substituted" is a group selected from —$R^0$, —$R^{00}$—OH, —$R^{00}$—$OR^0$, —OH, —$OR^0$, —O—$R^{00}$—OH, —O—$R^{00}$—O-(hetero ring), —O—C(O)—$R^{00}$, halogen, oxo, —$NR^0{}_2$, —NH—$SO_2$—$R^0$, —$NR^0$—CO—$R^0$, —NH—$R^{00}$—$OR^0$, —$NR^0$—$R^{00}$—$OR^0$, —CO—$R^0$, —$SO_2$—$R^0$, -(lower alkenyl), phenyl, pyrrolidinyl, pyrrolyl which may be substituted with a lower alkyl group, pyrazolyl, piperidinyl, and piperazinyl, and in another embodiment, a group selected from —$R^0$, —$R^{00}$—OH, —$R^{00}$—$OR^0$, —OH, halogen, and —$NR^0{}_2$.

Embodiments of the present invention will be described below.

(1) The compound, wherein A is $C_{3-6}$ cycloalkanediyl, for example, cyclopropane-1,2-diyl, cyclobutane-1,2-diyl, cyclopentane-1,2-diyl, or cyclohexane-1,2-diyl, in an embodiment, cyclopentane-1,2-diyl or cyclohexane-1,2-diyl, and in another embodiment, cyclopentane-1,2-diyl, in an even further embodiment, cis-cyclopentane-1,2-diyl or cis-cyclohexane-1,2-diyl, and in yet another embodiment, cis-cyclopentane-1,2-diyl.

(2) The compound, wherein X is a single bond or —O—, and in an embodiment, —O—.

(3) The compound, wherein Y is a single bond, $C_{1-4}$ alkylene, or —O—($C_{1-2}$ alkylene)-, in an embodiment, a single bond, methylene, ethylene, or —O—$CH_2$—, and in another embodiment, a single bond.

(4) The compound, wherein $R^1$ is —$CO_2H$, —$CO_2$—($C_{1-4}$ alkyl), —CO—NH—$SO_2$—$R^0$, —CO—NH—$SO_2$—$R^{00}$—OH, —CO—NH—$SO_2$-(halogeno-lower alkyl), tetrazol-5-yl, 5-thioxo-4,5-dihydro-1,3,4-oxadiazol-2-yl, 5-oxo-4,5-dihydro-1,2,4-oxadiazol-3-yl, or 2-oxide-3H-1,2,3,5-oxathiazol-4-yl, in another embodiment, —$CO_2H$, —$CO_2$—($C_{1-4}$ alkyl), —CO—NH—$SO_2$—($C_{1-4}$ alkylene)-OH, or tetrazol-5-yl, and in yet another embodiment, —$CO_2H$, —$CO_2$—($C_{1-4}$ alkyl), or tetrazol-5-yl.

(5) The compound, wherein $R^2$ is —C(O)—$R^{21}$.

(6) The compound, wherein $R^{21}$ is phenyl or a mono- or bicyclic hetero ring, each of which may be substituted with a group selected from Group $G^0$, or —CH═CH-(phenyl which may be substituted with a group selected from Group $G^0$), in another embodiment, phenyl, pyridyl, pyrrolyl, pyrazolyl, indolyl, imidazopyridyl, quinolyl, benzofuryl, or -(lower alkenylene)-(phenyl), each of which may be substituted with a group selected from Group $G^0$, in an even further embodiment, phenyl, pyrrolyl, indolyl, quinolyl, or -(lower alkenylene)-(phenyl), each of which may be substituted with a group selected from Group $G^0$, and in yet another embodiment, indolyl or quinolyl, each of which may be substituted with a group selected from Group $G^0$. Here, Group $G^0$ means a substituent group consisting of —$R^0$, —OH, —$OR^0$, halogen, acetyl, and —N($R^0$)$_2$, and in another embodiment, a substituent group consisting of —$R^0$, —OH, halogen, acetyl, and —N($R^0$)$_2$.

(7) The compound, wherein $R^3$ is —$R^0$, —$R^{00}$-(aryl which may be substituted), or —$R^{00}$-(cycloalkyl which may be substituted), in another embodiment, —CH$_2$-(phenyl which may be substituted with a group selected from Group G$^0$), and in an even further embodiment, benzyl.

(8) The compound, wherein R$^4$ and R$^5$ are H.

(9) The compound, wherein the configuration of the ornithine part of the compound of the formula (I) is the same as that of natural L-ornithine.

(10) The compound, including a combination of at least two of (1) to (9).

As another embodiment, the following compounds may be mentioned.

(11) The compound, wherein A is cyclopentane-1,2-diyl or cyclohexane-1,2-diyl, X is —O—, R$^2$ is —C(O)—R$^{21}$, R$^{21}$ is phenyl, pyridyl, pyrrolyl, pyrazolyl, indolyl, imidazopyridyl, quinolyl, benzofuryl, or -(lower alkenylene)-(phenyl), each of which may be substituted with a group selected from —C(O)—R$^{21}$, R$^{21}$ is —R$^0$, —OH, —OR$^0$, halogen, acetyl, and —N(R$^0$)$_2$, and R$^3$ is —R$^0$, —R$^{00}$-(aryl which may be substituted), or —R$^{00}$-(cycloalkyl which may be substituted).

(12) The compound, wherein A is cyclopentane-1,2-diyl, R$^{21}$ is phenyl, pyrrolyl, indolyl, quinolyl, or -(lower alkenylene)-(phenyl), each of which may be substituted with a group selected from —R$^0$, —OH, halogen, acetyl, and —N(R$^0$)$_2$, and R$^3$ is benzyl.

Examples of the specific compounds encompassed by the present invention include the following compounds.

(1R,2S)-2-({N$^5$-[(benzyloxy)carbonyl]-N$^2$-(quinolin-2-ylcarbonyl)-L-ornithyl}amino)cyclopentanecarboxylic acid, (1R,2S)-2-({N$^5$-[(benzyloxy)carbonyl]-N$^2$-[(1-methyl-1H-indol-6-yl)carbonyl]-L-ornithyl}amino)cyclopentanecarboxylic acid, (1R,2S)-2-({N$^5$-[(benzyloxy)carbonyl]-N$^2$-[3-(dimethylamino)benzoyl]-L-ornithyl}amino)cyclopentanecarboxylic acid, (1R,2S)-2-({N$^5$-[(benzyloxy)carbonyl]-N$^2$-(3-chlorobenzoyl)-L-ornithyl}amino)cyclopentanecarboxylic acid, (1R,2S)-2-({N$^5$-[(benzyloxy)carbonyl]-N$^2$-[(1-methyl-1H-indol-4-yl)carbonyl]-L-ornithyl}amino)cyclopentanecarboxylic acid, (1R,2S)-2-({N$^5$-[(benzyloxy)carbonyl]-N$^2$-[(2E)-3-(2-hydroxyphenyl)furfur-2-enoyl]-L-ornithyl}amino)cyclopentanecarboxylic acid, (1R,2S)-2-({N$^5$-[(benzyloxy)carbonyl]-N$^2$-[(1,4-dimethyl-1H-pyrrol-2-yl)carbonyl]-L-ornithyl}amino)cyclopentanecarboxylic acid, (1R,2S)-2-({N$^2$-[(3-acetyl-1-methyl-1H-indol-6-yl)carbonyl]-N$^5$-[(benzyloxy)carbonyl]-L-ornithyl}amino)cyclopentanecarboxylic acid, and (1R,2S)-2-({N$^5$-[(benzyloxy)carbonyl]-N$^2$-[(1-methyl-1H-indol-7-yl)carbonyl]-L-ornithyl}amino)cyclopentanecarboxylic acid.

The compound of the formula (I) may in some cases exist in the form of other tautomers or geometrical isomers, depending on the kinds of the substituents. In the present specification, the compound may be described in only one form of isomer, but the present invention includes the isomers, isolated forms of the isomers, or a mixture thereof.

Furthermore, the compound of the formula (I) may have asymmetric carbon atoms or asymmetries in some cases, and correspondingly, it may exist in the form of optical isomers such as an R-form and an S-form. The present invention includes both a mixture and an isolated form of these optical isomers.

Further, the "pharmaceutically acceptable prodrugs" of the compound of the formula (I) are also included in the present invention. The "pharmaceutically acceptable prodrug" is a compound having a group which can be converted into an amino group, a hydroxyl group, a carboxyl group, and the like, of the present invention, by solvolysis or under a physiological condition. Examples of the group for forming a prodrug include those as described in Prog. Med., 5, 2157-2161 (1985) or "Iyakuhin no Kaihatsu (Development of Medicines)" (Hirokawa Shoten, 1990), vol. 7, "Bunshi Sekkei (Molecular Design)", pp. 163-198.

Furthermore, the compounds of the formula (I) may form a salt with an acid or a base, depending on the kind of the substituents, and this salt is included in the present invention, as long as it is a pharmaceutically acceptable salt. Specifically, examples thereof include acid addition salts with inorganic acids such as hydrochloric acid, hydrobromic acid, hydroiodic acid, sulfuric acid, nitric acid, phosphoric acid, and the like, and with organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, p-toluenesulfonic acid, aspartic acid, glutamic acid, and the like, and salts with inorganic bases such as sodium, potassium, magnesium, calcium, aluminum, and the like, and organic bases such as methylamine, ethylamine, ethanolamine, lysine, ornithine, and the like, ammonium salts, and others.

Furthermore, the present invention also includes various hydrates or solvates, and polymorphic crystal substances of the compound of the formula (I) and a pharmaceutically acceptable salt thereof. Also, furthermore, the present invention includes the compounds labeled with various radioactive isotopes or non-radioactive isotopes.

(Production Methods)

The compound of the formula (I) and a pharmaceutically acceptable salt thereof can be prepared by applying various known synthetic methods, using the characteristics based on their basic skeletons or the kinds of the substituents. At this time, depending on the types of the functional groups, it is in some cases effective from the viewpoint of the production techniques to substitute the functional group with an appropriate protecting group (a group which is capable of being easily converted into the functional group), during the steps from starting materials to intermediates. Examples of such a functional group include an amino group, a hydroxyl group, a carboxyl group, and the like, and examples of the protecting group thereof include those as described in "Protective Groups in Organic Synthesis (3$^{rd}$ edition, 1999)", edited by Greene and Wuts, and the like, which may be appropriately selected and used depending on the reaction conditions. In these methods, a desired compound can be obtained by introducing the protecting group to carry out the reaction, and then, if desired, removing the protecting group.

In addition, the prodrug of the compound of the formula (I) can be prepared by introducing a specific group during the steps from starting materials to intermediates, in the same manner as for the afore-mentioned protecting groups, or by carrying out the reaction using the obtained compound of the formula (I). The reaction can be carried out by applying a method known by a person skilled in the art, such as common esterification, amidation, dehydration, and the like.

Hereinbelow, the representative production methods for the compound of the formula (I) will be described. Each of the production processes may also be carried out with reference to the References appended in the present description. Further, the production methods of the present invention are not limited to the examples as shown below.

(Production Process 1)

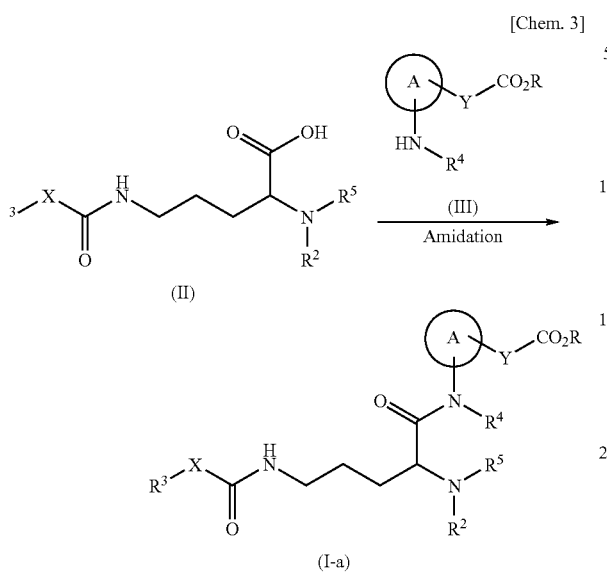

(wherein R represents $C_{1-4}$ alkyl or a protecting group of a carboxylic acid).

The present production process is a method for obtaining the present compound (I-a) by reacting a compound (II) with a compound (III).

The reaction can be carried out using the compound (II) and the compound (III) in equivalent amounts or either thereof in an excessive amount in the presence of a condensing agent, from under cooling to under heating, preferably at −20° C. to 60° C. usually stirring for 0.1 hour to 5 days, in a solvent which is inert to the reaction. Here, the solvent is not particularly limited, but examples thereof include aromatic hydrocarbons such as benzene, toluene, xylene, and the like, halogenated hydrocarbons, such as dichloromethane (DCM), 1,2-dichloroethane (DCE), chloroform, and the like, ethers such as diethyl ether, tetrahydrofuran (THF), dioxane, dimethoxyethane (DME), and the like, N,N-dimethylformamide (DMF), dimethyl sulfoxide (DMSO), ethyl acetate, acetonitrile, water, and the like, or a mixture thereof. Examples of the condensing agent include, but are not limited to, 1-[bis(dimethylamino)methylene]-1H-1,2,3-triazolo[4,5-b]pyridin-1-ium-3-oxaide hexafluorophosphate (HATU), 1-(3-dimethylaminopropyl)-3-ethylcarbodiimide (WSC), dicyclohexylcarbodiimide (DCC), 1,1'-carbonyldiimidazole (CDI), diphenylphosphoryl azide, phosphorus oxychloride, and the like. It is favorable for the reaction in some cases to use an additive (for example, 1-hydroxybenzotriazole (HOBt), and the like) in some cases. It may be advantageous in some cases for the smooth progress of the reaction to carry out the reaction in the presence of an organic salt such as triethylamine, N,N-diisopropylethylamine (DIPEA), N-methylmorpholine, and the like, or an inorganic salt such as potassium carbonate, sodium carbonate, potassium hydroxide, and the like.

Further, a method in which the compound (II) is derived into a reactive derivative thereof, and then the reactive derivative is reacted with the compound (III) can also be used. Here, examples of the reactive derivative of the carboxylic acid include oxyhalides obtained by the reaction of a halogenating agent such as phosphorus oxychloride, thionyl chloride, and the like, mixed acid anhydrides such as isobutyl chloroformate, and the like, active esters obtained by condensation with HOBt, and the like. The reaction of the reactive derivative and the compound (III) can be carried out, from under cooling to under heating, preferably at −20° C. to 60° C., in a solvent which is inert to the reaction, such as halogenated hydrocarbons, aromatic hydrocarbons, ethers, and the like.

(Production Process 2)

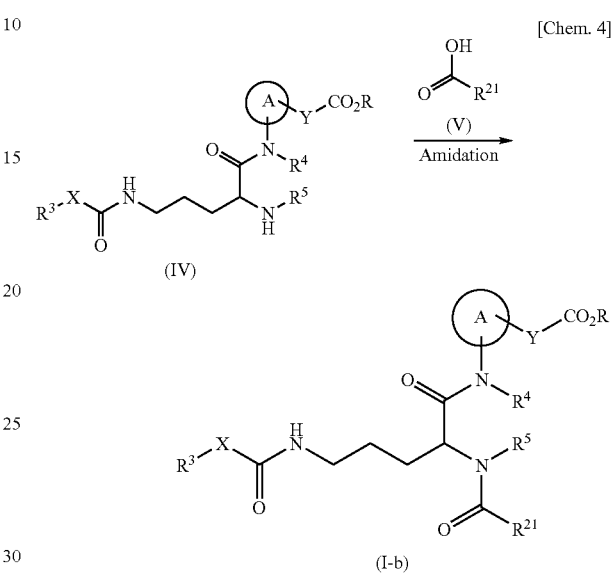

The present production process is a method for obtaining a compound (I-b) of the present invention by carrying out the amidation of an amine (IV) and a carboxylic acid (V). The amidation can be carried out by using various reaction conditions represented by the above-described Production Process 1

(Production Process 3)

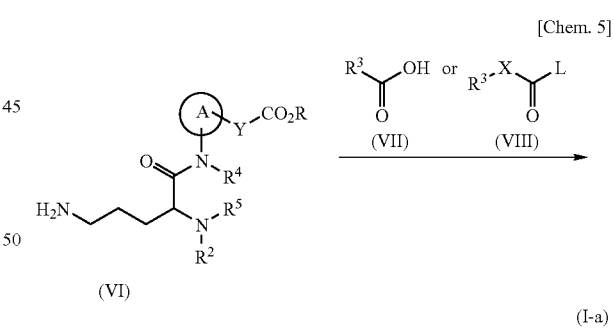

(wherein L represents a leaving group, preferably Cl or a 4-nitrophenoxy group).

Further, the compound (I-a) of the present invention can be prepared by reacting a compound (VI) with a compound (VII) or a compound (VIII). In the case of using the compound (VII), production can be made by using the same condition as the above-described Production Process 1. Further, in the case of using the compound (VIII), the reaction can be carried out using the compound (VI) and the compound (VIII) in equivalent amounts or either thereof in an excessive amount, from under cooling to heating under reflux, preferably at 0° C. to 80° C. usually stirring for 0.1 hour to 5 days, in a solvent which is inert to the reaction or without a solvent. Here, the solvent is not particularly limited, but examples thereof include aromatic hydrocarbons, ethers, halogenated hydrocarbons, DMF, DMSO, ethyl acetate, acetonitrile as shown in Production Process 1, or a mixture thereof. It may be advantageous in some cases for the smooth progress of the reaction to carry out the reaction in the presence of an organic base such as triethylamine, N,N-diisopropylethylamine, N-methylmorpholine, and the like, or an inorganic base such as potassium carbonate, sodium carbonate, potassium hydroxide, and the like.

As the compound (VIII), various alkyl chloroformates or alkyl 4-nitrophenylcarbamates can be used. The alkyl 4-nitrophenylcarbamate can be prepared by performing a reaction using 4-nitrophenyl chlorocarbamate and a corresponding alcohol in equivalent amounts or either thereof in an excessive amount at −20° C. to 80° usually for about 0.1 hour to 1 day, from under cooling to under heating, in the presence of a base, in a solvent which is inert to the reaction.

Further, in the compound (I-a) and the compound (I-b) of the present invention, by hydrolysis at an ester site with an acid or an alkali, or by removal of the protecting group of a carboxylic acid, the compound of the formula (I) in which the R site is H can be obtained.

(Production Process 4)

reaction, and in an embodiment, by stirring it at 0° C. to room temperature, usually for 0.1 hour to 5 days. Here, the solvent is not particularly limited, but examples thereof include alcohols such as methanol, ethanol, and the like, ethers, or a mixture thereof. Examples of the reducing agent include sodium cyanoborohydride, triacetoxy sodium borohydride, sodium borohydride, and the like. It is preferable in some cases to carry out the reaction in the presence of a dehydrating agent such as molecular sieves, and the like or an acid such as acetic acid, hydrochloric acid, a titanium (IV) isopropoxide complex, and the like. Depending on the reaction, when an imine compound formed as an intermediate in the reaction system may be stably isolated, a reducing reaction may be separately carried out after obtaining the imine compound. Further, the reaction can be carried out in a solvent such as methanol, ethanol, ethyl acetate, and the like, in the presence or absence of an acid such as acetic acid, hydrochloric acid, and the like, using a reduction catalyst (for example, palladium-carbon, Raney nickel, and the like), instead of treatment with the reducing agent. In this case, it is preferable to carry out the reaction under a hydrogen atmosphere at normal pressure to 50 atmospheres under heating from 0° C.

(Production Process 5)

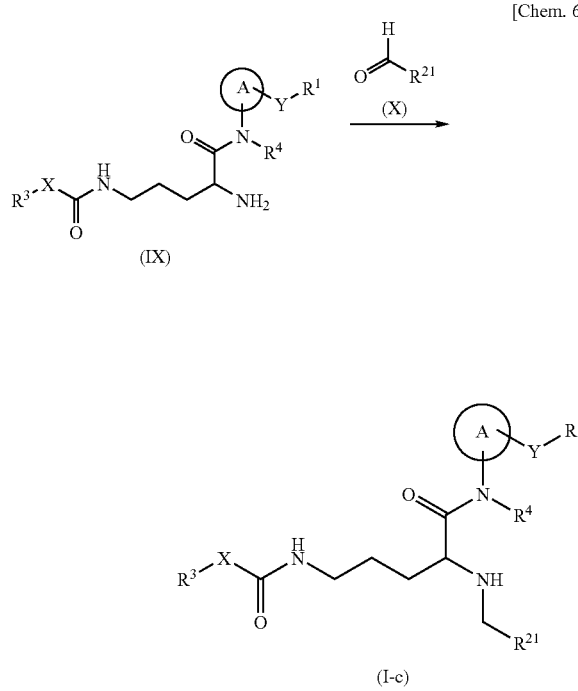

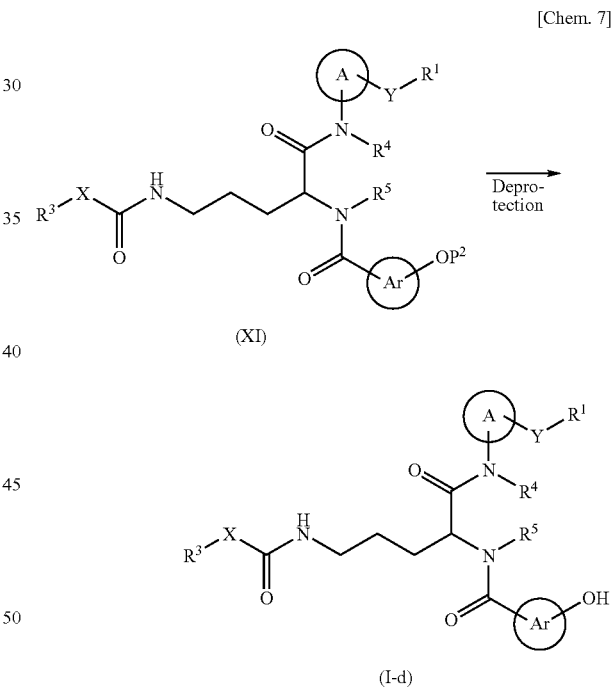

(wherein Ar means aryl which may be substituted or a hetero ring which may be substituted. Further, $P^2$ means a protecting group of a phenol, for example acetyl or tetrahydropyranyl. These symbols have the same meanings as defined above unless specifically otherwise mentioned in the present specification).

The present production process is a method for obtaining a compound (I-c) of the present invention by reacting a compound (IX) with a compound (X).

The reaction is carried out by using the compound (IX) and the compound (X) in equivalent amounts or either thereof in an excessive amount at −45° C. to heating under reflux in the presence of a reducing agent in a solvent which is inert to the The compound (I-d) of the present invention can be prepared by deprotection of the protecting group of the hydroxyl group of the compound (XI) under the condition depending on the types thereof, for example, by the method as described in "Protective Groups in Organic Synthesis ($3^{rd}$ edition, 1999)".

(Production Process 6)

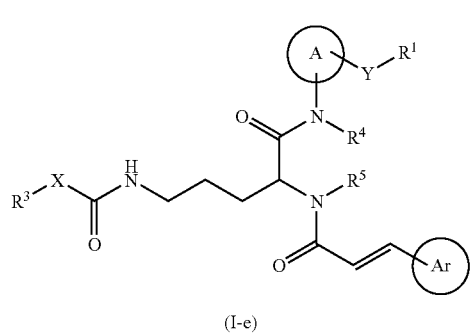

(I-e)

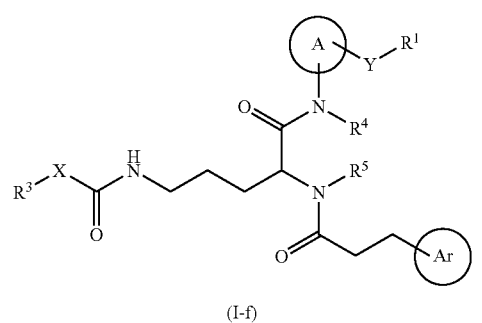

(I-f)

The compound (I-f) of the present invention can be prepared by reduction of an olefin of the compound (I-e) of the present invention.

(Starting Material Synthesis)
Starting Material Production Process 1

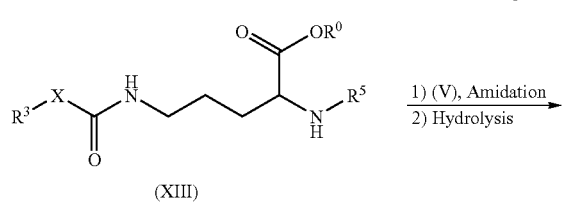

(XIII)

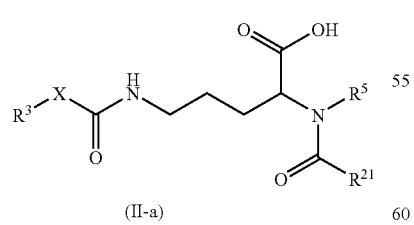

(II-a)

The compound (II-a) can be prepared by subjecting a compound (XIII) and a carboxylic acid (V) to amidation in the same manner as in the method represented by Production Process 1, and then subjecting the carboxylic ester to hydrolysis under acid or alkali conditions.

Starting Material Production Process 2

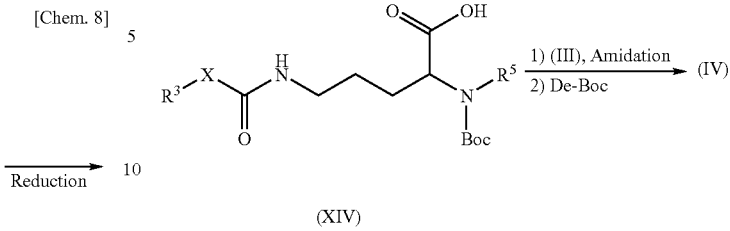

(XIV)

The compound (IV) can be prepared by subjecting a compound (XIV) and the amine (III) to amidation in the same manner as in the method represented by Production Process 1, and then removing the tert-butoxycarbonyl group.

Starting Material Production Process 3

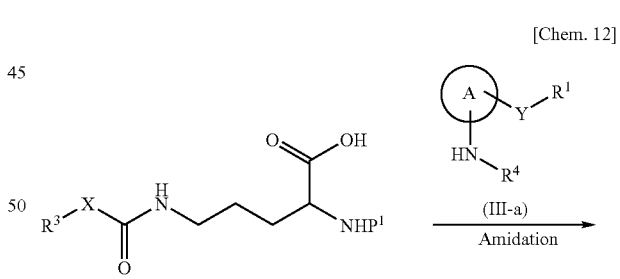

(XV)

(wherein $P^1$ represents a protecting group of an amino group, and preferably a benzyloxycarbonyl group. Hereinbelow, these symbols have the same meanings as defined above unless otherwise specifically mentioned in the present specification).

The compound (IV) can be prepared by removing the protecting group of an amino group of the compound (XV).

Starting Material Production Process 4

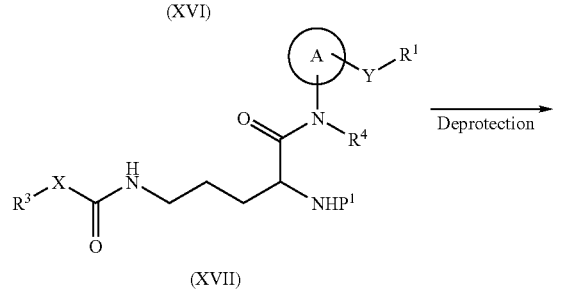

(XVI)

(XVII)

(IX)

(wherein $P^1$ represents a protecting group of an amino group, and preferably a (9H-fluorene-9-ylmethoxy)carbonyl group).

The compound (IX) can be prepared by reacting a compound (XVI) with an amine (III-a) in the same manner as in the method represented by Production Process 1, and then subjecting the obtained compound (XVII) to deprotection.

The compound of the formula (I) is isolated and purified as its free compound, a pharmaceutically acceptable salt, a hydrate, a solvate, or a polymorphic crystal substance thereof. The pharmaceutically acceptable salt of the compound of the formula (I) can also be prepared in accordance with a conventional method for a salt formation reaction.

Isolation and purification are carried out by employing common chemical operations such as extraction, fractional crystallization, various types of fraction chromatography, and the like.

Various isomers can be prepared by selecting an appropriate starting compound, or can be separated by making use of the difference in the physicochemical properties between isomers. For example, the optical isomer can be derived into an optically pure isomer by means of general optical resolution methods (for example, fractional crystallization for inducing diastereomers with optically active bases or acids, chromatography using a chiral column, etc., and the like). In addition, the isomers can also be prepared from an appropriate optically active starting material.

The pharmacological activity of the compound of the formula (I) was confirmed by the following test.

Test Example 1: Evaluation Test on Rat EP4 Receptor Affinity

Cell Culture and Transfection

Using a 10 cm collagen-coated dish (Asahi Glass), HEK293 cells were cultured in a D-MEM culture medium, washed with a phosphate buffer saline (PBS), the culture medium was removed off at a confluence (90 to 100% density state), and then the cells were detached with N,N,N',N'-tetrakis(carboxymethyl)ethylenediamine (EDTA). The cells were counted and seeded on a 15 cm collagen-coated dish to a confluence of 70%. The next day, to an Opti-MEM culture medium at 1.2 mL/dish was added Lipofectamine 2000 (Invitrogen) at 60 µL/dish, followed by being left to stand at room temperature for 5 minutes. A plasmid in which a rat EP4 (alignment number 1) had been inserted into a TA cloning site of pcDNA3.1-V5-His-topo was added thereto to 15 µg/dish. After leaving it to stand at room temperature for 30 minutes, the resultant was added to the dish, and cultured for 20 to 24 hours. The cell culture was carried out in a $CO_2$ incubator (37° C., 5% $CO_2$).

Preparation of Membrane Fraction

The culture medium was removed by suction, 10 mL of cooled PBS was added thereto per 15 cm dish, and the cells were scraped using a cell scraper (Sumitomo Bakelite). They were washed with cooled PBS (1,200 rpm, 4° C., 5 min), and then suspended in 6 mL of cooled 20 mM Tris-HCl (pH 7.4; Nakalai Tesque Inc., including 5 mM EDTA (Nakalai Tesque Inc.) per dish. Then, it was homogenized using a Polytron and the homogenate was centrifuged (26,000 rpm, 20 min, 4° C.). The obtained precipitate was resuspended in cooled 20 mM Tris-HCl, and homogenized again using a Polytron, and the homogenate was centrifuged (26,000 rpm, 20 min, 4° C.). The obtained precipitate was resuspended in 50 mM HEPES (pH 7.5; Dojindo Laboratories) to 1 mL per dish, homogenized again using a Polytron, and freeze-stored at −80° C. as a membrane fraction. At this time, a part thereof was used for the measurement of the protein concentration. Measurement of the protein concentration was carried out using a Bio-Rad Protein assay kit (Bio-Rad Laboratories) in accordance with the appended standard Protocol in duplicate.

Binding Assay

[$^3$H] PGE2 50 µL (final concentration 0.3 nM; Perkin Elmer), 100 µL (20 µg/well) of a membrane fraction prepared from the rat EP4 expression cell, and 50 µL of a test compound were mixed in a 96-well microplate (Sumitomo Bakelite), incubated at room temperature for 1 hour, then filtered by suction on a UniFilter-96 GF/B (Perkin Elmer) using a FilterMate Harvester (Perkin Elmer), and washed three times with 300 µL/well of a cooled assay buffer. Dilution of [$^3$H]PGE2 and the membrane fraction was carried out using an assay buffer (50 mM HEPES, 10 mM $MgCl_2$), and dilution of the test compound and the unlabeled PGE2 was carried out using DMSO and an assay buffer. Further, in the case of the addition of a human serum albumin (HSA), dilution was carried out using an assay buffer containing 4% HSA (final concentration 1%; Sigma). The UniFilter-96 GF/B was treated by preliminarily washing twice with 200 µL/well of a cooled assay buffer. The UniFilter-96 GF/B after filtration was dried in a dryer overnight, 50 µL/well of MicroScint20 (Perkin Elmer) was added thereto, and then the radioactivity was measured using a TopCount (Perkin Elmer). For measurement of the non-specific binding, an unlabeled PGE2 (final concentration 1 µM; Cayman) was added. All of the measurements were carried out in duplicate, and the specific binding amount was determined by subtracting the non-specific binding amount from the total binding amount.

According to Test Example 1 as above, the rat EP4 receptor affinity (Ki) of the compound of the formula (I) was measured. The Ki values of the representative Example compounds of the present invention are shown in Table 1 below.

TABLE 1

| Ex | Ki (nM) |
| --- | --- |
| 2 | 0.92 |
| 22 | 0.53 |
| 23 | 0.43 |
| 25 | 0.66 |
| 26 | 1.6 |
| 31 | 1.1 |
| 32 | 1.3 |
| 36 | 9.8 |
| 50 | 0.78 |
| 55 | 0.92 |
| 57 | 0.72 |
| 60 | 1.1 |
| 76 | 1.8 |
| 83 | 0.52 |
| 87 | 0.82 |
| 92 | 4.6 |
| 93 | 0.79 |
| 119 | 2.1 |
| 120 | 9.8 |
| 159 | 6 |
| 160 | 0.43 |
| 164 | 0.29 |
| 165 | 0.26 |
| 169 | 0.29 |
| 176 | 4 |

Test Example 2: Test to Study the Effect on Urine Albumin in Streptozotocin-induced (STZ) Diabetic Rats.

Eight-week old male Wistar (Crj) rats were divided into groups with unbiased urinary albumin excretion (UAE), and STZ (50 mg/kg) was intravenously administered thereto. From the next day of administration of STZ, the drug was continuously orally administered, and urine was periodically collected in a metabolism cage for 24 hours to measure the UAE. As a result, in a group with drug administration, the UAE inhibitory action was confirmed, and for example, in the case of oral administration of 30 mg/kg of the compound of Example 23, at the fourth week of administration, the group with drug administration showed an UAE inhibition action of 0.9±0.1 mg/day, as compared with that of the vehicle group of 3.1±0.7 mg/day.

Test Example 3: Solubility Test

To 13 µL of a 10 mM DMSO solution of a test material that had been prepared in advance was added exactly 1 mL of a first liquid for a disintegration test of Japanese Pharmacopoeia, followed by shaking at 25° C. for 20 hours, thereby giving a sample stock solution. Next, using a filter impregnated with 200 µL of the sample stock solution, 200 µL of a fresh sample stock solution was added for filtration to obtain a liquid, which was taken as a sample solution. Apart from this, to 10 µL of the 10 mM DMSO solution of the test material was added accurately 1 mL of methanol, followed by stirring, thereby giving a standard solution. 10 µL of the sample solution and the standard solution were tested by liquid chromatography, respectively, and the ratio of the peak area of the sample solution to the peak area of the standard solution was determined, thereby calculating the solubility. For example, the solubilities of the compounds of Examples 23, 25, 31, 32, 50, 55, 57, 60, 93, and 284 were 51 µg/mL, 26 µg/mL, ≧53 µg/mL, 46 µg/mL, 47 µg/mL, ≧52 µg/mL, ≧50 µg/mL, 40 µg/mL, ≧53 µg/mL, and <1 µg/mL, respectively.

As a result of the above-described test, it was confirmed that the compound of the formula (I) exhibited an antagonistic action against an EP4 receptor. Accordingly, it can be used as a therapeutic agent for renal diseases (for example, acute nephritis, recurrent hematuria, persistent hematuria, chronic nephritis, rapidly progressive glomerulonephritis, acute renal insufficiency, chronic renal insufficiency, diabetic nephropathy, Bartter's syndrome, and the like), inflammatory skin diseases (for example, sunburn, burns, eczema, dermatitis, and the like), ischemic heart diseases due to arteriosclerosis (especially, myocardial infarction, angina, and the like), cerebrovascular disorders caused by arteriosclerosis (strokes including stroke and lacunar infarction, cerebral thrombosis, cerebral hemorrhage, subarachnoid hemorrhage, cerebral infarction, and the like), peptic ulcer diseases (gastric ulcer, duodenal ulcer, and the like), metastatic malignancy and metastasis thereof (colon cancer, breast cancer, and the like), and the like, or the analogous diseases in humans and animals, in particular, renal diseases such as chronic renal insufficiency, diabetic nephropathy, and the like.

The compound of the formula (I) or a pharmaceutically acceptable salt thereof is useful as a pharmaceutical preparation having a diuretic effect. Those having a diuretic effect are useful as a therapeutic or prophylactic agent for various types of edema (for example, cardiac edema, cerebral edema, and the like), hypertension such as malignant hypertension, and the like, a premenstrual syndrome, urinary calculus, a poor urine disease caused by an acute or chronic disease, hyperphosphatemia, and the like.

A preparation containing one or two or more kinds of the compound of the formula (I) or a pharmaceutically acceptable salt thereof as an active ingredient can be prepared in accordance with a generally used method, using a pharmaceutically acceptable carrier, excipient, or the like, that is usually used in the art.

The administration can be carried out in any form of oral administration via tablets, pills, capsules, granules, powders, liquid preparations, or the like, or parenteral administration via injections such as intraarticular, intravenous, intramuscular, or other types of injections, suppositories, eye drops, eye ointments, percutaneous liquid preparations, ointments, percutaneous patches, transmucosal liquid preparations, transmucosal patches, inhalations, and the like.

Regarding the solid composition for oral administration according to the present invention, tablets, powders, granules, or the like are used. In such a solid composition, one or two or more kinds of active ingredients are mixed with at least one inert excipient such as lactose, mannitol, glucose, hydroxypropylcellulose, microcrystalline cellulose, starch, polyvinyl pyrrolidone, and/or magnesium aluminometasilicate. According to a conventional method, the composition may contain inert additives such as a lubricant such as magnesium stearate, a disintegrator such as carboxymethylstarch sodium, a stabilizing agent, and a solubilizing aid. As occasion demands, the tablets or the pills may be coated with a film of a sugar coating, or a gastric or enteric coating agent.

The liquid composition for oral administration includes pharmaceutically acceptable emulsions, soluble liquid preparations, suspensions, syrups, elixirs, or the like, and contains a generally used inert diluent such as purified water or ethanol. In addition to the inert diluent, this liquid composition may contain an adjuvant such as a solubilizing agent, a moistening agent, and a suspending agent, a sweetener, a flavor, an aromatic, and an antiseptic.

Injections for parenteral administration include sterile aqueous or non-aqueous soluble liquid preparations, suspensions and emulsions. The aqueous solvent includes, for example, distilled water for injection and physiological saline. Examples of the non-aqueous solvent include propylene glycol, polyethylene glycol, plant oils such as olive oil, alcohols such as ethanol, Polysorbate 80 (Japanese Pharmacopeia), and the like. Such a composition may further contain a tonicity agent, an antiseptic, a moistening agent, an emulsifying agent, a dispersing agent, a stabilizing agent, or a solubilizing aid. These are sterilized, for example, by filtration through a bacteria retaining filter, blending of a bactericide, or irradiation. In addition, these can also be used by preparing a sterile solid composition, and dissolving or suspending it in sterile water or a sterile solvent for injection prior to its use.

The agent for external use includes ointments, plasters, creams, jellies, patches, sprays, lotions, eye drops, eye ointments, and the like. The agents contain generally used ointment bases, lotion bases, aqueous or non-aqueous liquid preparations, suspensions, emulsions, and the like. Examples of the ointment bases or the lotion bases include polyethylene glycol, propylene glycol, white vaseline, bleached bee wax, polyoxyethylene hydrogenated castor oil, glyceryl monostearate, stearyl alcohol, cetyl alcohol, lauromacrogol, sorbitan sesquioleate, and the like.

Regarding the transmucosal agents such as an inhalation, a transnasal agent, and the like, those in the form of a solid, liquid, or semi-solid state are used, and can be prepared in accordance with a conventionally known method. For example, a known excipient, and also a pH adjusting agent, an antiseptic, a surfactant, a lubricant, a stabilizing agent, a thickening agent, or the like may be appropriately added thereto. For their administration, an appropriate device for inhalation or blowing can be used. For example, a compound may be administered alone or as a powder of formulated mixture, or as a solution or suspension in combination with a pharmaceutically acceptable carrier, using a conventionally known device or sprayer, such as a measured administration inhalation device, and the like. The dry powder inhaler or the like may be for single or multiple administration use, and a dry powder or a powder-containing capsule may be used. Alternatively, this may be in a form such as a pressurized aerosol spray which uses an appropriate propellant, for example, a suitable gas such as chlorofluoroalkane, hydrofluoroalkane, carbon dioxide, and the like, or other forms.

In oral administration, the daily dose is generally from about 0.001 to 100 mg/kg, preferably from 0.1 to 30 mg/kg, and more preferably 0.1 to 10 mg/kg, per body weight, administered in one portion or in 2 to 4 divided portions. In the case of intravenous administration, the daily dose is suitably administered from about 0.0001 to 10 mg/kg per body weight, once a day or two or more times a day. In addition, a transmucosal agent is administered at a dose from about 0.001 to 100 mg/kg per body weight, once a day or two or more times a day. The dose is appropriately decided in response to the individual case by taking the symptoms, the age, and the gender, and the like into consideration.

The compound of the formula (I) can be used in combination with various therapeutic or prophylactic agents for the diseases for which the compound of the formula (I) is considered to be effective. The combined preparation may be administered simultaneously, or separately and continuously, or at a desired time interval. The preparations to be co-administered may be a blend, or may be prepared individually.

EXAMPLES

Hereinbelow, the production processes of the compound of the formula (I) are described with reference to the Examples in more detail. The compounds of the formula (I) are not limited to the compounds as described in the Examples below. In addition, the production processes of the starting compounds are shown in the Production Examples.

Production Example 1

To a mixture of methyl (1S,2R)-2-[(tert-butoxycarbonyl)amino]cyclopentanecarboxylate (0.84 g) and ethyl acetate (2.5 ml) was added a 4 M hydrogen chloride/ethyl acetate solution (5.0 ml) under ice-cooling, followed by stirring at room temperature for 2.5 hours. The reaction mixture was concentrated under reduced pressure to obtain methyl (1S,2R)-2-aminocyclopentanecarboxylate hydrochloride (0.72 g).

Production Example 2

To a mixture of methyl 4-(3-methoxy-3-oxopropyl)benzoate (10 g) and sulfuric acid (50 ml) was added dropwise fumed nitric acid (5.7 ml) under ice-cooling, followed by stirring at room temperature for 4 hours. The reaction mixture was poured into ice-water and extracted with chloroform. The organic layer was washed with saturated brine, dried over anhydrous magnesium sulfate, and concentrated under reduced pressure. To the residue were added methanol and concentrated sulfuric acid, followed by stirring at 105° C. for 1 hour. The reaction mixture was concentrated under reduced pressure, and a saturated aqueous sodium hydrogen carbonate solution was added to the residue under ice-cooling. The resulting solid was collected by filtration and washed with a saturated aqueous sodium hydrogen carbonate solution and water to obtain methyl 4-(3-methoxy-3-oxopropyl)-3-nitrobenzoate (12 g).

Production Example 3

The mixture of methyl 4-(3-methoxy-3-oxopropyl)-3-nitrobenzoate (12 g), THF (180 ml), and palladium-carbon (1.2 g) was stirred at room temperature for 4 days under a hydrogen atmosphere. The insolubles of the reaction mixture were separated by filtration through Celite and the filtrate was concentrated under reduced pressure. To the residue were added methanol (100 ml) and p-toluenesulfonic acid monohydrate (0.10 g), followed by heating under reflux for 1 hour, and then allowing to be cooled at room temperature. The reaction mixture was concentrated under reduced pressure. To the residue was added chloroform, followed by washing with a saturated sodium bicarbonate solution and drying over anhydrous magnesium sulfate. The solvent was removed by evaporation under reduced pressure. The residue was washed with methanol to obtain methyl 2-oxo-1,2,3,4-tetrahydroquinoline-7-carboxylate (7.0 g).

Production Example 4

To a mixture of methyl 2-oxo-1,2,3,4-tetrahydroquinoline-7-carboxylate (4.0 g) and DMF (80 ml) was added sodium hydride (0.86 g) under ice-cooling, followed by stirring under ice-cooling for 10 minutes. To a reaction mixture was added allyl bromide (2.9 g) under ice-cooling, followed by stirring at room temperature for 1.5 hours. To the reaction mixture were added ethyl acetate and water. The aqueous layer was separated, followed by extraction with ethyl acetate. The organic layer was combined, washed with water and saturated brine in this order, dried over anhydrous magnesium sulfate, and concentrated under reduced pressure. The residue was purified by silica gel column chromatography (hexane:ethyl acetate=6:1→3:1) to obtain methyl 1-aryl-2-oxo-1,2,3,4-tetrahydroquinoline-7-carboxylate (4.9 g).

Production Example 5

To a mixture of methyl $N^5$-[(benzyloxy)carbonyl]-$N^2$-[(1-methyl-1H-indol-2-yl)carbonyl]-L-ornithinate (13.2 g), THF (65 ml), and methanol (65 ml) was added a 1 M aqueous sodium hydroxide solution (60 ml) under ice-cooling, followed by stirring at room temperature for 3 hours. To the reaction mixture was added 1 M hydrochloric acid (60 ml) under ice-cooling, and the solvent was removed by evaporation under reduced pressure. The residue was stirred at room temperature for 14 hours, and the solid precipitated was collected by filtration and washed with water to obtain $N^5$-[(benzyloxy)carbonyl]-$N^2$-[(1-methyl-1H-indol-2-yl)carbonyl]-L-ornithine (11.6 g).

Production Example 6

To a mixture of (1S,2R)-2-[(tert-butoxycarbonyl)amino]cyclopentanecarboxylic acid (0.88 g) and DMF (8.0 ml) were added cesium carbonate (2.5 g) and methyl iodide (0.82 g) under ice-cooling, followed by stirring at room temperature for 1.5 hours. To the reaction mixture ethyl acetate and water under ice-cooling were added. The organic layer was separated, the aqueous layer was extracted with ethyl acetate (15 ml), and the organic layer was combined and washed with a 10% aqueous citric acid solution, a saturated sodium bicarbonate solution, water, and saturated brine in this order. The organic layer was dried over anhydrous magnesium sulfate and concentrated under reduced pressure to obtain methyl (1S,2R)-2-[(tert-butoxycarbonyl)amino]cyclopentanecarboxylate (0.85 g).

Production Example 7

Methyl (1R,2S)-2-({$N^5$-[(benzyloxy)carbonyl]-$N^2$-(tert-butoxycarbonyl)-L-ornithyl}amino)cyclopentanecarboxylate (11.33 g) was suspended in ethyl acetate (34 ml), and a 4

M hydrogen chloride/ethyl acetate solution (52 ml) was added thereto, followed by stirring at room temperature for 2 hours. The reaction mixture was concentrated under reduced pressure, and to the residue were added ethyl acetate (150 ml) and a saturated sodium bicarbonate solution (150 ml), followed by stirring for 5 minutes and performing a liquid separation operation. The aqueous layer was extracted with ethyl acetate (100 ml), and then the organic layer was combined, washed with saturated brine, and dried over anhydrous magnesium sulfate. The solvent was removed by evaporation under reduced pressure to obtain methyl (1R,2S)-2-({$N^5$-[(benzyloxy)carbonyl]-L-ornithyl}amino)cyclopentanecarboxylate (9.0 g).

Production Example 8

To a mixture of tert-butyl (1R,2S)-2-({$N^5$-[(benzyloxy)carbonyl]-$N^2$-[(9H-fluorene-9-ylmethoxy)carbonyl]-L-ornithyl}amino)cyclopentanecarboxylate (4.0 g) and chloroform(80 ml) was added piperidine (6.0 ml) under ice-cooling, followed by stirring at room temperature for 13 hours. The reaction mixture was washed with a saturated sodium bicarbonate solution, water, and saturated brine in this order, and the organic layer was dried over anhydrous magnesium sulfate. The organic layer was concentrated under reduced pressure and the residue was purified by silica gel column chromatography (hexane:ethyl acetate=1:1, and then 0→2→5% methanol/chloroform) to obtain tert-butyl (1R,2S)-2-({$N^5$-[(benzyloxy)carbonyl]-L-ornithyl}amino)cyclopentanecarboxylate (2.6 g).

Production Example 9

To a mixture of methyl 3-acetyl-1H-indole-6-carboxylate (0.92 g) and DMF (18 ml) was added sodium hydride (0.18 g) under ice-cooling, followed by stirring at room temperature for 0.5 hour. Next, methyl iodide (0.29 ml) was added thereto under ice-cooling, followed by stirring at room temperature for 5 hours. Then, water was added thereto under ice-cooling, followed by stirring at room temperature. The solid precipitated was collected by filtration, washed with water, and purified by silica gel column chromatography (hexane/THF=2:1→chloroform/THF=9:1) to obtain methyl 3-acetyl-1-methyl-1H-indole-6-carboxylate (0.98 g).

Production Example 10

To a mixture of ethyl 5-formyl-4-methyl-1H-pyrrole-2-carboxylate (0.97 g) and DMF (10 ml) was added sodium hydride (0.23 g) under ice-cooling, followed by stirring at room temperature for 0.5 hour. To a reaction mixture was added methyl iodide under ice-cooling, followed by stirring at room temperature for 15 hours. To the reaction mixture was added water under ice-cooling, followed by stirring at room temperature. The solid precipitated was collected by filtration and washed with water to obtain ethyl 5-formyl-1,4-dimethyl-1H-pyrrole-2-carboxylate (1.0 g).

Production Example 11

To a mixture of ethyl 5-formyl-1,4-dimethyl-1H-pyrrole-2-carboxylate (0.99 g) and methanol (10 ml) was added sodium borohydride (0.38 g) under ice-cooling, followed by stirring for 5 minutes under ice-cooling. To a reaction mixture was added a saturated aqueous ammonium chloride solution under ice-cooling, followed by stirring at room temperature for 0.5 hour. To the reaction mixture were added water and ethyl acetate, and the aqueous layer was separated and extracted with ethyl acetate. The organic layer was combined, washed with a saturated sodium bicarbonate solution and saturated brine in this order, dried over anhydrous magnesium sulfate, and concentrated under reduced pressure. The residue was purified by silica gel column chromatography (hexane/ethyl acetate=4:1) to obtain ethyl 5-hydroxymethyl-1,4-dimethyl-1H-pyrrole-2-carboxylate (0.66 g).

Production Example 12

To a mixture of methyl 3-hydroxy benzoate (0.40 g) and DMF (10 ml) were added cesium carbonate (1.2 g) and 2-(2-bromoethoxy)tetrahydro-2H-pyrane (0.60 g), followed by stirring at room temperature over one night. To the reaction mixture were added water and ethyl acetate, and the organic layer was separated, dried over anhydrous magnesium sulfate, and concentrated under reduced pressure. The residue was purified by silica gel column chromatography to obtain methyl 3-[2-(tetrahydro-2H-pyran-2-yloxy)ethoxy]benzoate (0.57 g).

Production Example 13

To a mixture of methyl N-methylindole-6-carboxylate (1.5 g) and acetic acid (22.5 ml) was added sodium cyanoboride (1.62 g), followed by stirring at room temperature for 1 hour. The reaction mixture was poured into ice-water (100 ml), and sodium hydroxide (pellet) was added thereto to adjust the pH to about 10, followed by extraction with ethyl acetate (60 ml). The organic layer was washed with a saturated sodium bicarbonate solution three times, and saturated brine in this order, and dried over anhydrous magnesium sulfate, and the solvent was then removed by evaporation under reduced pressure. The residue was purified by silica gel column chromatography (hexane:ethyl acetate=1:1) to obtain methyl N-methylindoline-6-carboxylate (900 mg) as a pale yellow oily substance.

Production Example 14

A mixture of ethyl 5-hydroxymethyl-1,4-dimethyl-1H-pyrrole-2-carboxylate (2.2 g), ethanol (15 ml), and palladium-carbon (2.2 g) was stirred at room temperature for 2 hours under a hydrogen atmosphere of 3 atmospheres. The insolubles of the reaction mixture were separated by filtration through Celite and the filtrate was concentrated to about 10 ml under reduced pressure. THF (10 ml) was added to the residue, and a 1 M aqueous sodium hydroxide solution (20 ml) was further added at room temperature, followed by stirring at room temperature for 13 days. The reaction mixture was washed with diethyl ether, and 1 M hydrochloric acid (20 ml) was added to the aqueous layer under ice-cooling. The solid precipitated was collected by filtration and washed with water to obtain 1,4,5-trimethyl-1H-pyrrole-2-carboxylic acid (0.79 g).

Production Example 15

A mixture of tert-butyl [(1S,2R)-2-carboxyliccyclopentyl]carbamate (3.0 g), ammonium carbonate (3.77 g), HATU (5.97 g), and DMF (90 ml) was ice-cooled, and DIPEA (8.21 ml) was added thereto, followed by stirring at room temperature over one night. The reaction mixture was diluted with water (200 ml) and extracted twice with ethyl acetate (100 ml). The organic layer was washed with a 1 M aqueous hydrochloric acid, a saturated sodium bicarbonate solution, and saturated brine in this order and dried over anhydrous magnesium sulfate. The solvent was then removed by evaporation under reduced pressure. The residue was washed with hexane (20 ml) to obtain tert-butyl [(1S,2R)-2-carbamoylcyclopentyl]carbamate (2.0 g) as a white solid.

Production Example 16

A mixture of tert-butyl [(1S,2R)-2-carbamoylcyclopentyl]carbamate (500 mg) and DMF (5.0 ml) was ice-cooled, and 2,4,6-trichloro-1,3,5-triazine (404 mg) was added thereto, followed by stirring under ice-cooling for 1 hour, and further at room temperature for 2 hours. To the reaction mixture were added ethyl acetate and a saturated sodium bicarbonate solution, and then liquid-separation was carried out. The aqueous layer was extracted with ethyl acetate, and the combined organic layer was washed with saturated brine, dried over anhydrous magnesium sulfate and then concentrated under reduced pressure. The residue was purified by silica gel column chromatography (hexane:ethyl acetate=3:2) to obtain tert-butyl [(1S,2R)-2-cyanocyclopentyl]carbamate (430 mg) as a white solid.

Production Example 17

To a mixture of ethyl 1-ethyl-4-methyl-1H-pyrrole-2-carboxylate (0.66 g), methanol (5.0 ml), and THF (5.0 ml) was added a 1 M aqueous sodium hydroxide solution (5.0 ml) under ice-cooling, followed by stirring at room temperature for 8.5 days. Water was added to the reaction mixture and the solvent was removed by evaporation under reduced pressure. The residue was washed with diethyl ether, and citric acid was added to the aqueous layer under ice-cooling. The solid precipitated was collected by filtration, washed with water, and dried to obtain 1-ethyl-4-methyl-1H-pyrrole-2-carboxylic acid (0.44 g).

Production Example 18 tert-Butyl [(1S,2R)-2-cyanocyclopentyl]carbamate (415 mg) and hydrochloric acid hydroxylamine (411 mg) were suspended in ethanol (6.2 ml), triethylamine (0.83 ml) was added thereto at room temperature, and the reaction mixture was then stirred at 70° C. for 24 hours. The reaction mixture was left to be cooled, and hydrochloric acid hydroxylamine (411 mg) and triethylamine (0.83 ml) were added thereto, followed by stirring at 75° C. for an additional 48 hours. The reaction mixture was left to be cooled, and water (30 ml) was added thereto, followed by extraction with ethyl acetate (40 ml). The organic layer was washed with a saturated sodium bicarbonate solution and saturated brine in this order and dried over anhydrous magnesium sulfate. The solvent was then removed by evaporation under reduced pressure. The residue was purified by silica gel column chromatography (1.5% methanol-chloroform) to obtain tert-butyl {(1S,2R)-2-[amino(hydroxyimino)methyl]cyclopentyl}carbamate (315 mg) as a white solid.

Production Example 19

To a mixture of 1-(3-tert-butoxy-3-oxopropyl)cyclopentanecarboxylic acid (0.95 g) and toluene (10 ml) were added triethylamine (0.48 g), and diphenylphosphoryl azide (1.2 g) under ice-cooling, followed by stirring at room temperature for 1 hour. The reaction mixture was stirred at 100° C. for 0.5 hour, and then stirred under ice-cooling to give a mixture A. Apart from this, a mixture of DMF (2.0 ml) and benzyl alcohol (0.45 ml) was stirred at room temperature, and sodium hydride (0.18 g) was added thereto, followed by stirring for 0.5 hour to give a mixture B. Next, to the mixture A was added the mixture B under ice-cooling, followed by stirring at room temperature for 1 hour. To the reaction mixture were added ethyl acetate and water, and the aqueous layer was separated and extracted with ethyl acetate. The organic layer was combined, washed with a 10% aqueous citric acid solution, a saturated sodium bicarbonate solution, water, and saturated brine in this order, dried over anhydrous magnesium sulfate, and concentrated under reduced pressure. The residue was purified by silica gel column chromatography (hexane:ethyl acetate=10:1) to obtain tert-butyl 3-(1-{[(benzyloxy)carbonyl]amino}cyclopentyl)propanoate (0.59 g).

Production Example 20

To a mixture of tert-butyl 3-(1-{[(benzyloxy)carbonyl]amino}cyclopentyl)propanoate (0.58 g), dioxane (17 ml), and palladium-carbon (0.12 g) was added 1 M hydrochloric acid (1.7 ml) under ice-cooling, followed by stirring at room temperature for 1 hour under a hydrogen atmosphere. The insolubles in the reaction mixture were separated by filtration through Celite and the filtrate was concentrated under reduced pressure. The residue was washed with diethyl ether to obtain tert-butyl 3-(1-aminocyclopentyl)propanoate (0.11 g).

Production Example 21

To a mixture of ethyl 3-[(tert-butoxycarbonyl)amino]benzoate (3.8 g) and DMF (20 ml) were added 60% sodium hydride (1.1 g) and 2-bromoethylmethyl ether (3.9 g) under ice-cooling, followed by stirring at room temperature over one night. To the reaction mixture were added 60% sodium hydride (0.28 g) and 2-bromoethylmethyl ether (0.98 g), followed by stirring at room temperature for 6 hours. Water and ethyl acetate were added thereto, and the organic layer was then separated, washed with 1 M hydrochloric acid and saturated brine in this order, dried over anhydrous magnesium sulfate, and concentrated under reduced pressure. The residue was purified by silica gel column chromatography to obtain ethyl 3-[(tert-butoxycarbonyl)(2-methoxyethyl)amino]benzoate (2.7 g).

Production Example 22

To a mixture of 4-methoxybenzyl (1R,2S)-2-[(tert-butoxycarbonyl)amino]cyclopentanecarboxylate (2.2 g) and methanol (11 ml) was added p-toluene sulfonic acid hydrate (1.2 g) at room temperature, followed by stirring at 40° C. for 13 hours. Further, p-toluene sulfonic acid hydrate (0.24 g) was added thereto, followed by stirring at 40° C. for 3 hours. The reaction mixture was concentrated under reduced pressure, and 1 M hydrochloric acid and diethyl ether were added to the residue. The aqueous layer was separated, and the organic layer was extracted with 1 M hydrochloric acid. The aqueous layer was combined, and sodium hydrogen carbonate was added thereto under ice-cooling to adjust the pH to about 7. The reaction mixture was extracted with ethyl acetate and washed with saturated brine. The organic layer was dried over anhydrous magnesium sulfate and concentrated under reduced pressure to obtain 4-methoxybenzyl (1R,2S)-2-aminocyclopentanecarboxylate (1.1 g).

Production Example 23

A mixture of tert-butyl [(1S,2R)-2-cyanocyclopentyl]carbamate (2.8 g), toluene (50 ml), sodium azide (2.1 g), and triethylamine hydrochloride (4.5 g) was stirred at 130° C. for 24 hours. To the reaction mixture was added water (40 ml) at room temperature. The aqueous layer was separated, citric acid was added thereto under ice-cooling, and the solid precipitated was collected by filtration and washed with water to obtain tert-butyl [(1S,2R)-2-(2H-tetrazole-5-yl)cyclopentyl] carbamate (3.0 g).

Production Example 24

To a mixture of 4-methoxybenzyl (1R,2S)-2-({$N^5$-[(benzyloxy)carbonyl]-$N^2$-(tert-butoxycarbonyl)-L-ornithyl}amino)cyclopentanecarboxylate (2.5 g) and methanol (25 ml) was added p-toluene sulfonic acid hydrate (1.2 g) at room temperature, followed by stirring at 40° C. for 24 hours. The reaction mixture was concentrated under reduced pressure, and ethyl acetate and water were added to the residue. Sodium hydrogen carbonate was added thereto under ice-cooling to adjust the pH to about 8, and the organic layer was separated. The aqueous layer was extracted with ethyl acetate (50 ml), and the organic layer was combined and extracted with a 10% aqueous citric acid solution. To the aqueous layer was added sodium hydrogen carbonate under ice-cooling to adjust the pH to about 8, followed by extraction with ethyl acetate and washing with saturated brine. The organic layer was dried over anhydrous magnesium sulfate and concentrated under reduced pressure to obtain 4-methoxybenzyl (1R,2S)-2-({$N^5$-[(benzyloxy)carbonyl]-L-ornithyl}amino)cyclopentanecarboxylate (1.6 g).

Production Example 25

A mixture of tert-butyl [(1S,2R)-2-{amino[({[(2-ethyl hexyl)oxy]carbonyl}oxy)imino]methyl}cyclopentyl]carbamate (492 mg) and xylene (10 ml) was stirred at an outside temperature of 140° C. for 4 hours. The reaction mixture was left to be cooled, ethyl acetate (40 ml) was added, followed by washing with saturated brine. The organic layer was dried over anhydrous magnesium sulfate and the solvent was then removed by evaporation under reduced pressure. The residue was purified by silica gel column chromatography (1% methanol-chloroform) to obtain tert-butyl [(1S,2R)-2-(5-oxo-4,5-dihydro-1,2,4-oxadiazol-3-yl)cyclopentyl]carbamate (328 mg) as a pale yellow solid.

Production Example 26

To a mixture of sodium hydride (522 mg) and DMF (30 ml) was added methyl 1H-indazole-4-carboxylate (2.0 g) under ice-cooling, followed by stirring for 20 minutes. To the reaction mixture was added methyl iodide (1.41 ml), followed by stirring under ice-cooling for 30 minutes, and further at room temperature for 1 hour. The reaction mixture was ice-cooled, and water (100 ml) was added thereto, followed by stirring for 15 minutes. The insolubles were removed by filtration and the filtrate was extracted with ethyl acetate (80 ml). The organic layer was washed with a saturated sodium bicarbonate solution and saturated brine in this order and dried over anhydrous magnesium sulfate. The solvent was then removed by evaporation under reduced pressure. The residue was purified by silica gel column chromatography (hexane:ethyl acetate=3: 1→1:1) to obtain methyl 1-methyl-1H-indazole-4-carboxylate (900 mg) as a pale yellow solid and methyl 2-methyl-2H-indazole-4-carboxylate (600 mg) as a pale red oil.

Production Example 27

To a mixture of benzyl [(1S,2S)-2-hydroxycyclopentyl] carbamate (1.3 g) and benzene (13 ml) were added, tert-butyl bromoacetate (3.2 g), hydrogen tetrabutyl ammonium sulfate (0.46 g), and a 50% aqueous NaOH solution (13 ml) under ice-cooling, followed by stirring under ice-cooling for 1 hour and further at room temperature for 2 hours. The reaction mixture was poured into ice-water, extracted with ethyl acetate, then washed with water and saturated brine in this order, dried over anhydrous magnesium sulfate, and concentrated under reduced pressure. The residue was purified by silica gel column chromatography (hexane:ethyl acetate=10: 1→7:1→5:1) to obtain tert-butyl {[(1S,2S)-2-{[(benzyloxy) carbonyl]amino}cyclopentyl]oxy}acetate (1.3 g).

Production Example 28

To a mixture of tert-butyl {[(1S,2S)-2-{[(benzyloxy)carbonyl]amino}cyclopentyl]oxy}acetic acid (1.3 g), ethanol (13 ml), and palladium-carbon (0.30 g) was added 1 M hydrochloric acid (3.7 ml) under ice-cooling, followed by stirring at room temperature for 4 hours under a hydrogen atmosphere. The insolubles in the reaction mixture were separated by filtration through Celite and the filtrate was concentrated under reduced pressure. The residue was washed with diethyl ether to obtain tert-butyl {[(1S,2S)-2-aminocyclopentyl] oxy}acetate hydrochloride (0.89 g).

Production Example 29

To a mixture of 3-[(tert-butoxycarbonyl)(2-methoxyethyl) amino]benzoic acid (0.57 g) and ethyl acetate (10 ml) was added a 4 M hydrogen chloride/ethyl acetate solution (5.0 ml) under ice-cooling, followed by stirring at room temperature over one night. The solid precipitated was collected by filtration to obtain 3-[(2-methoxyethyl)amino]benzoic acid hydrochloride (0.38 g).

Production Example 30

To a mixture of tert-butyl {(1S,2R)-2-[amino(hydroxyimino)methyl]cyclopentyl}carbamate (320 mg) and acetonitrile (8.0 ml) were added 1,1'-carbonothioyl bis(1H-imidazole) (391 mg) and DBU (787 µl) in this order, followed by stirring at room temperature for 1 hour. The reaction mixture was diluted with water (15 ml), and 1 M hydrochloric acid was added thereto to adjust the pH to about 4, followed by extraction with ethyl acetate (40 ml). The organic layer was washed with saturated brine and dried over anhydrous magnesium sulfate, and the solvent was then removed by evaporation under reduced pressure. The residue was purified by silica gel column chromatography (3% methanol-chloroform) and then washed with cooled ethyl acetate (2 ml) to obtain tert-butyl [(1S,2R)-2-(5-thioxo-4,5-dihydro-1,2,4-oxadiazol-3-yl)cyclopentyl]carbamate (160 mg) as a white solid.

Production Example 31

A mixture of tert-butyl {(1S,2R)-2-[amino(hydroxyimino) methyl]cyclopentyl}carbamate (350 mg) and methylene chloride (3.5 ml) was ice-cooled, and pyridine (291 µl) was added thereto, and then a solution of thionyl chloride (131 µl) in methylene chloride (3.5 ml) was added thereto, followed by stirring at the same temperature for 1 hour and 30 minutes. The reaction mixture was concentrated under reduced pressure, and water (30 ml) and ethyl acetate (40 ml) were added to the residue, followed by liquid separation. The organic layer was washed with 1 M hydrochloric acid and saturated brine in this order and dried over anhydrous magnesium sulfate. The solvent was then removed by evaporation under reduced pressure. The residue was purified by silica gel column chromatography (0.5% methanol-chloroform) to obtain tert-butyl [(1S,2R)-2-(2-oxide-3H-1,2,3,5-oxathiadiazol-4-yl)cyclopentyl]carbamate (230 mg) as a white solid.

Production Example 32

A mixture of tert-butyl [(1S,2R)-2-carboxyliccyclopentyl]carbamate (1.03 g) and DMF (15.5 ml) was ice-cooled and CDI(947 mg) was added thereto, followed by stirring at the same temperature for 2 hours. To the reaction mixture was added hydrazine hydrate (900 mg), followed by stirring at the same temperature for 1 hour and further at room temperature for 2 hours. The reaction mixture was diluted with water (50 ml) and a saturated sodium bicarbonate solution (50 ml), and extracted three times with ethyl acetate (80 ml). The organic layer was washed with saturated brine and dried over anhydrous magnesium sulfate, and the solvent was then removed by evaporation under reduced pressure. The residue was washed with diisopropyl ether (10 ml) to obtain tert-butyl [(1S,2R)-2-(hydrazinocarbonyl)cyclopentyl]carbamate (800 mg) as a white solid.

Production Example 33

A mixture of tert-butyl [(1S,2R)-2-(hydrazinocarbonyl)cyclopentyl]carbamate (370 mg) and ethanol (5.6 ml) was ice-cooled, and dithioxomethane (230 μl) and potassium hydroxide (120 mg) were added thereto in this order, followed by stirring at the same temperature for 30 minutes. The reaction mixture was stirred at room temperature for 1 hour, warmed, and heated for 6 hours under reflux. The reaction mixture was left to be cooled, and water (50 ml) and diethyl ether (50 ml) were added thereto, followed by liquid separation. The aqueous layer was ice-cooled, and 1 M hydrochloric acid was added thereto to adjust the pH to about 4, followed by extraction with ethyl acetate (50 ml). The organic layer was washed with saturated brine, dried over anhydrous magnesium sulfate, and then concentrated under reduced pressure. The residue was washed with diisopropyl ether (5 ml) to obtain tert-butyl [(1S,2R)-2-(5-thioxo-4,5-dihydro-1,3,4-oxadiazol-2-yl)cyclopentyl]carbamate (308 mg) as a white solid.

Production Example 34

To a mixture of tert-butyl [(1S,2R)-2-(hydrazinocarbonyl)cyclopentyl]carbamate (400 mg) and THF (12 ml) were added N-methylisothiocyanate (146 μl) and DBU (738 μl) in this order, followed by stirring at 65° C. for 10 hours. The reaction mixture was concentrated under reduced pressure, and water (50 ml) was added to the residue, followed by washing with diethyl ether. The aqueous layer was adjusted to a pH of about 4 with 1 M hydrochloric acid and extracted with ethyl acetate (50 ml). The organic layer was washed with saturated brine, dried over magnesium sulfate, and then concentrated under reduced pressure. The residue was purified by silica gel column chromatography (1% methanol-chloroform) and then washed with diisopropyl ether (3 ml) to obtain tert-butyl [(1S,2R)-2-(4-methyl-5-thioxo-4,5-dihydro-1H-1,2,4-triazol-3-yl)cyclopentyl]carbamate (320 mg) as a white solid.

Production Example 35

To a mixture of tert-butyl {(1 S,2R)-2-[amino(hydroxyimino)methyl]cyclopentyl}carbamate (415 mg) and THF (8.3 ml) was added 1,1'-carbonothionyl bis(1H-imidazole) (507 mg), followed by stirring at room temperature for 1 hour. The reaction mixture was diluted with water (25 ml) and extracted with ethyl acetate (40 ml). The organic layer was washed with water and dried over anhydrous magnesium sulfate, and the solvent was then removed by evaporation under reduced pressure. The residue was dissolved in THF (8.3 ml), and a boron trifluoride/diethyl ether complex (1.21 g) was added thereto, followed by stirring at room temperature for 8 hours. The reaction mixture was diluted with water (40 ml) and extracted with ethyl acetate (40 ml). The organic layer was washed with 1 M hydrochloric acid and saturated brine in this order, dried over anhydrous magnesium sulfate, and then concentrated under reduced pressure. The residue was purified by silica gel column chromatography (0.4% methanol-chloroform) to obtain tert-butyl [(1S,2R)-2-(5-oxo-4,5-dihydro-1,2,4-thiadiazol-3-yl)cyclopentyl]carbamate (62 mg) as a white solid and tert-butyl [(1S,2S)-2-(5-oxo-4,5-dihydro-1,2,4-thiadiazol-3-yl)cyclopentyl]carbamate (103 mg) as a white solid.

Production Example 36

To a mixture of rel-(1R,2S)-2-(methoxycarbonyl)cyclobutanecarboxylic acid (1.3 g) and acetone (15 ml) were added triethylamine (1.7 ml) and ethyl chloroformate (1.1 ml) at −10° C., followed by stirring under ice-cooling for 2 hours. To a reaction mixture was added an aqueous solution (3.3 ml) of sodium azide (1.1 g) under ice-cooling, followed by stirring at room temperature for 4 hours. To the reaction mixture were added water and diethyl ether, and the aqueous layer was then extracted with diethyl ether. The organic layer was combined and washed with a 10% aqueous citric acid solution, a saturated sodium bicarbonate solution, water, and saturated brine in this order, dried over anhydrous magnesium sulfate, and concentrated under reduced pressure. To the residue were added toluene (20 ml) and benzyl alcohol (2.5 ml), followed by stirring at 130° C. for 21 hours. The reaction mixture was concentrated under reduced pressure and the residue was purified by silica gel column chromatography (hexane:ethyl acetate=5:1→4:1). To the purified product thus obtained was added pyridine (15 ml), and further added anhydrous acetic acid (3.0 ml) under ice-cooling, followed by stirring at room temperature for 1 hour. The reaction mixture was concentrated under reduced pressure, and a saturated sodium bicarbonate solution was added to the residue, followed by stirring. To the reaction mixture were added ethyl acetate and water, and the aqueous layer was separated and extracted with ethyl acetate. The organic layer was combined and washed with a 10% aqueous citric acid solution, a saturated sodium bicarbonate solution, water, and saturated brine in this order, dried over anhydrous magnesium sulfate, and concentrated under reduced pressure. The residue was purified by silica gel column chromatography (hexane:ethyl acetate=8:1→5:1→4:1) to obtain methyl rel-(1R,2S)-2-{[(benzyloxy)carbonyl]amino}cyclobutanecarboxylate (1.1 g).

Production Example 37

A mixture of rel-(1R,5S)-3-oxabicyclo[3.1.0]hexane-2,4-dione (1.1 g) and 2-methyl-2-propanol (10 ml) was stirred at 110° C. for 2.5 days. The reaction mixture was concentrated under reduced pressure to obtain rel-(1R,2S)-2-(tert-butoxycarbonyl)cyclopropanecarboxylic acid (1.8 g).

Production Example 38

To a mixture of rel-(1R,2S)-2-(tert-butoxycarbonyl)cyclopropanecarboxylic acid (1.8 g) and acetone (21 ml) were added triethylamine (2.0 ml) and ethyl chloroformate (1.3 ml) at −10° C., followed by stirring at −10° C. for 3 hours. To the reaction mixture was added an aqueous solution (7.0 ml) of sodium azide (1.3 g), followed by stirring at room temperature for 4 hours. To the reaction mixture were added water and diethyl ether, and then the aqueous layer was separated and extracted with diethyl ether. The organic layer was combined and washed with a 10% aqueous citric acid solution, a saturated sodium bicarbonate solution, water, and saturated brine in this order, dried over anhydrous magnesium sulfate, and concentrated under reduced pressure. To the residue were added toluene (13 ml) and 2-methyl-2-propanol (9.2 ml), followed by stirring at 110° C. for 13 hours. The reaction mixture was concentrated under reduced pressure and the residue was purified by silica gel column chromatography (hexane:ethyl acetate=20:1→15:1) to obtain tert-butyl rel-(1R,2S)-2-[(tert-butoxycarbonyl)amino]cyclopropanecarboxylate (0.55 g).

Production Example 39

To a mixture of methyl $N^5$-[(benzyloxy)carbonyl]-L-ornithinate hydrochloride, DMF (100 ml), 1-methyl-1H-indol-2-carboxylic acid (5.6 g), and HOBt (4.5 g) was added WSC (5.2 g) under ice-cooling, followed by stirring at room temperature for 19 hours. To the reaction mixture were added water (200 mL) and ethyl acetate under ice-cooling, followed by thorough stirring. The solid precipitated was collected by filtration and washed with water. The obtained solid was suspended in a 50% aqueous ethanol solution (60 ml), stirred, then collected by filtration, and washed with a 50% aqueous ethanol solution to obtain methyl $N^5$-[(benzyloxy)carbonyl]-$N^2$-[(1-methyl-1H-indol-2-yl]-L-ornithinate (13.2 g).

Production Example 40

To a mixture of tert-butyl (1R,2S)-2-({$N^5$-[(benzyloxy)carbonyl]-$N^2$-[(1-methyl-1H-indol-2-yl)carbonyl]-L-ornithyl}amino)cyclopentanecarboxylate (3.0 g), methanol (50 ml), and THF (50 ml) were added 1 M hydrochloric acid (5.1 ml) and palladium-carbon (5.4 g) under ice-cooling, followed by stirring at room temperature for 3 hours under a hydrogen atmosphere. The insolubles of the reaction mixture were separated by filtration through Celite and the filtrate was concentrated under reduced pressure to obtain tert-butyl (1R,2S)-2-({$N^2$-[(1-methyl-1H-indol-2-yl)carbonyl]-L-ornithyl}amino)cyclopentanecarboxylate hydrochloride (2.6 g).

Production Example 42

A mixture of benzyl [(1S,2S)-2-(cyanomethoxy)cyclopentyl]carbamate (0.44 g), toluene (10 mL), sodium azide (0.26 mg), and triethylamine hydrochloride (0.55 g) was stirred at 130° C. for 8 hours. To the reaction mixture was added water, followed by washing with ethyl acetate. The aqueous layer was added with citric acid, followed by extraction with ethyl acetate. Then, it was dried over anhydrous magnesium sulfate, and concentrated under reduced pressure. The residue was purified by silica gel column chromatography to obtain benzyl [(1S,2S)-2-(1H-tetrazole-5-ylmethoxy)cyclopentyl]carbamate (0.22 g).

Production Example 43

A mixture of (1R,2S)-2-[(tert-butoxycarbonyl)amino]cyclopentanecarboxylic acid (1.0 g), DMF (10 ml), 3-(amino-sulfonyl)propylacetic acid (0.95 ml), CDI(0.85 g), and DBU (0.80 g) was stirred at room temperature for 3 days. To the reaction mixture were added 1 M hydrochloric acid and ethyl acetate, and the organic layer was separated. The organic layer was washed with a saturated sodium bicarbonate solution, then dried over anhydrous magnesium sulfate, and concentrated under reduced pressure to obtain 3-{[({(1R,2S)-2-[(tert-butoxycarbonyl)amino]cyclopentyl}carbonyl)amino]sulfonyl}propylacetic acid (1.2 g).

Production Example 44

To a mixture of 3-{[({(1R,2S)-2-[(tert-butoxycarbonyl)amino]cyclopentyl}carbonyl)amino]sulfonyl}propylacetic acid (1.2 g) and methanol (12 ml) was added a 4 M hydrogen chloride/ethyl acetate solution (6.0 ml) under ice-cooling, followed by stirring at room temperature over one night. The reaction mixture was concentrated under reduced pressure to obtain (1R,2S)-2-amino-N-[(3-hydroxypropyl)sulfonyl]cyclopentane carboxamide hydrochloride (1.1 g).

The compounds of Production Examples 45, 58, 59, 61, 75, 78, 84, 85, 88, and 89 were prepared in the same manner as in the method of Production Example 1, the compound of Production Example 52 was prepared in the same manner as in the method of Production Example 5, the compounds of Production Examples 46, 56, 57, 60, and 73 were prepared in the same manner as in the method of Production Example 6, the compounds of Production Examples 50, 63, 77, 83, and 91 were prepared in the same manner as in the method of Production Example 7, the compounds of Production Examples 53 and 67 were prepared in the same manner as in the method of Production Example 10, the compounds of Production Examples 47, 54, 64, 65, 66, 70, 71, 72, 80, and 81 were prepared in the same manner as in the method of Production Example 17, the compounds of Production Examples 48, 49, 55, 62, 74, 76, 82, and 90 were prepared in the same manner as in the method of Example 1, the compounds of Production Examples 68, 69, and 79 were prepared in the same manner as in the method of Production Example 26, the compounds of Production Examples 41 and 86 were synthesized in the same manner as in the method of Production Example 27, the compound of Production Example 87 was synthesized in the same manner as in the method of Production Example 28, the compound of Production Example 92 was prepared in the same manner as in the method of Production Example 37, and the compound of Production Example 51 was prepared in the same manner as in the method of Production Example 39. The structures and the physicochemical data of the compounds of Production Examples are shown in Tables 2 to 12.

Example 1

Production Process A1

To a mixture of tert-butyl (1R,2S)-2-aminocyclopentanecarboxylate (0.21 g), DMF (4.0 ml), and $N^5$-[(benzyloxy)carbonyl]-$N^2$-[(1-methyl-1H-indol-2-yl)carbonyl]-L-ornithine (0.40 g) were added HATU (0.40 g) and diisopropylethylamine (0.27 g) under ice-cooling, followed by stirring at room temperature for 11 hours. To the reaction mixture were added ethyl acetate and water under ice-cooling, the organic layer was separated, and the aqueous layer was extracted with ethyl acetate. The organic layer was combined and washed with a 10% aqueous citric acid solution, a saturated sodium bicarbonate solution, water, and saturated brine in this order. The organic layer was dried over anhydrous magnesium sulfate and concentrated under reduced pressure. The residue was purified by silica gel column chromatography (hexane:THF=5:2→2:1) to obtain tert-butyl (1R,2S)-2-({$N^5$-[(benzyloxy)carbonyl]-$N^2$-[(1-methyl-1H-indol-2-yl)carbonyl]-L-ornithyl}amino)cyclopentanecarboxylate (0.41 g).

Example 2

Production Process B1

To a mixture of tert-butyl (1R,2S)-2-({$N^5$-[(benzyloxy)carbonyl]-$N^2$-[(1-methyl-1H-indol-2-yl)carbonyl]-L-ornithyl}amino)cyclopentanecarboxylate (0.40 g) and chloroform (10 ml) was added a 4 M hydrogen chloride/ethyl acetate solution (20 ml) under ice-cooling, followed by stirring at room temperature for 3 hours. The reaction mixture was concentrated under reduced pressure, and to the residue were added ethyl acetate and water. The aqueous layer was separated, and the organic layer was washed with saturated brine and dried over anhydrous magnesium sulfate. The organic layer was concentrated under reduced pressure, and diethyl ether was added to the residue for solidification, followed by washing with diethyl ether and a 50% aqueous methanol solution. Further, it was purified by silica gel column chromatography (0→2% MeOH/chloroform), and the obtained solid was washed with a 50% aqueous methanol solution to obtain (1R,2S)-2-({$N^5$-[(benzyloxy)carbonyl]-$N^2$-[(1-methyl-1H-indol-2-yl)carbonyl]-L-ornithyl}amino)cyclopentanecarboxylic acid (0.25 g).

Example 3

Production Process B2

To a mixture of methyl (1S,2R)-2-({$N^5$-[(benzyloxy)carbonyl]-$N^2$-[(1-methyl-1H-indol-2-yl)carbonyl]-L-ornithyl}amino)cyclopentanecarboxylate (0.25 g), THF (2.0 ml), and methanol (2.0 ml) was added a 1 M aqueous sodium hydroxide solution (2.0 ml) under ice-cooling, followed by stirring at room temperature for 5 hours. To the reaction mixture was added 1 M hydrochloric acid (2.0 ml) under ice-cooling, followed by stirring at room temperature. The solid precipitated was collected by filtration and washed with water to obtain (1S,2R)-2-({$N^5$-[(benzyloxy)carbonyl]-$N^2$-[(1-methyl-1H-indol-2-yl)carbonyl]-L-ornithyl}amino)cyclopentanecarboxylic acid (0.22 g).

Example 4

Production Process D1

To a mixture of 2-oxo-2-phenylethyl (1R,2S)-2-({$N^5$-[(benzyloxy)carbonyl]-$N^2$-[(1,4,5-trimethyl-1H-pyrrol-2-yl)carbonyl]-L-ornithyl}amino)cyclopentanecarboxylate (0.30 g) and DMF (3.0 ml) were added zinc (0.61 g) and acetic acid (3.0 ml) under ice-cooling, followed by stirring at room temperature for 6 hours. To the reaction mixture was added ethyl acetate and the insolubles were separated by filtration through Celite. The filtrate was concentrated under reduced pressure, and a 1 M aqueous sodium hydroxide solution was added to the residue, followed by washing with diethyl ether. Citric acid was added thereto under ice-cooling, and the solid precipitated was collected by filtration and washed with water to obtain (1R,2S)-2-({$N^5$-[(benzyloxy)carbonyl]-$N^2$-[(1,4,5-trimethyl-1H-pyrrol-2-yl)carbonyl]-L-ornithyl}amino)cyclopentanecarboxylic acid (0.19 g).

Example 5

Production Process H

To a mixture of 4-methoxybenzyl (1R,2S)-2-({$N^5$-[(benzyloxy)carbonyl]-$N^2$-[(1,3-dimethyl-1H-pyrazole-5-yl)carbonyl]-L-ornithyl}amino)cyclopentanecarboxylate (0.50 g) and methylene chloride (5.0 ml) was added trifluoroacetic acid (5.0 ml) under ice-cooling, followed by stirring for 1 hour under ice-cooling. The reaction mixture was concentrated under reduced pressure, and diethyl ether and a saturated sodium bicarbonate solution were added to the residue. The organic layer was separated, the aqueous layer was then washed with diethyl ether, and citric acid was added thereto under ice-cooling. The solid precipitated was collected by filtration, washed with water, then purified by silica gel column chromatography (5% methanol/chloroform), solidified with a 50% aqueous ethanol solution, and washed to obtain (1R,2S)-2-({$N^5$-[(benzyloxy)carbonyl]-$N^2$-[(1,3-dimethyl-1H-pyrazole-5-yl)carbonyl]-L-ornithyl}amino)cyclopentanecarboxylic acid (37 mg).

Example 6

Production Process F

To a mixture of tert-butyl (1R,2S)-2-({$N^5$-[(benzyloxy)carbonyl]-L-ornithyl}amino)cyclopentanecarboxylate (0.40 g) and DMF (11 ml) were added 8-quinolinecarboaldehyde (0.16 g) and sodium borohydride (0.35 g) under ice-cooling, followed by stirring at room temperature over one night. To the reaction mixture was added water, followed by neutralization with a saturated sodium bicarbonate solution and extraction with ethyl acetate. The organic layer was dried over anhydrous magnesium sulfate and concentrated under reduced pressure. The residue was purified by silica gel column chromatography (chloroform:ethyl acetate=4/1-1/1). To the purified product thus obtained was added THF (6.0 ml), and added di-tert-butyl dicarbonate (0.14 g) and sodium hydrogen carbonate (53 mg) at room temperature, followed by stirring at room temperature over one night. Water was added to the reaction mixture, followed by extraction with ethyl acetate. The organic layer was dried over anhydrous magnesium sulfate and concentrated under reduced pressure. The residue was purified by silica gel column chromatography (hexane/ethyl acetate=3:1→1:1). To the product was added ethyl acetate (4.0 ml), and further added a 4 M hydrogen chloride/ethyl acetate solution (4.0 ml) under ice-cooling, followed by stirring at room temperature over one night. The reaction mixture was concentrated under reduced pressure, and a saturated sodium bicarbonate solution was added to the residue to adjust the pH to about 7, followed by extraction with a solution of 2-propanol:chloroform at 1:3. The organic layer was dried over anhydrous magnesium sulfate and concentrated under reduced pressure. To the residue were added ethyl acetate and a 4 M hydrogen chloride/ethyl acetate solution, and the precipitated crystals were collected by filtration and washed with ethyl acetate to obtain (1R,2S)-2-({$N^5$-[(benzyloxy)carbonyl]-$N^2$-(quinoline-8-ylmethyl)-L-ornithyl}amino)cyclopentanecarboxylic acid dihydrochloride (66 mg).

Example 7

Production Process G

To a mixture of 2-oxo-2-phenylethyl (1R,2S)-2-({$N^5$-[(benzyloxy)carbonyl]-L-ornithyl}amino)cyclopentanecarboxylate hydrochloride (0.30 g) and methylene chloride (6.0 ml) were added 4-chlorobenzaldehyde (87 mg), sodium acetate (53 mg), and sodium borohydride (215 mg) at room temperature, followed by stirring at room temperature over one night. To a reaction mixture was added a saturated sodium bicarbonate solution under ice-cooling to adjust the pH to about 7, followed by extraction with ethyl acetate. The organic layer was dried over anhydrous magnesium sulfate and concentrated under reduced pressure. The residue was purified by silica gel column chromatography to obtain 2-oxo-2-phenylethyl (1R,2S)-2-({$N^5$-[(benzyloxy)carbonyl]-$N^2$-(4-chlorobenzyl)-L-ornithyl}amino)cyclopentanecarboxylate (0.34 g).

Example 8

Production Process D2

To a mixture of 2-oxo-2-phenylethyl (1R,2S)-2-({$N^5$-[(benzyloxy)carbonyl]-$N^2$-(4-chlorobenzyl)-L-ornithyl}amino)cyclopentanecarboxylate (0.24 g), acetic acid (2.4 ml), and DMF (2.4 ml) was added zinc (0.50 g) under ice-cooling, followed by stirring at room temperature for 6 hours. To the reaction mixture were added ethyl acetate and the insolubles were separated by filtration through Celite. The filtrate was concentrated under reduced pressure, and a 1 M aqueous sodium hydroxide solution was added to the residue, followed by washing with diethyl ether. Citric acid was added o the aqueous layer to adjust the pH to about 6 and the solid precipitated was collected by filtration to obtain sodium (1R,2S)-2-({$N^5$-[(benzyloxy)carbonyl]-$N^2$-(4-chlorobenzyl)-L-ornithyl}amino)cyclopentanecarboxylate (111 mg).

Example 9

Production Process B3

To a mixture of methyl (1R,2S)-2-({$N^2$-(3-acetoxybenzoyl)-$N^5$-[(benzyloxy)carbonyl]-L-ornithyl}amino)cyclopentanecarboxylate (0.35 g), methanol (3.0 ml), and THF (3.0 ml) was added a 1 M aqueous sodium hydroxide solution (1.9 ml) under ice-cooling, followed by stirring at room temperature over one night. Further, to the reaction mixture were added a 1 M aqueous sodium hydroxide solution (1.0 ml) under ice-cooling, followed by stirring at room temperature for 4 hours. After completion of the reaction, 1 M hydrochloric acid was added thereto under ice-cooling, followed by extraction with ethyl acetate. The organic layer was dried over anhydrous magnesium sulfate and concentrated under reduced pressure. The residue was purified by silica gel column chromatography, and diisopropyl ether and ethyl acetate were added to the purified product obtained to give a solid. The solid was collected by filtration to obtain (1R,2S)-2-({$N^5$-[(benzyloxy)carbonyl]-$N^2$-(3-hydroxybenzoyl)-L-ornithyl}amino)cyclopentanecarboxylic acid (0.12 g).

Example 10

Production Process I

To a mixture of methyl (1R,2S)-2-[($N^5$-[(benzyloxy)carbonyl]-$N^2$-{3-[2-(tetrahydro-2H-pyran-2-yloxy)ethoxy]benzoyl}-L-ornithyl)amino]cyclopentanecarboxylate (0.64 g), methanol (10 ml), and methylene chloride (6.0 ml) was added p-toluenesulfonic acid monohydrate (0.22 g) under ice-cooling, followed by stirring at room temperature over one night. The reaction mixture was concentrated under reduced pressure, and ethyl acetate was added to the residue, followed by washing with water. The organic layer was dried over anhydrous magnesium sulfate and concentrated under reduced pressure. The residue was purified by silica gel column chromatography to obtain methyl (1R,2S)-2-({$N^5$-[(benzyloxy)carbonyl]-$N^2$-[3-(2-hydroxyethoxy)benzoyl]-L-ornithyl}amino)cyclopentanecarboxylate (0.39 g).

Example 11

Production Process D3

2-Oxo-2-phenylethyl (1R,2S)-2-({$N^5$-[(benzyloxy)carbonyl]-$N^2$-[(2E)-3-pyridin-2-ylpro-2-penoyl]-L-ornithyl}amino)cyclopentanecarboxylate (0.40 g) was treated in the same manner as in Example 4 (Production Process D1) to obtain (1R,2S)-2-({$N^5$-[(benzyloxy)carbonyl]-$N^2$-(3-pyridin-2-ylpropanoyl)-L-ornithyl}amino)cyclopentanecarboxylic acid (0.21 g).

Example 12 and Example 115

Production Process S

To a mixture of methyl rel-(1R,2S)-2-({$N^5$-[(benzyloxy)carbonyl]-$N^2$-[(1-methyl-1H-indol-2-yl)carbonyl]-L-ornithyl}amino)cyclobutanecarboxylate (0.44 g), methanol (12 ml), THF (12 ml), and water (8.0 ml) was added potassium carbonate (0.57 mg) under ice-cooling, followed by stirring at room temperature for 18 hours. The reaction mixture was concentrated under reduced pressure, and diethyl ether and water were added to the residue. The insolubles were separated by filtration, and the organic layer was then separated. To the aqueous layer was added 1 M hydrochloric acid (8.2 ml) under ice-cooling, followed by extraction with chloroform. The organic layer was washed with saturated brine (40 ml). The organic layer was dried over anhydrous magnesium sulfate, concentrated under reduced pressure, and purified by silica gel column chromatography (1→2% methanol/chloroform) to obtain a low polarity component and a high polarity component, which were each washed with a 50% aqueous ethanol solution for solidification. Thus, the low polarity component (Example 12, 86 mg) and the high polarity component (Example 155, 92 mg) were obtained, respectively.

Example 13

Production Process B4

To a mixture of tert-butyl (1R,2S)-2-({$N^5$-[(benzyloxy)carbonyl]-$N^2$-[(2E)-3-pyridin-2-ylpro-2-penoyl]-L-ornithyl}amino)cyclopentanecarboxylate (0.34 g) and ethyl acetate (4.0 ml) were added a 4 M hydrogen chloride/ethyl acetate solution (6.0 ml) and 4 M hydrogen chloride/dioxane solution (4.0 ml) under ice-cooling, followed by stirring at room temperature for 2 hours. The reaction mixture was concentrated under reduced pressure, and isopropanol and ethyl acetate were added to the residue, followed by recrystallization. To the crystal was added a saturated sodium bicarbonate solution, followed by extraction with an isopropanol/chloroform=1:3 solution, and the organic layer was dried over anhydrous magnesium sulfate and concentrated under reduced pressure. To the residue was added isopropanol/ethyl acetate and the solid precipitated was collected by filtration to obtain sodium (1R,2S)-2-({N$^5$-[(benzyloxy)carbonyl]-N$^2$-[(2E)-3-pyridin-2-ylpro-2-penoyl]-L-ornithyl}amino)cyclopentanecarboxylate (0.14 g).

Example 102

Production Process B7

To a mixture of tert-butyl (1R,2S)-2-({N$^5$-[(benzyloxy)carbonyl]-N$^2$-(3-methoxybenzyl)-L-ornithyl}amino)cyclopentanecarboxylate (0.28 g) and ethyl acetate (3.0 ml) was added a 4 M hydrogen chloride/ethyl acetate solution (3.0 ml) at room temperature, followed by stirring at room temperature over one night. The reaction mixture was concentrated under reduced pressure, and a saturated sodium bicarbonate solution was added to the residue for neutralization, followed by extraction with ethyl acetate. The organic layer was dried over anhydrous magnesium sulfate and then concentrated under reduced pressure, and the residue was purified by silica gel column chromatography. To the compound obtained were added ethyl acetate and a 4 M-hydrogen chloride/ethyl acetate solution (0.5 mL), and the solid precipitated was collected by filtration to obtain (1R,2S)-2-({N$^5$-[(benzyloxy)carbonyl]-N$^2$-(3-methoxybenzyl)-L-ornithyl}amino)cyclopentanecarboxylic acid hydrochloride (0.12 g).

Example 14

Production Process D4

2-Oxo-2-phenylethyl (1R,2S)-2-({N$^5$-[(benzyloxy)carbonyl]-N$^2$-[(1-methyl-1H-indol-7-yl)methyl]-L-ornithyl}amino)cyclopentanecarboxylate (0.21 g) was treated in the same manner as in Example 4 (Production Process D1) to obtain (1R,2S)-2-({N$^5$-[(benzyloxy)carbonyl]-N$^2$-[(1-methyl-1H-indol-7-yl)methyl]-L-ornithyl}amino)cyclopentanecarboxylic acid (0.13 g). Then, acetonitrile (4.0 mL) and oxalic acid (23 mg) were added thereto and the solid precipitated was collected by filtration. The obtained solid was recrystallized from acetonitrile to obtain (1R,2S)-2-({N$^5$-[(benzyloxy)carbonyl]-N$^2$-[(1-methyl-1H-indol-7-yl)methyl]-L-ornithyl}amino)cyclopentanecarboxylic acid oxalate (76 mg).

Example 15

Production Process B5

Methyl (1R,2S)-2-({N$^5$-[(benzyloxy)carbonyl]-N$^2$-[(4-methoxypyridin-2-yl)carbonyl]-L-ornithyl}amino)cyclopentanecarboxylate (0.67 g) was treated in the same manner as in Example 3 (Production Process B2) to obtain (1R,2S)-2-({N$^5$-[(benzyloxy)carbonyl]-N$^2$-[(4-methoxypyridin-2-yl)carbonyl]-L-ornithyl}amino)cyclopentanecarboxylic acid (0.10 g). Then, ethyl acetate and 4 M hydrogen chloride/ethyl acetate (0.1 mL) were added thereto, followed by concentration under reduced pressure, to obtain (1R,2S)-2-({N$^5$-[(benzyloxy)carbonyl]-N$^2$-[(4-methoxypyridin-2-yl)carbonyl]-L-ornithyl}amino)cyclopentanecarboxylic acid hydrochloride (61 mg).

Example 16

Production Process B6 tert-Butyl (1R,2S)-2-({N$^5$-[(benzyloxy)carbonyl]-N$^2$-(quinoline-7-ylmethyl)-L-ornithyl}amino)cyclopentanecarboxylate (0.32 g) was treated in the same manner as in Example 2 (Production Process B1) to obtain (1R,2S)-2-({N$^5$-[(benzyloxy)carbonyl]-N$^2$-(quinoline-7-ylmethyl)-L-ornithyl}amino)cyclopentanecarboxylic acid. Then, acetonitrile and fumaric acid were added thereto, and the solid precipitated was then recrystallized from acetonitrile to obtain (1R,2S)-2-({N$^5$-[(benzyloxy)carbonyl]-N$^2$-(quinoline-7-ylmethyl)-L-ornithyl}amino)cyclopentanecarboxylic acid fumarate (0.21 g).

Example 17

Production Process A2

A mixture of benzyl [(1S,2S)-2-(2H-tetrazole-5-ylmethoxy)cyclopentyl]carbamate (0.22 g), ethanol (5.0 ml), and palladium-carbon (50 mg) were stirred at room temperature for 4 hours under a hydrogen atmosphere. The insolubles in the reaction mixture were separated by filtration through Celite, and a 4 M hydrogen chloride/ethyl acetate solution was added to the filtrate, followed by concentration under reduced pressure. The residue was treated in the same manner as in Example 1 (Production Process A1) to obtain benzyl [(4S)-4-{[(1-methyl-1H-indol-2-yl)carbonyl]amino}-5-oxo-5-{[(1S,2S)-2-(1H-tetrazole-5-ylmethoxy)cyclopentyl]amino}pentyl]carbamate (0.15 g).

Example 18

Production Process E

To a mixture of tert-butyl (1R,2S)-2-({N$^2$-[(1-methyl-1H-indol-2-yl)carbonyl]-L-ornithyl}amino)cyclopentanecarboxylate hydrochloride (0.41 g) and DMF (4.0 ml) were added cyclohexylmethyl 4-nitrophenylcarbamate (0.28 g) and triethylamine (94 mg) under ice-cooling, followed by stirring at room temperature for 1 hour. To the reaction mixture was added water (10 ml) under ice-cooling, followed by stirring at room temperature for 1 hour. The solid precipitated was collected by filtration, washed with water, and purified by silica gel column chromatography (chloroform/THF=10:1) to obtain tert-butyl (1R,2S)-2-({N$^5$-[(cyclohexylmethoxy)carbonyl]-N$^2$-[(1-methyl-1H-indol-2-yl)carbonyl]-L-ornithyl}amino)cyclopentanecarboxylate (0.41 g).

Example 19

Production Process A4

To a mixture of tert-butyl rel-(1R,2S)-2-[(tert-butoxycarbonyl)amino]cyclopropanecarboxylate (0.54 g) and diethyl ether (4.0 ml) was added a solution of p-toluene sulfonic acid monohydrate (0.40 g) in diethyl ether (16 ml) at room temperature, followed by stirring at room temperature for 5 hours. The reaction mixture was concentrated under reduced pressure to obtain tert-butyl rel-(1R,2S)-2-aminocyclopentanecarboxylate p-toluene sulfonate (0.68 g). Tert-butyl rel-(1R,2S)-2-({N$^5$-[(benzyloxy)carbonyl]-N$^2$-[(1-methyl-1H-indol-2-yl)carbonyl]-L-ornithyl}amino)cyclopropanecarboxylate (0.20 g) was obtained by using tert-butyl rel-(1R,2S)-2-aminocyclopropanecarboxylate p-toluene sulfonate (0.64 g) in the same method as for Production Process A1.

Example 20

Production Process A3

To a mixture of methyl rel-(1R,2S)-2-{[(benzyloxy)carbonyl]amino}cyclobutanecarboxylate (1.0 g), methanol (20 ml)

and 1 M hydrochloric acid (4.0 ml) was added palladium-carbon (4.0 g) at room temperature, followed by stirring at room temperature for 2 hours under a hydrogen atmosphere. The insolubles in the reaction mixture were separated by filtration through Celite and the filtrate was concentrated under reduced pressure. To the residue were added ethyl acetate and acetonitrile, the solid precipitated was separated by filtration, and the filtrate was concentrated to obtain methyl rel-(1R,2S)-2-aminocyclobutanecarboxylate hydrochloride (0.70 g). Methyl rel-(1R,2S)-2-({N$^5$-[(benzyloxy) carbonyl]-N$^2$-[(1-methyl-1H-indol-2-yl)carbonyl]-L-ornithyl}amino)cyclobutanecarboxylate (0.45 g) was obtained by using methyl rel-(1R,2S)-2-aminocyclobutanecarboxylate hydrochloride (0.31 g) in the same method as for Production Process A1.

Example 222

Production Process B8

2-Oxo-2-phenylethyl (1R,2S)-2-({N$^5$-[(benzyloxy)carbonyl]-N$^2$-(2,3-dihydro-1H-indol-6-ylcarbonyl)-L-ornithyl}amino)cyclopentanecarboxylate was obtained from ten-butyl 6-{[(1R)-4-{[(benzyloxy)carbonyl]amino}-1-({(1R,2S)-2-[(2-oxo-2-phenylethoxy)carbonyl] cyclopentyl}carbamoyl)butyl]carbamoyl}indoline-1-carboxylate by using the same method as for Production Process B1.

In the same manner as in the methods of Examples, the compounds of Examples as shown in Tables below were prepared using each of the corresponding starting materials. The structures of the compounds of Examples 1 to 284 are respectively shown in Tables 13 to 48, and the physicochemical data and the production methods are shown in Tables 49 to 59.

In addition, the following abbreviations are used in Production Examples, Examples, and Tables as below. Pre: Production Example No., Ex: Example No., Str: structural formula, Syn: production process (which means that production was made in the same manner as in the production processes of the corresponding A1 to S in Examples above. For example, B1 of Example 23 shows that production was made in the same manner as in Example 2. Further, in the case where a plural form is described, it means that the reactions are carried out in the described order.), Sal: salt (the numeral of the acid component represents a compositional ratio, and for example, 2HCl represents dihydrochloride). Dat: physicochemical data (NMR1: δ (ppm) in 1H NMR in DMSO-d$_6$, NMR2: δ (ppm) in 1H NMR in CDCl$_3$, NMR3: δ (ppm) in 1H NMR in CD$_3$OD, FAB:FAB-MS (cation), FAB-N:FAB-MS (anion), ESI:ESI-MS (cation), ESI-N:ESI-MS (anion), EI:EI-MS (cation)), Me: methyl, Et: ethyl, Ph: phenyl, Bn: benzyl, Z: benzyloxycarbonyl group, nPr: normal propyl, $^i$Pr: isopropyl, cHex: cyclohexyl, $^t$Bu: tert-butyl, Boc: tert-butoxycarbonyl, Ac: acetyl, TfO: trifluoromethanesulfonyloxy.

TABLE 2

| Pre | Str | Dat |
|---|---|---|
| 1 | (cyclopentane with NH$_2$ and CO$_2$Me, HCl) | NMR2: 8.77-8.20 (2H, brs), 3.95-3.85 (1H, m), 3.79 (3H, s), 3.09-2.97 (1H, m), 2.31-1.97 (5H, m), 1.81-1.64 (1H, m) |

TABLE 2-continued

| Pre | Str | Dat |
|---|---|---|
| 2 | (MeO$_2$C-phenyl-CO$_2$Me with NO$_2$) | NMR2: 8.56 (1H, d, J = 1.8 Hz), 8.18 (1H, dd, J = 1.8, 8.1 Hz), 7.53 (1H, d, J = 8.1 Hz), 3.95 (3H, s), 3.68 (3H, s), 3.28 (2H, t, J = 7.5 Hz), 2.75 (2H, t, J = 7.5 Hz) |
| 3 | (dihydroquinolinone-CO$_2$Me) | NMR1: 10.2 (1H, brs), 7.54-7.46 (2H, m), 7.31 (1H, d, J = 7.8 Hz), 3.82 (3H, s), 3.00-2.88 (2H, m), 2.53-2.42 (2H, m) |
| 4 | (N-allyl dihydroquinolinone-CO$_2$Me) | ESI+: 246 |
| 5 | (ornithine with Z and N-methylindole-2-carboxamide) | NMR1: 12.8-12.5 (1H, br.s), 8.63 (1H, d, J = 7.8 Hz), 7.65 (1H, d, J = 7.9 Hz), 7.53 (1H, d, J = 8.4 Hz), 7.40-7.23 (7H, m), 7.21 (1H, s), 7.15-7.06 (1H, m), 5.00 (2H, s), 4.41-4.30 (1H, m), 3.97 (3H, s), 3.11-2.97 (2H, m), 1.93-1.43 (4H, m) |
| 6 | (cyclopentane with CO$_2$Me and NHBoc) | ESI+: 244 |
| 7 | (MeO$_2$C-cyclopentyl-NH-CO-ornithine with NHZ) | ESI+: 392 |
| 8 | (O$^t$Bu ester cyclopentyl-NH-CO-ornithine with NHZ) | ESI+: 434 |
| 9 | (MeO$_2$C-N-methylindole-3-acetyl) | ESI+: 232 |

TABLE 3

| 10 | 1-Me, 2-CHO, 3-Me, 5-EtO2C pyrrole | ESI+: 237 (M + MeCN + H)+ |
| 11 | 1-Me, 2-CH2OH, 3-Me, 5-EtO2C pyrrole | ESI+: 198 |
| 12 | 3-(2-(tetrahydropyran-2-yloxy)ethoxy)benzoic acid methyl ester | FAB+: 281 |
| 13 | 1-Me-indoline-6-carboxylic acid methyl ester | ESI+: 192 |
| 14 | 1,2,4-trimethyl-5-HO2C pyrrole | ESI+: 194 (M + MeCN + H)+ |
| 15 | (1R,2S)-2-NHBoc-cyclopentane-1-carboxamide | ESI+: 229 |
| 16 | (1R,2S)-2-NHBoc-cyclopentane-1-carbonitrile | ESI+: 252 (M + MeCN + H)+ |
| 17 | 1-Et-4-Me-pyrrole-2-carboxylic acid | NMR1: 12.1-11.8 (1H, brs), 6.88 (1H, s), 6.59 (1H, s), 4.21 (2H, q, J = 7.1 Hz), 1.99 (3H, s), 1.24 (3H, t, J = 7.1 Hz) |
| 18 | (1R,2S)-2-NHBoc-cyclopentane-1-(N'-hydroxy)carboxamidine | ESI+: 244 |

TABLE 4

| 19 | Cbz-NH-1-(cyclopentyl)-CH2CH2-CO2tBu | ESI+: 348 |
| 20 | H2N-1-(cyclopentyl)-CH2CH2-CO2tBu·HCl | ESI+: 214 |
| 21 | 3-(N-Boc-N-(2-methoxyethyl)amino)benzoic acid ethyl ester | FAB+: 324 |
| 22 | (1R,2S)-2-amino-cyclopentane-1-carboxylic acid 4-methoxybenzyl ester | ESI+: 250 |
| 23 | (1R,2S)-2-NHBoc-1-(1H-tetrazol-5-yl)cyclopentane | ESI+: 254 |
| 24 | (1R,2S)-2-(N-Z-ornithinyl-amino)cyclopentane-1-carboxylic acid 4-methoxybenzyl ester | ESI+: 498 |
| 25 | (1R,2S)-2-NHBoc-1-(5-oxo-4,5-dihydro-1,2,4-oxadiazol-3-yl)cyclopentane | ESI+: 270 |
| 26 | 1-Me-indazole-4-carboxylic acid methyl ester | ESI+: 191 |

TABLE 5

| 27 | [cyclopentane with OCH2C(O)OtBu and NHZ] | ESI+: 350 |
| 28 | [cyclopentane with OCH2C(O)OtBu and NH2·HCl] | ESI+: 216 |
| 29 | MeO-CH2CH2-NH-C6H4-CO2H·HCl | ESI+: 196 |
| 30 | [BocHN-cyclopentyl-1,2,4-oxadiazole-thione] | ESI+: 286 |
| 31 | [BocHN-cyclopentyl-1,2,3,5-oxathiadiazole S-oxide] | ESI+: 290 |

TABLE 5-continued

| 32 | [BocHN-cyclopentyl-C(O)NH-NH2] | ESI+: 244 |
| 33 | [BocHN-cyclopentyl-1,3,4-oxadiazole-2-thione] | ESI+: 286 |
| 34 | [BocHN-cyclopentyl-4-methyl-1,2,4-triazole-3-thione] | ESI+: 299 |
| 35 | [BocHN-cyclopentyl-1,2,4-thiadiazol-5(4H)-one] | ESI+: 286 |

TABLE 6

| 36 | [ZHN-cyclobutane-CO2Me (cis)] | ESI+: 264 |
| 37 | [HO2C-cyclopropane-CO2tBu (cis)] | NMR2: 8.18-7.65 (1H, brs), 2.19-2.11 (1H, m), 2.09-2.01 (1H, m), 1.77-1.58 (1H, m), 1.45 (9H, s), 140-1.28 (1H, m) |
| 38 | [BocHN-cyclopropane-CO2tBu (cis)] | ESI+: 258 |
| 39 | [methyl ester with NHZ sidechain and N-methylindole-2-carboxamide] | ESI+: 438 |

TABLE 6-continued

| | | |
|---|---|---|
| 40 | (structure: cyclopentane with CO₂ᵗBu, NH, C=O, CH with NH linked to N-Me indole-2-carboxamide, side chain CH₂CH₂CH₂NHZ; HCl salt) | ESI+: 457 |
| 41 | (structure: cyclopentane with OCH₂CN and NHZ, cis) | FAB+: 275 |
| 42 | (structure: cyclopentane with O-CH₂-tetrazole and NHZ) | FAB+: 318 |
| 43 | (structure: cyclopentane with BocHN and C(=O)NH-S(=O)₂-CH₂CH₂CH₂-OAc) | FAB−: 391 |

TABLE 7

| | | |
|---|---|---|
| 44 | (structure: cyclopentane with H₂N and C(=O)NH-S(=O)₂-CH₂CH₂CH₂-OH; HCl) | ESI+: 251 |
| 45 | (structure: cyclopentane with CO₂Me and NH₂; HCl) | NMR2: 8.77-8.20 (2H, brs), 3.95-3.82 (1H, m), 3.79 (3H, s), 3.09-2.97 (1H, m), 2.31-1.97 (5H, m), 1.81-1.64 (1H, m) |
| 46 | (structure: cyclopentane with CO₂Me and NHBoc) | ESI+: 244 |
| 47 | (structure: 1-allyl-2-oxo-1,2,3,4-tetrahydroquinoline-7-carboxylic acid) | ESI+: 232 |

TABLE 7-continued
| | | |
|---|---|---|
| 48 | 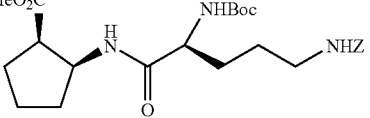 | ESI+: 492 |
| 49 | 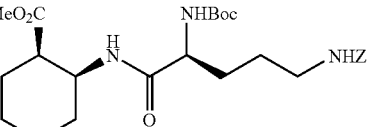 | ESI+: 506 |
| 50 | 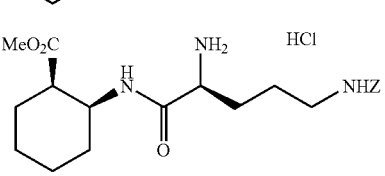 | ESI+: 406 |
| 51 | 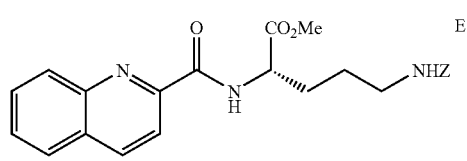 | ESI+: 436 |
| 52 | 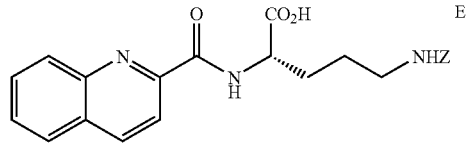 | ESI+: 422 |
TABLE 8
| | | |
|---|---|---|
| 53 | 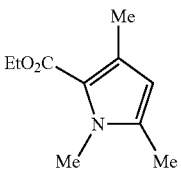 | ESI+: 182 |
| 54 | 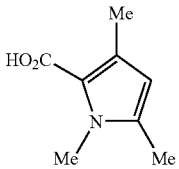 | ESI+: 154 |
| 55 | 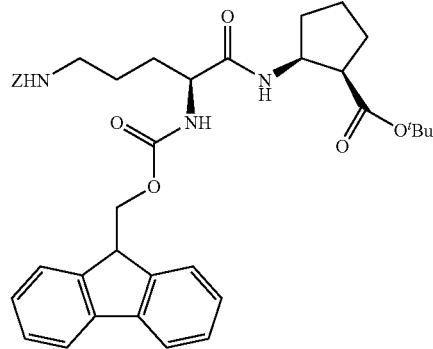 | ESI+: 656 |
| 56 | 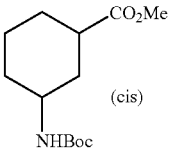 (cis) | ESI+: 258 |
| 57 | 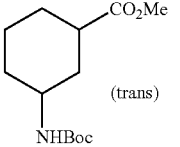 (trans) | ESI+: 258 |
| 58 | 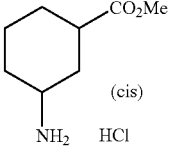 (cis) | ESI+: 158 |

TABLE 8-continued
| 59 | 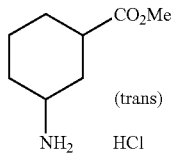 (trans) | ESI+: 158 |
| --- | --- | --- |
| 5 | 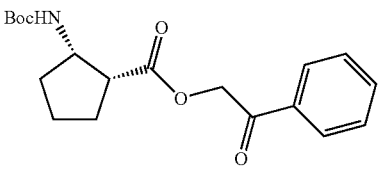 | ESI+: 348 |
TABLE 9
| 61 | 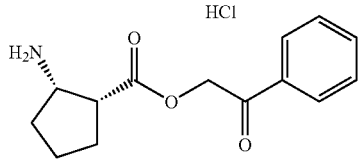 | ESI+: 248 |
| --- | --- | --- |
| 62 | 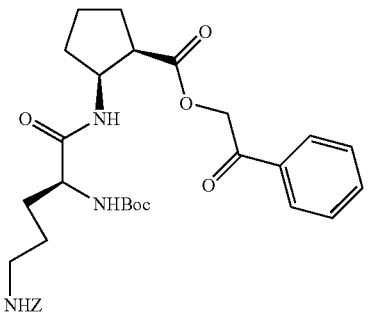 | ESI+: 596 |
| 63 | 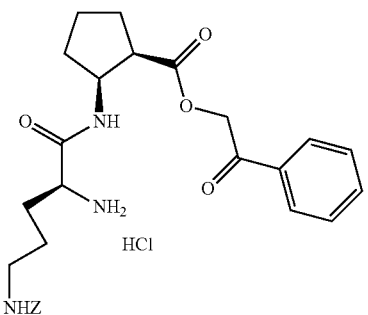 | ESI+: 496 |
| 64 | 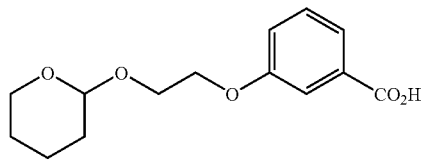 | FAB−: 265 |
| 65 | 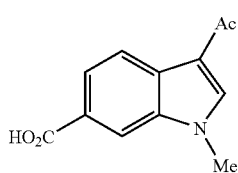 | ESI+: 218 |
| 66 | 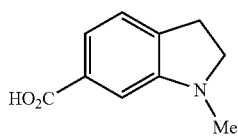 | ESI+: 178 |

…

TABLE 11-continued
| | | |
|---|---|---|
| 82 | 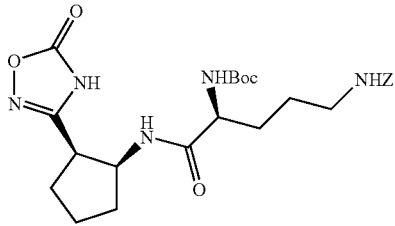 | ESI+: 518 |
| 83 | 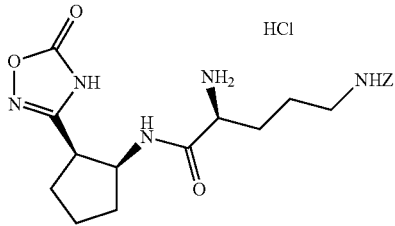 HCl | ESI+: 418 |
| 84 | 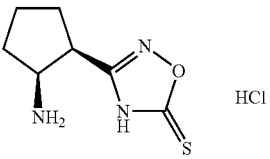 HCl | ESI+: 186 |
TABLE 12
| | | |
|---|---|---|
| 85 | 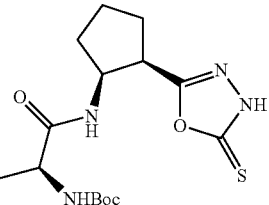 HCl | ESI+: 190 |
| 86 | 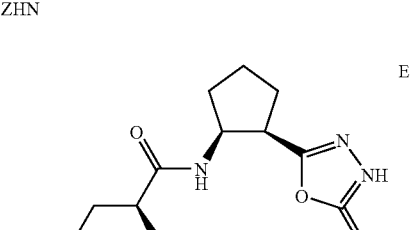 | ESI+: 350 |
| 87 | 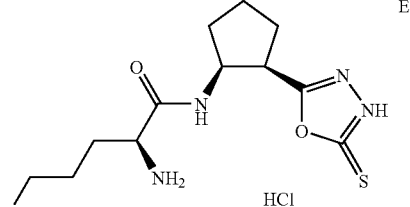 HCl | ESI+: 216 |
| 88 | 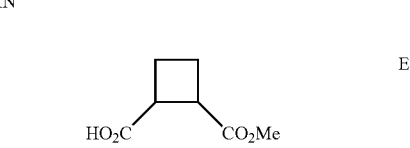 HCl | ESI+: 186 |
| 89 | 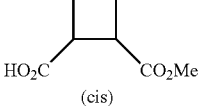 HCl | ESI+: 199 |
TABLE 12-continued
| | | |
|---|---|---|
| 90 | 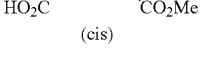 | ESI+: 534 |
| 91 | 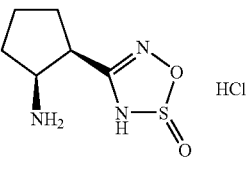 HCl | ESI+: 434 |
| 92 | 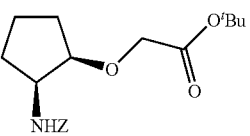 (cis) | ESI+: 159 |
TABLE 13
| Ex | Str |
|---|---|
| 21 | 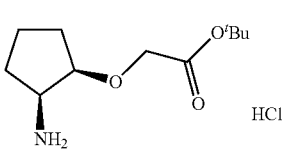 |
| 2 | 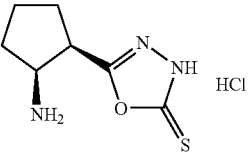 |

TABLE 13-continued
| Ex | Str |
|---|---|
| 3 | 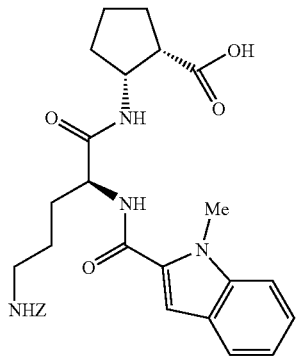 |
| 22 | 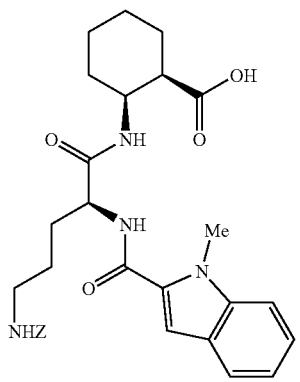 |
| 23 | 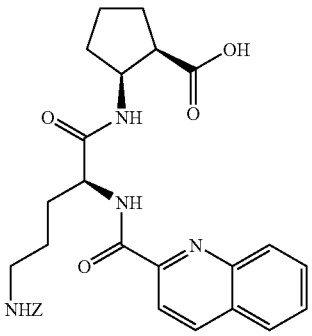 |
| 24 | 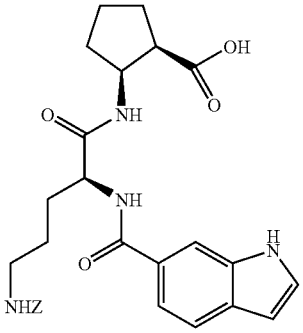 |
TABLE 13-continued
| Ex | Str |
|---|---|
| 9 | 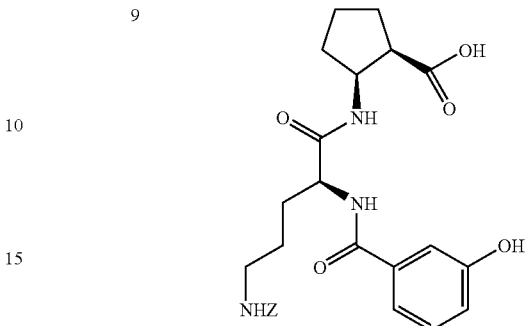 |
| 25 | 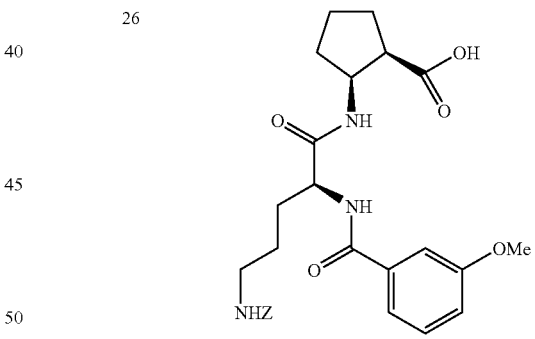 |
TABLE 14
| Ex | Str |
|---|---|
| 26 | 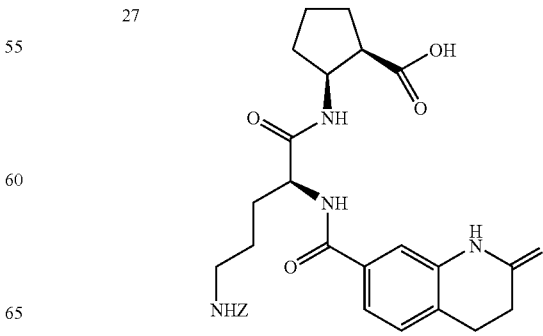 |
| 27 | 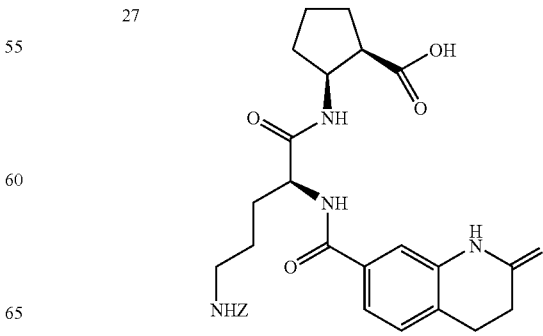 |

TABLE 14-continued
| 28 | 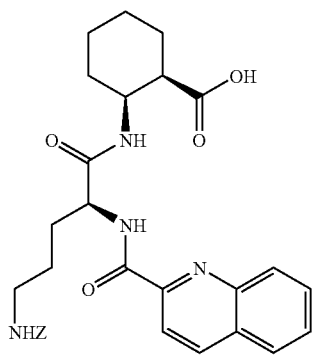 |
| 29 | 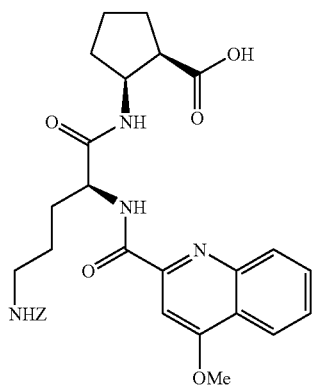 |
| 30 | 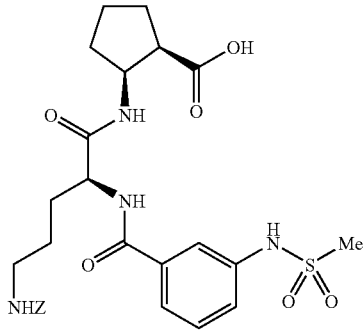 |
| 31 | 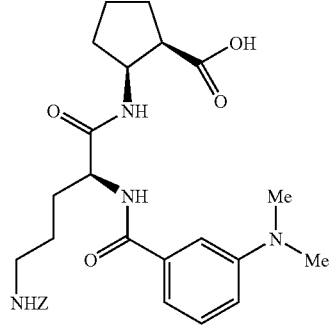 |
TABLE 14-continued
| 32 | 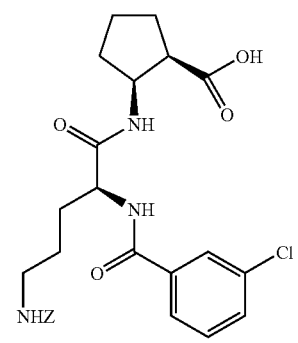 |
| 33 | 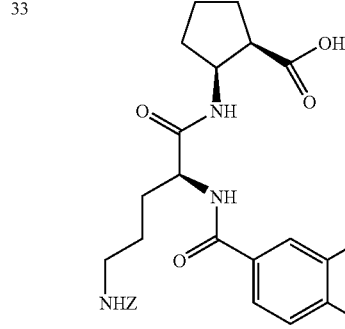 |
TABLE 15
| 34 | 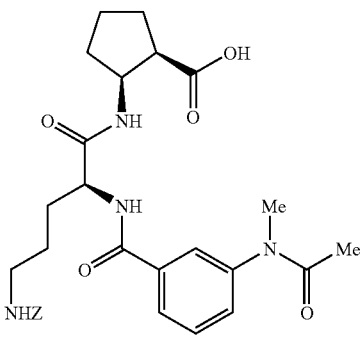 |
| 35 | 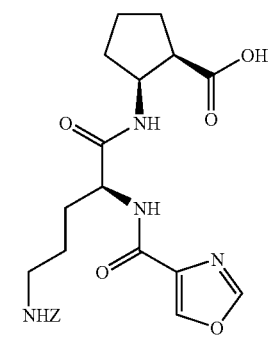 |

TABLE 15-continued
| 36 | 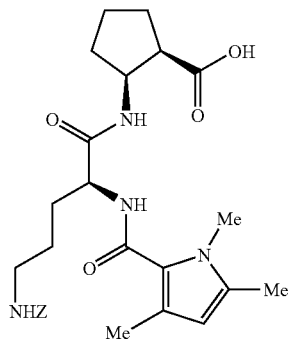 |
| 37 | 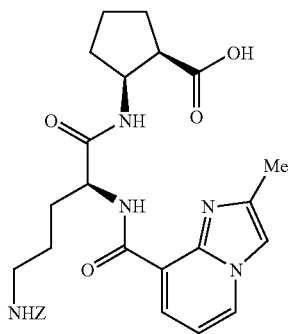 |
| 38 | 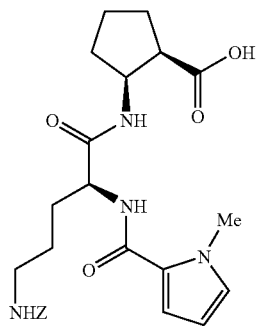 |
| 39 | 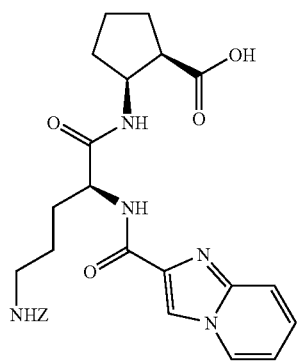 |
TABLE 15-continued
| 40 | 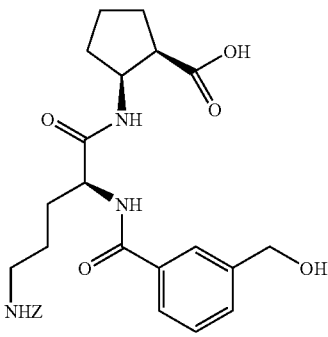 |
| 41 | 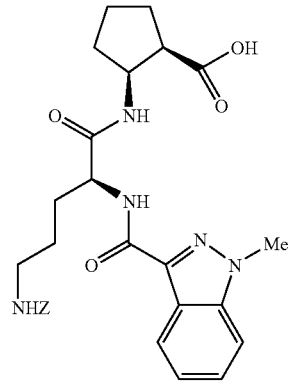 |
TABLE 16
| 15 | 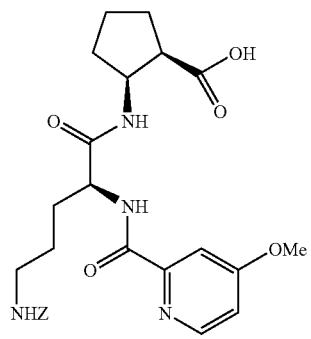 |
| 42 | 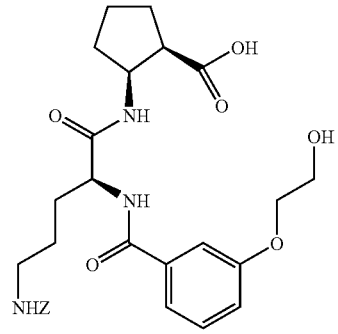 |

TABLE 16-continued
43 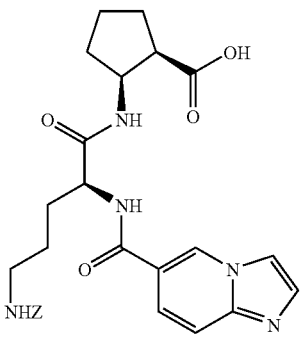
44 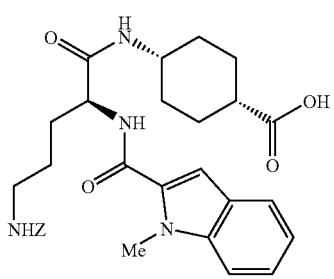
45 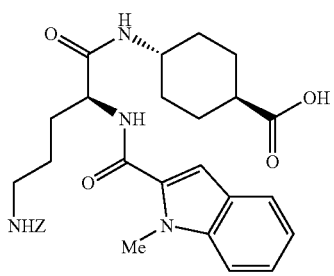
46 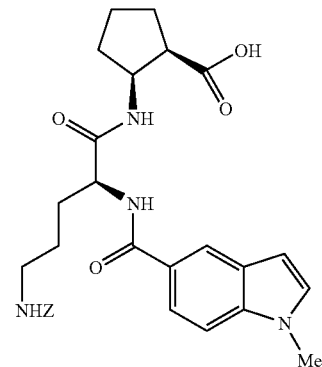
TABLE 16-continued
47 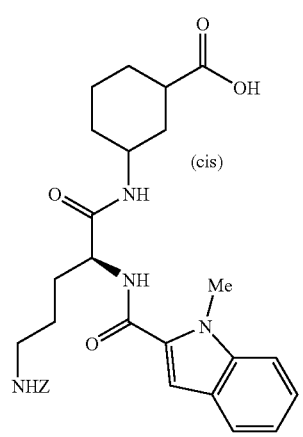
48 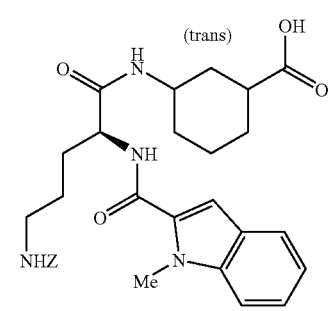
TABLE 17
49 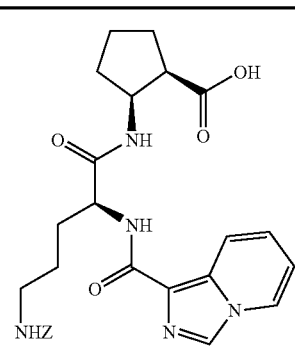
50 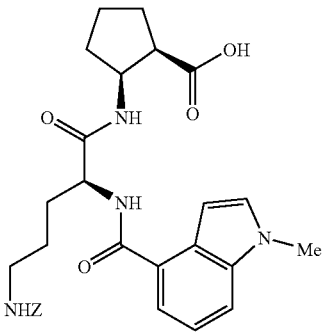

TABLE 17-continued
51
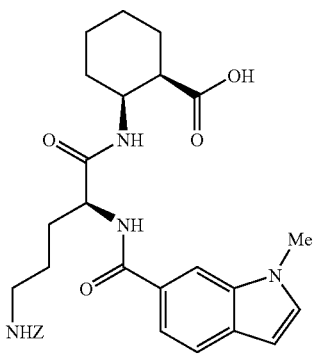
52
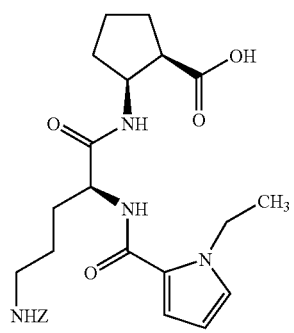
53
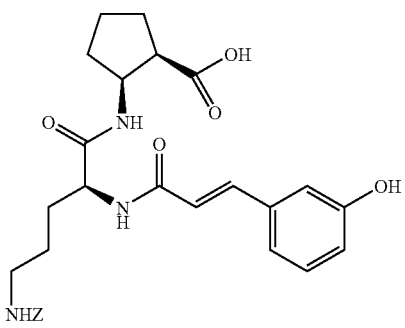
54
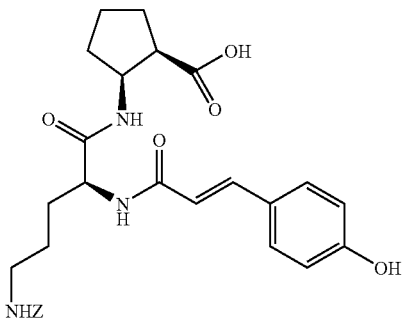
TABLE 17-continued
55
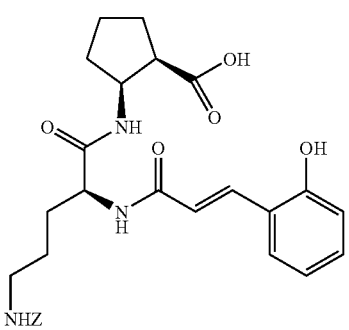
56
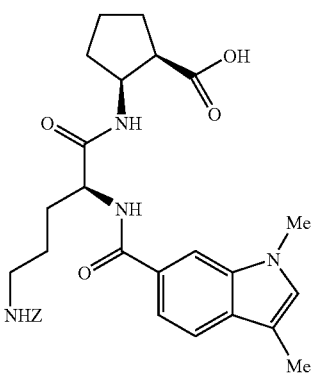
TABLE 18
57
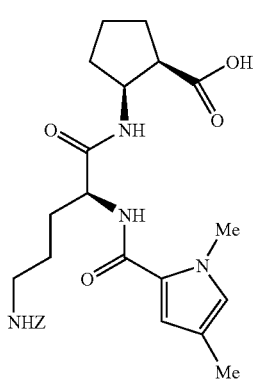
58
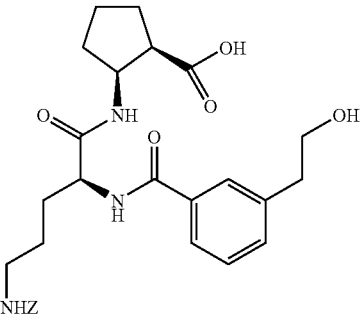

TABLE 18-continued
59 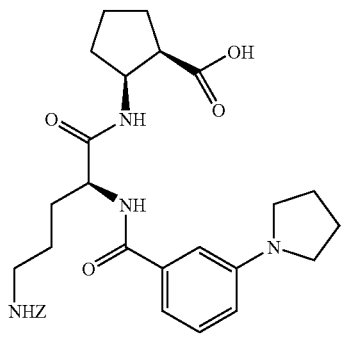
60 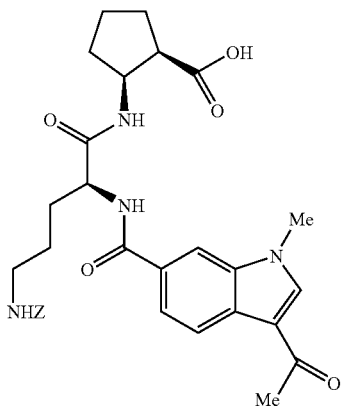
61 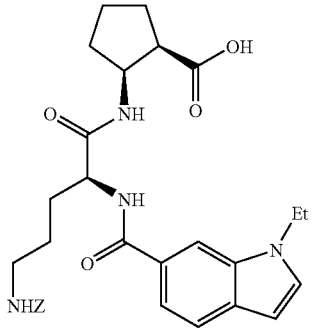
62 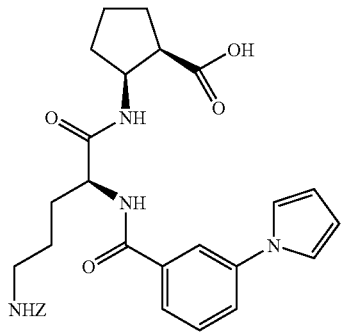
TABLE 18-continued
63 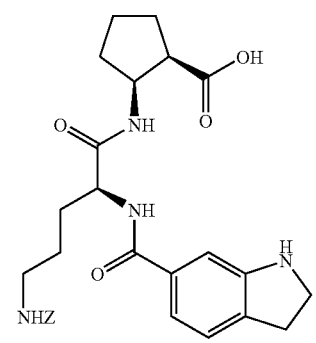
64 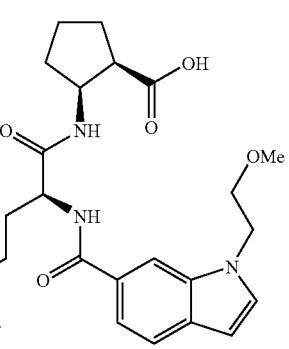
TABLE 19
65 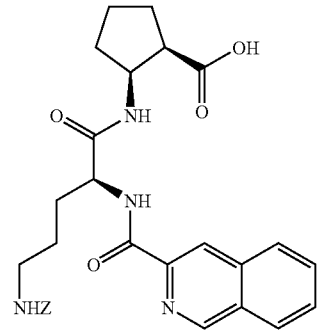
66

TABLE 19-continued
4 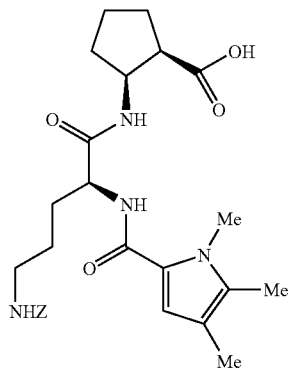
67 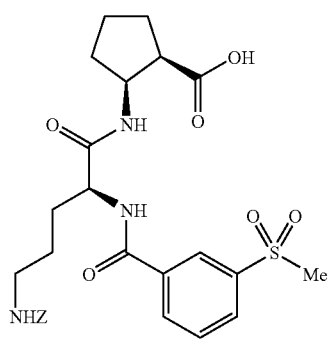
68 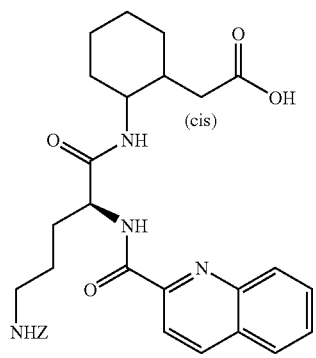
(cis)
69 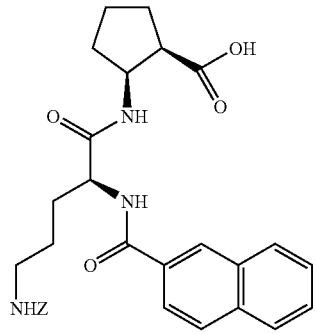
TABLE 19-continued
11 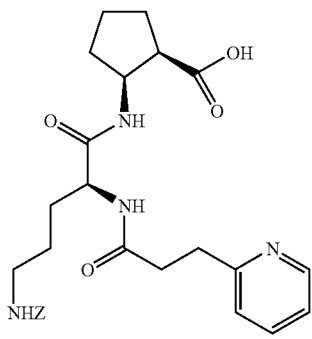
70 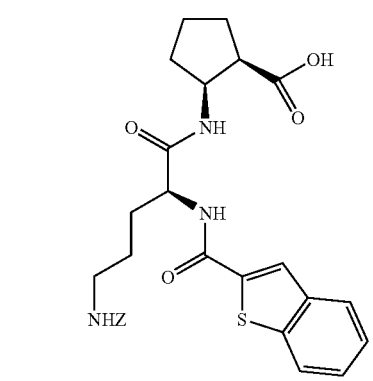
TABLE 20
71 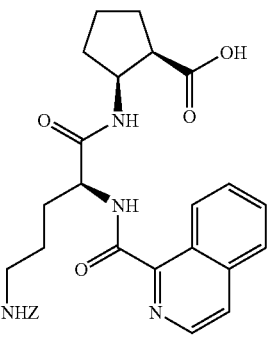
72 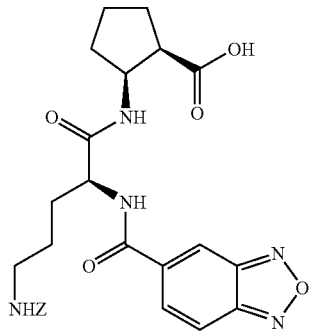

TABLE 20-continued
| 73 | 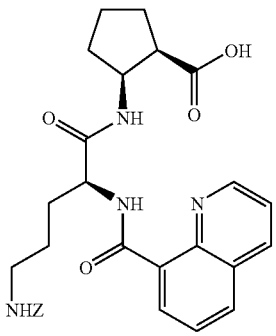 |
| 74 | 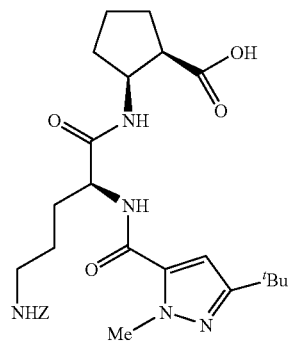 |
| 75 | 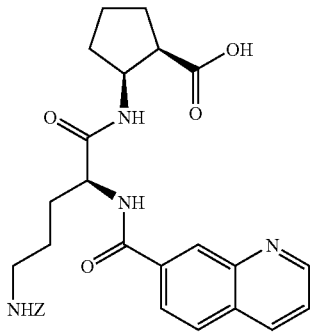 |
| 76 | 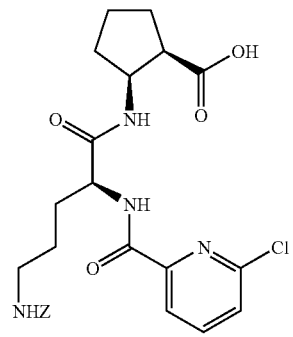 |
TABLE 20-continued
| 77 | 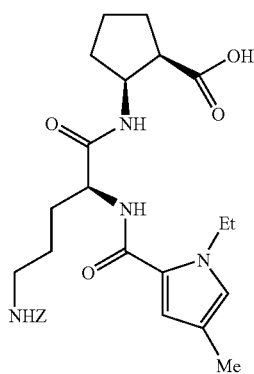 |
| 78 | 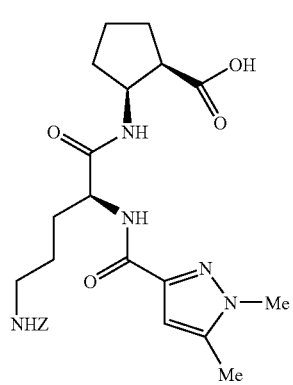 |
TABLE 21
| 79 | |
| 80 | 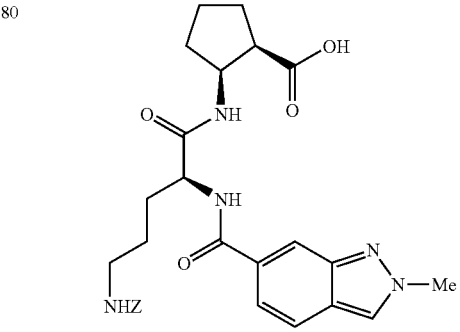 |

TABLE 21-continued
| 81 | 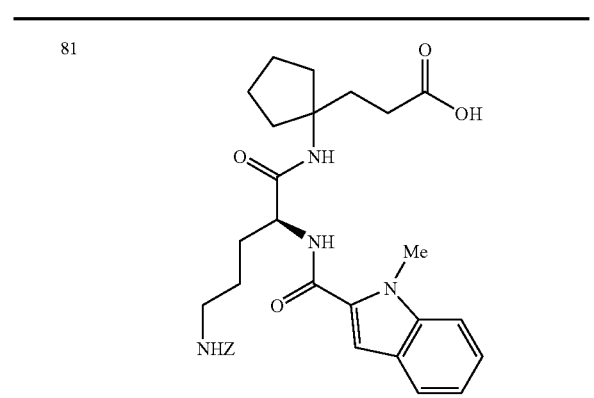 |
|---|---|
| 13 | |
| 6 | 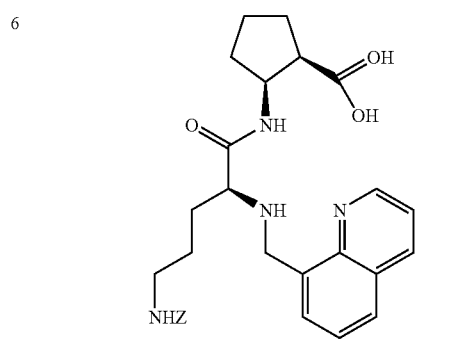 |
| 82 | |
TABLE 21-continued
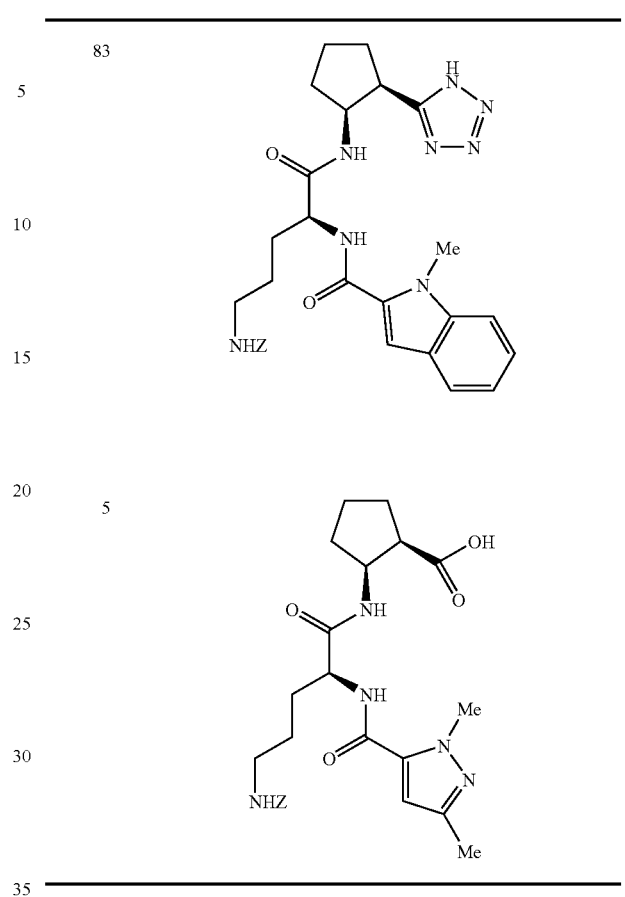
TABLE 22
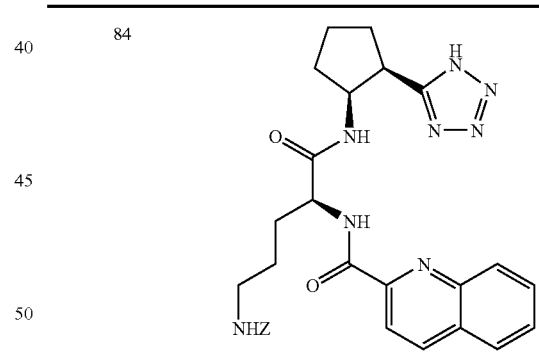
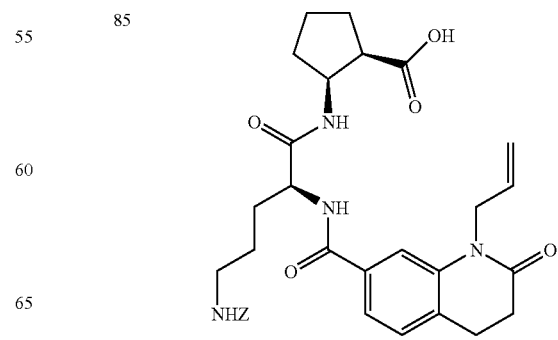

TABLE 22-continued
| 86 | 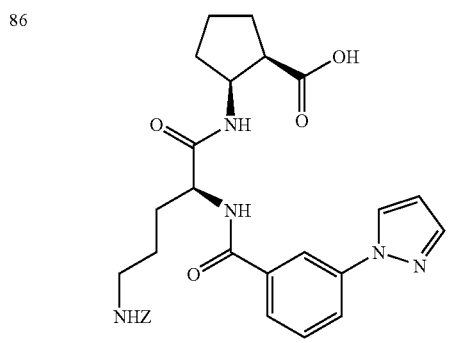 |
| 87 | |
| 88 | |
| 89 | |
TABLE 22-continued
| 90 | 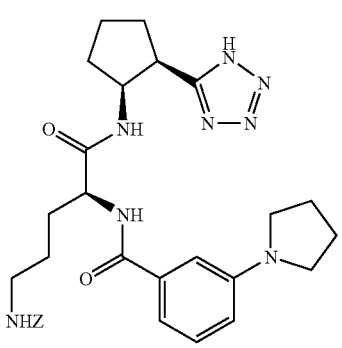 |
| 91 | |
TABLE 23
| 92 | 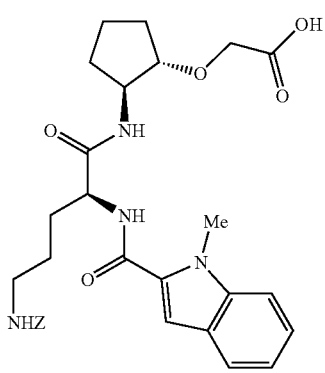 |
| 93 | |
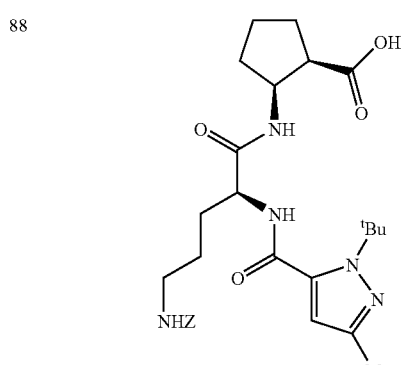

TABLE 23-continued
94
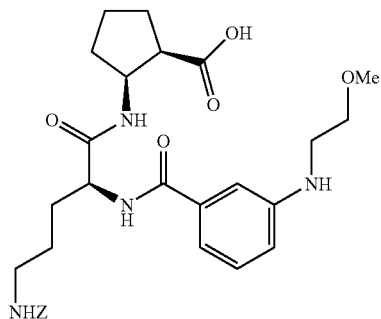
8
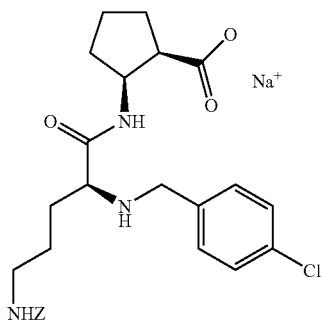
95
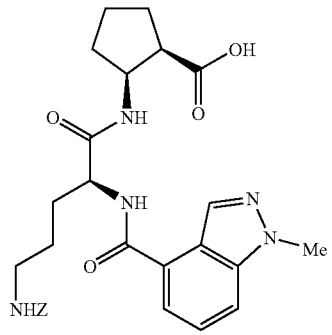
96
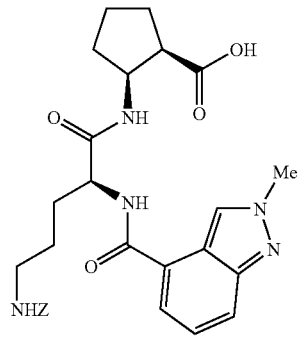
TABLE 23-continued
97
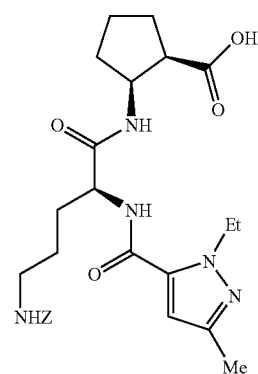
98
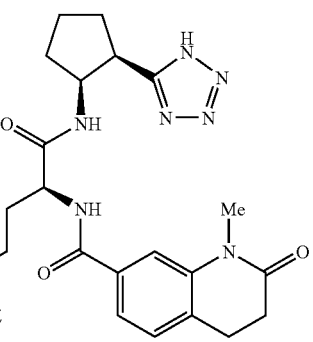
TABLE 24
99
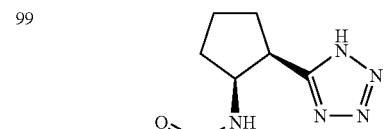
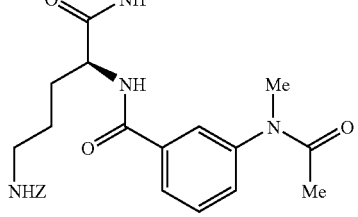
100
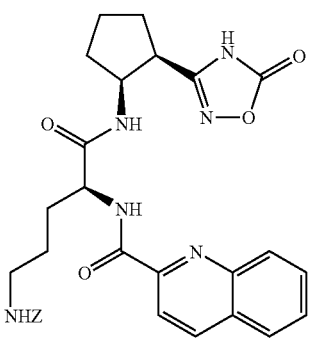

TABLE 24-continued
101 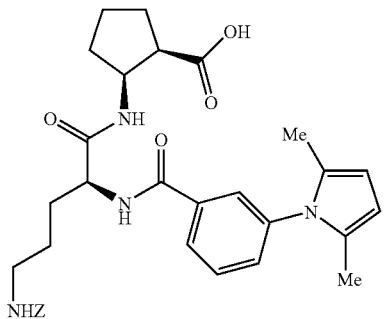
102 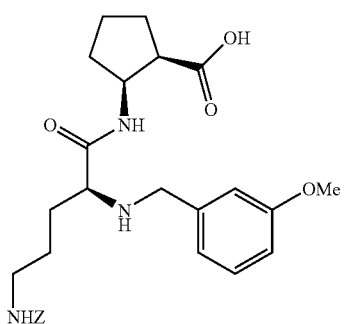
103 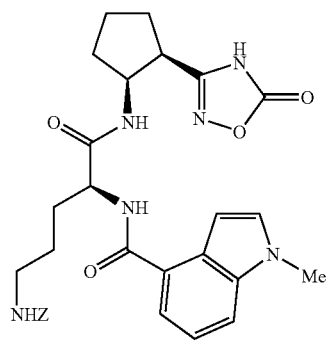
104 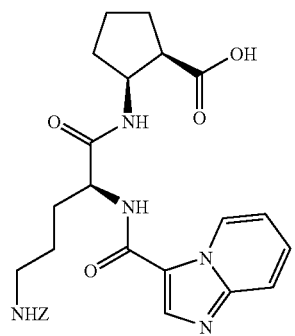
TABLE 24-continued
105 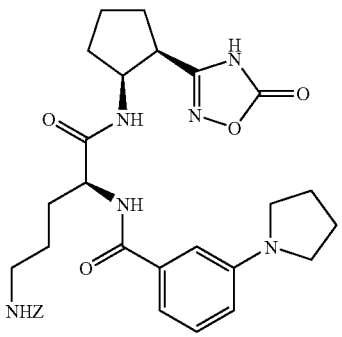
106 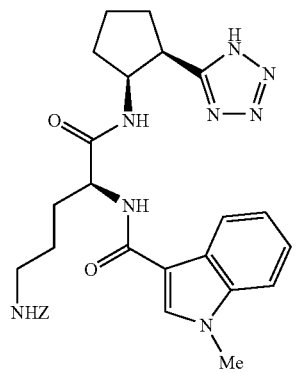
TABLE 25
107 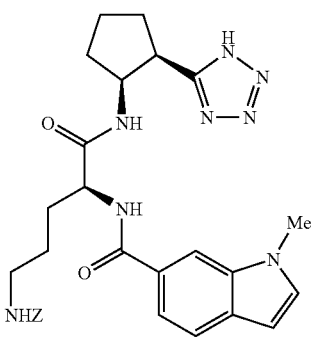
108 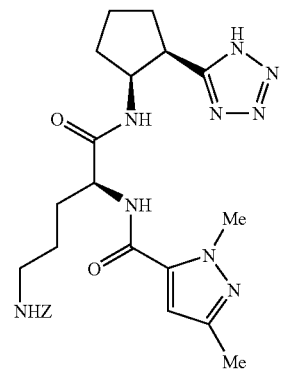

TABLE 25-continued
| | |
|---|---|
| 109 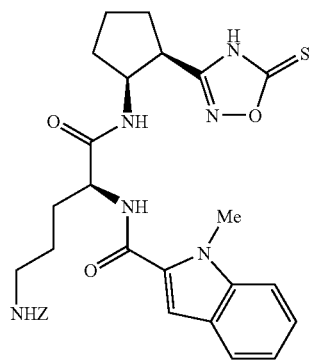 | 113 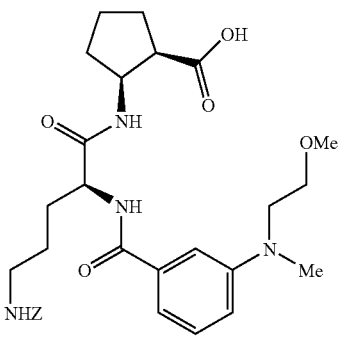 |
| 110 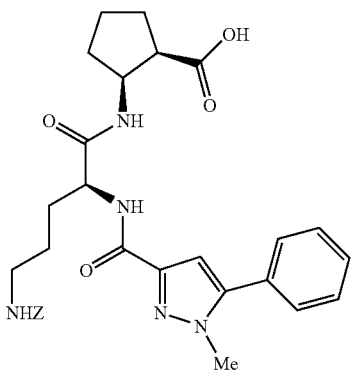 | 114 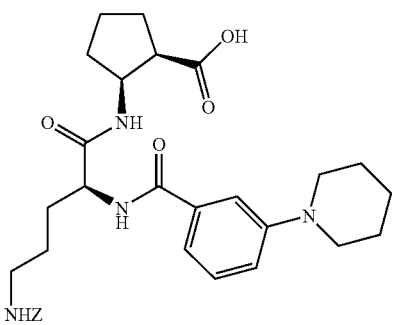 |
TABLE 26
| | |
|---|---|
| 111 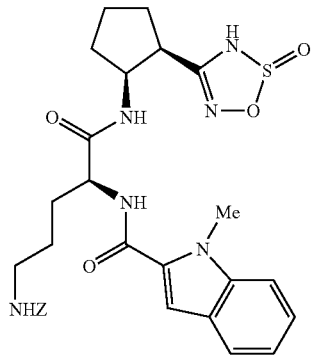 | 115 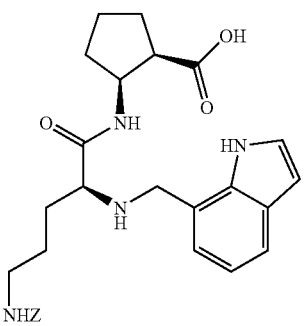 |
| 112 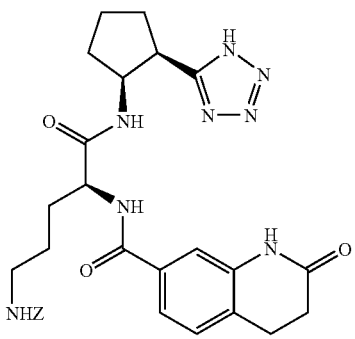 | 16 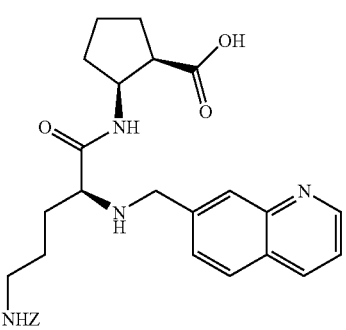 |

TABLE 26-continued
116 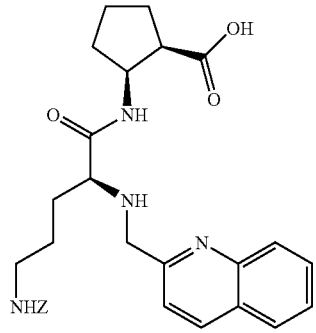
117 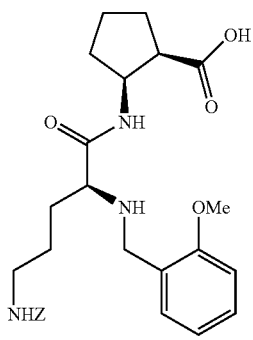
118 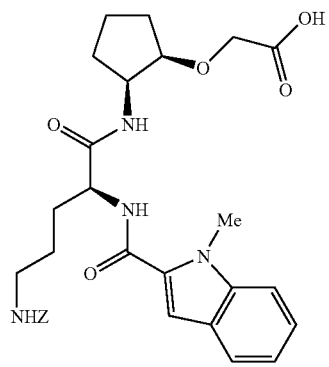
14 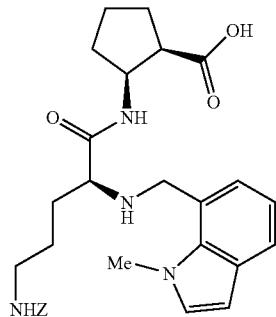
119 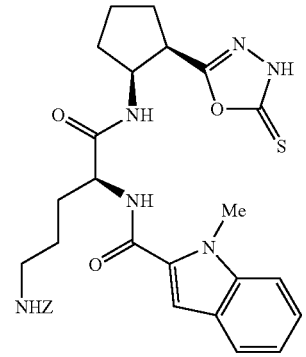
120 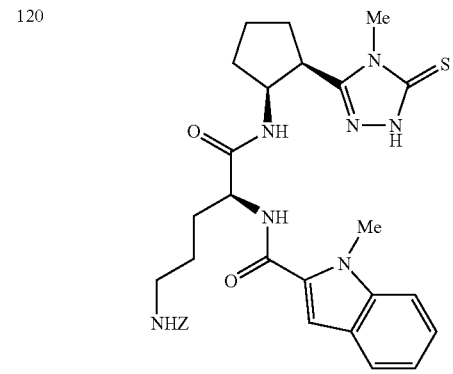
TABLE 27
121 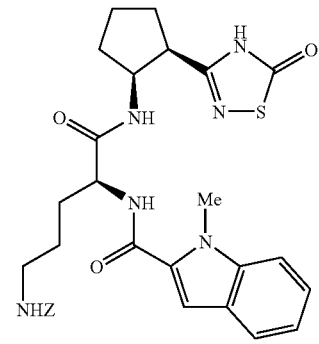
122 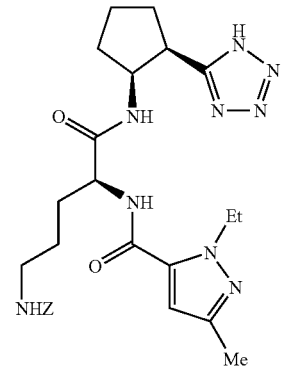

TABLE 27-continued
123 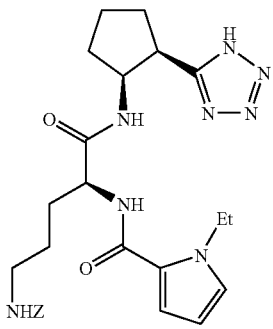
124 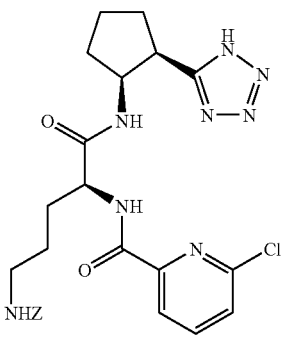
125 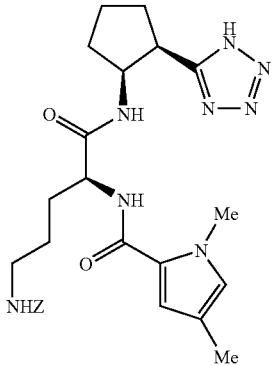
126 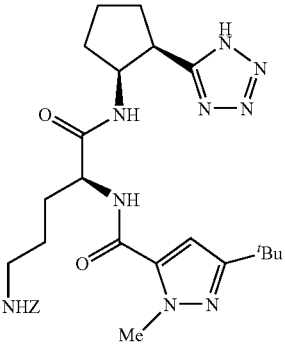
TABLE 27-continued
127 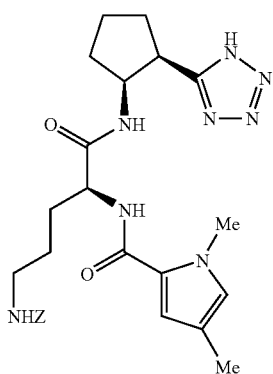
128 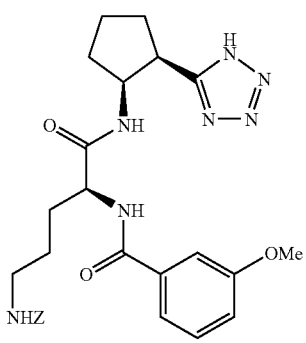
TABLE 28
129 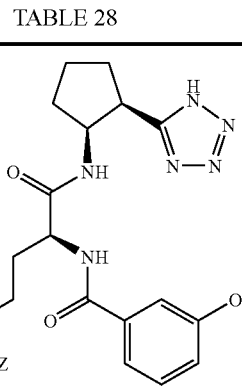
130 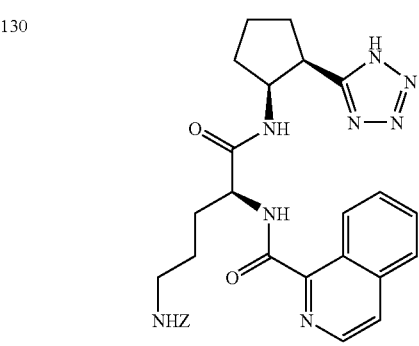

TABLE 28-continued
131 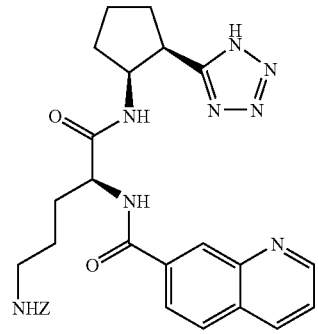
132 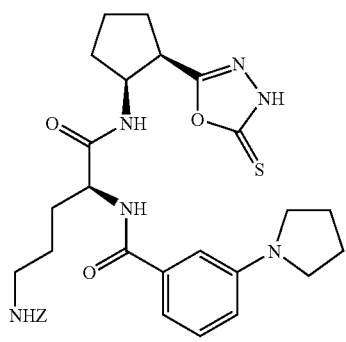
133 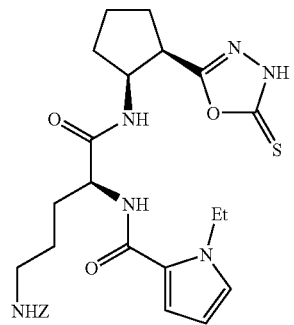
134 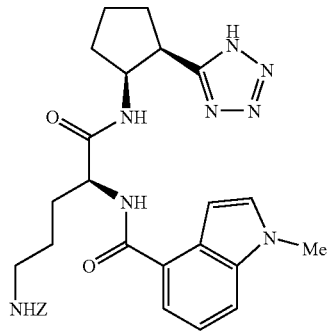
TABLE 28-continued
135 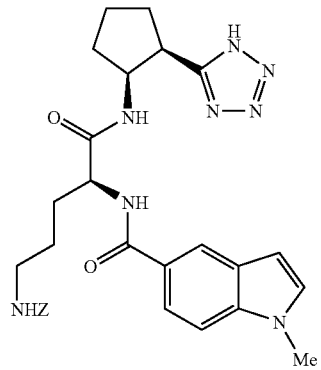
136 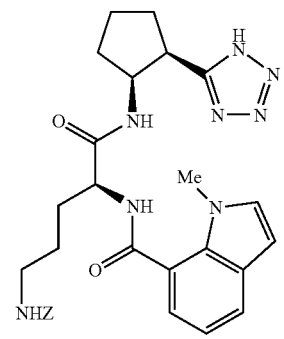
TABLE 29
137 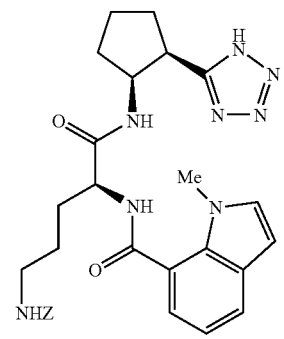
138 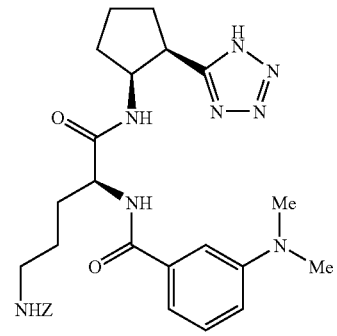

TABLE 29-continued
139 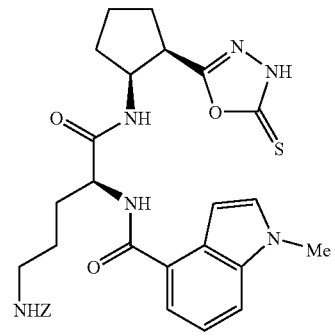
140 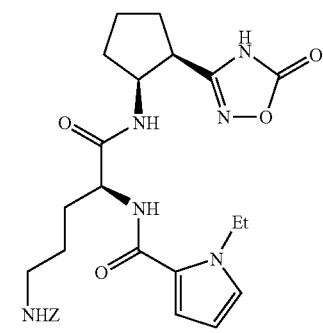
141 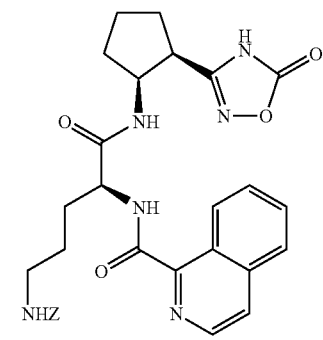
142 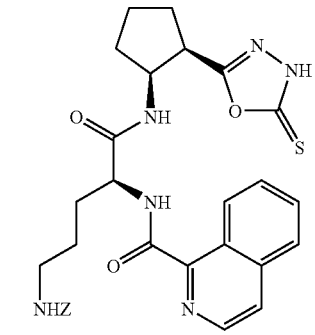
TABLE 29-continued
143 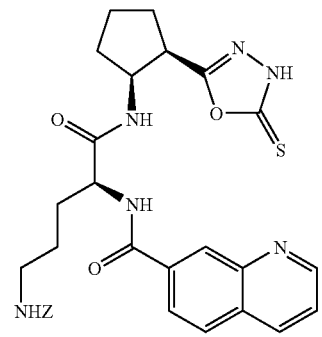
144 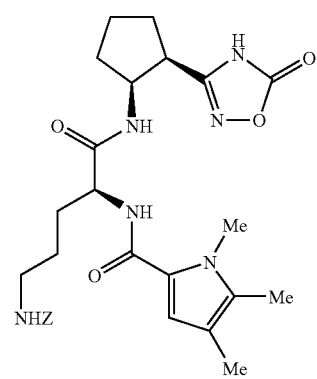
TABLE 30
145 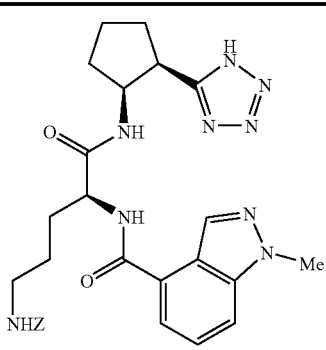
146 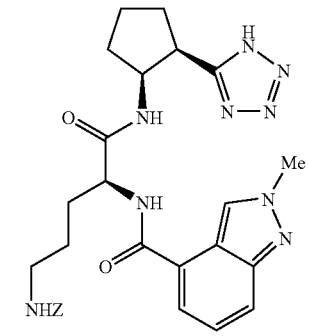

TABLE 30-continued
147 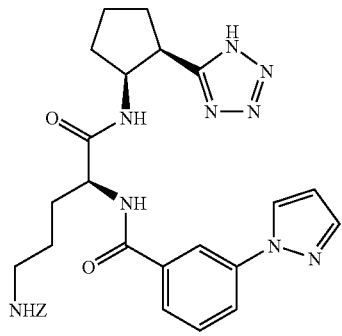
148 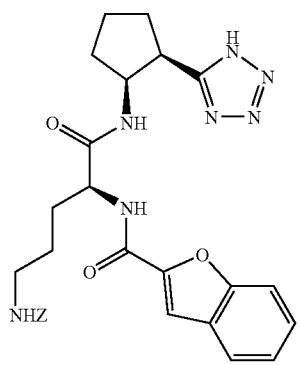
149 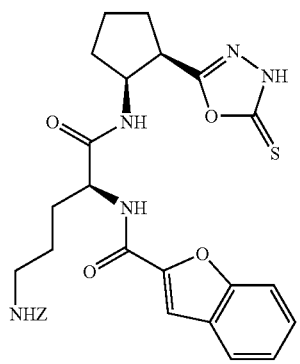
17 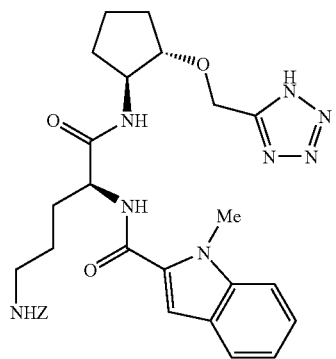
TABLE 30-continued
150 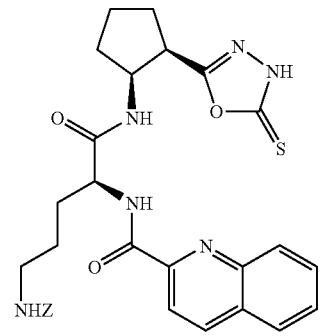
151 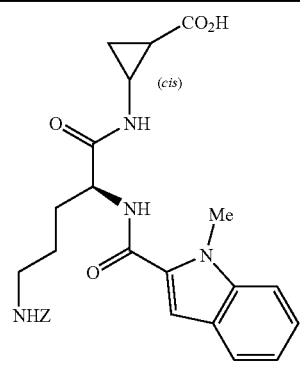
TABLE 31
152 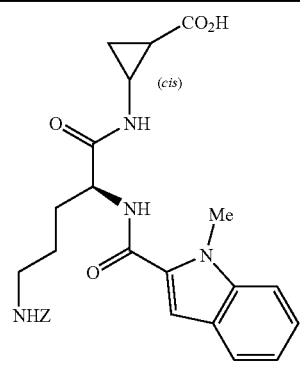
153 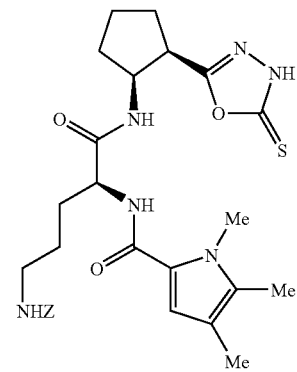

TABLE 31-continued
| 154 | 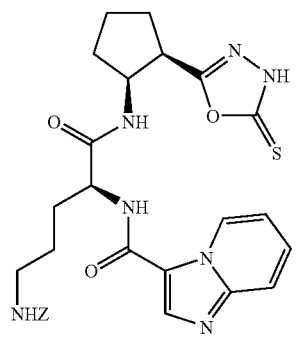 |
| 12 | 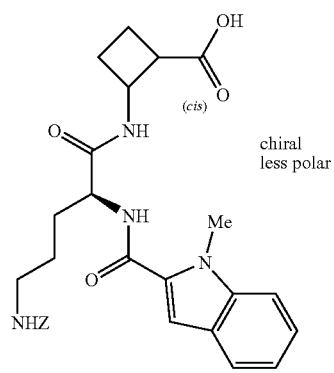 chiral less polar |
| 155 | 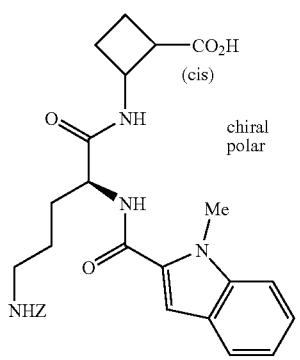 chiral polar |
| 156 | 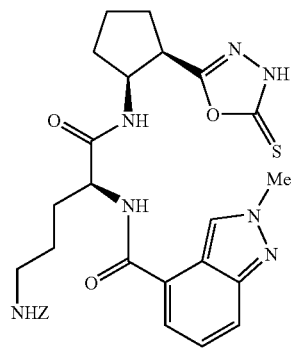 |
TABLE 31-continued
| 157 | 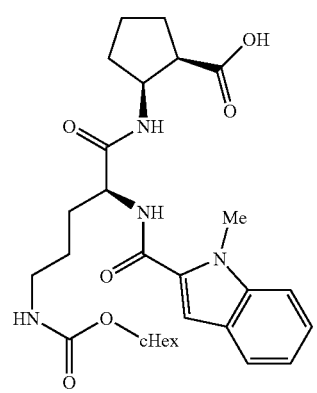 |
| 158 | 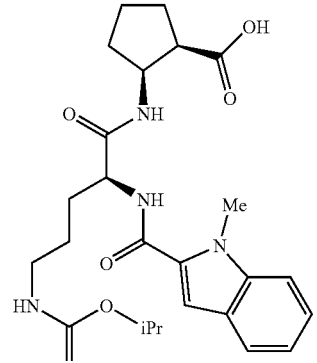 |
TABLE 32
| 159 | 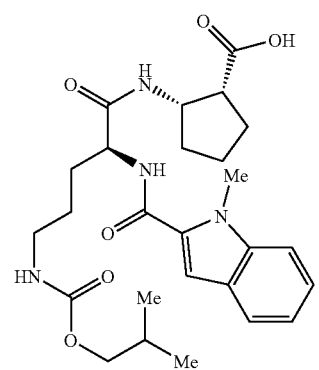 |
| 160 | 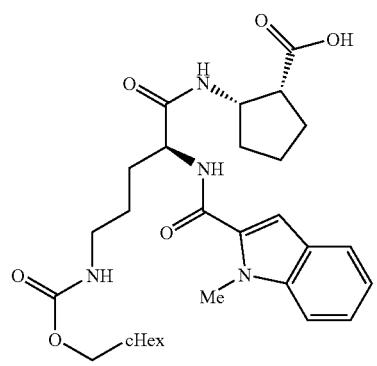 |

TABLE 32-continued

161

162

163

164

TABLE 32-continued

165

166

TABLE 33

167

168

TABLE 33-continued
169 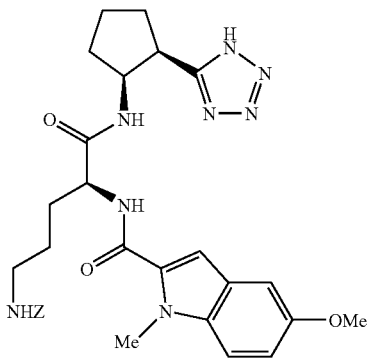
170 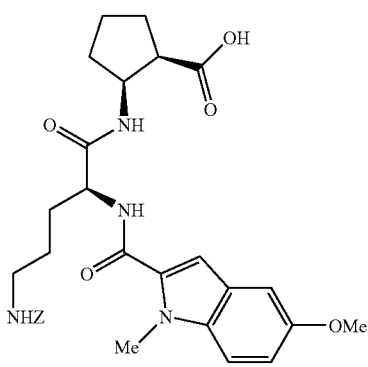
171 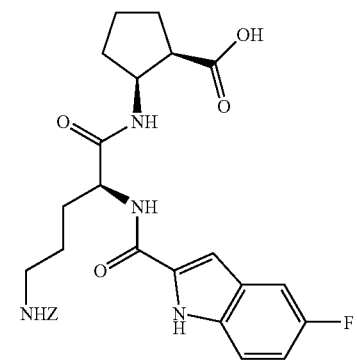
172 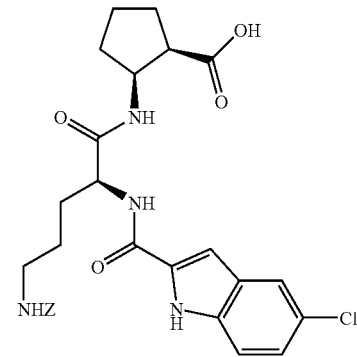
TABLE 33-continued
173 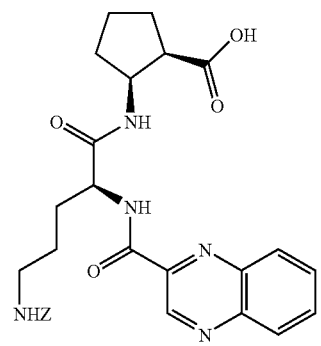
174 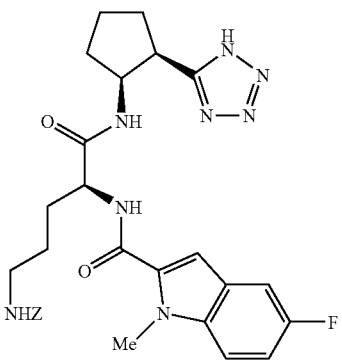
TABLE 34
175 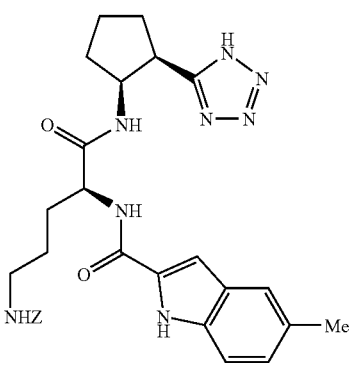
176 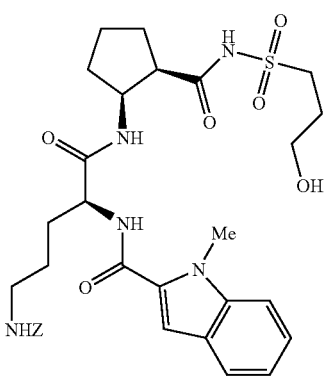

TABLE 34-continued
275 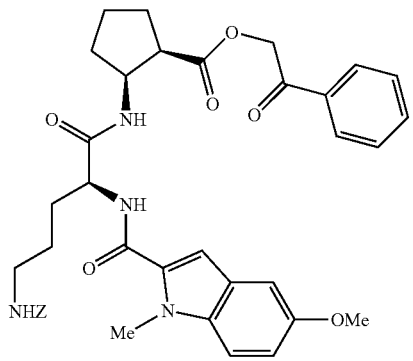
276 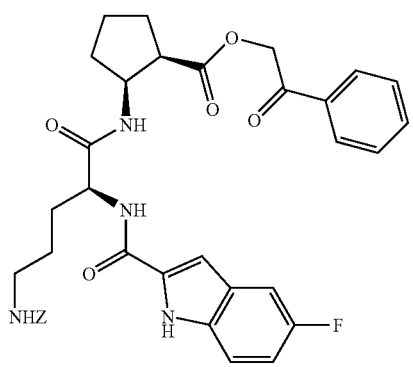
277 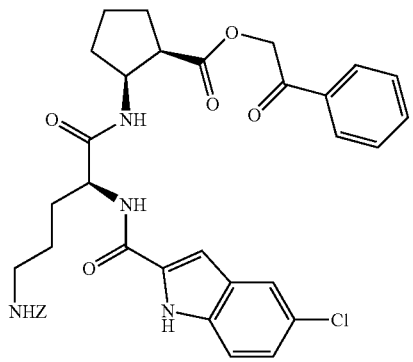
284 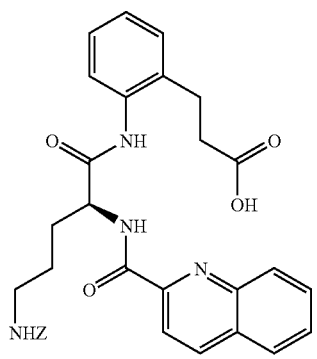
TABLE 35
177 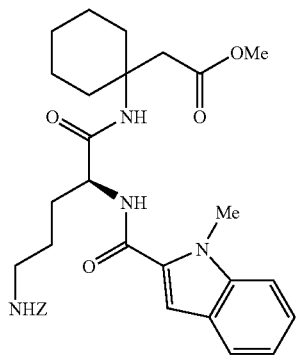
1 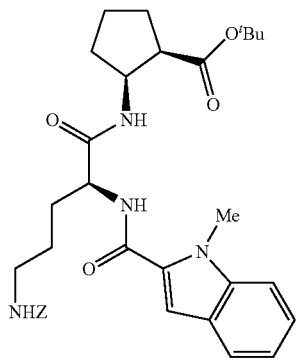
178 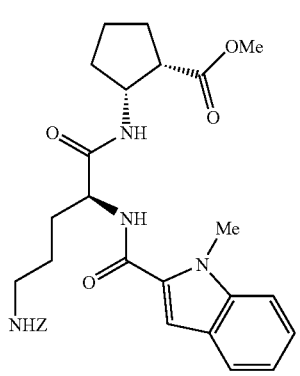
179 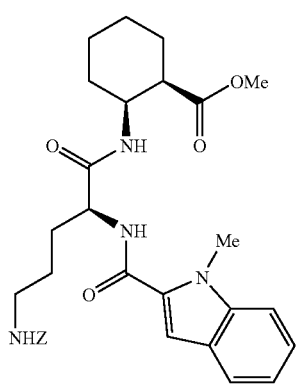

TABLE 35-continued
180 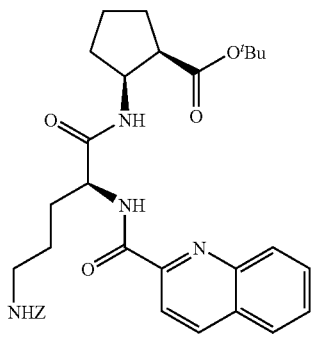
181 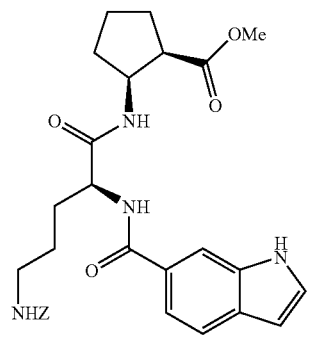
182 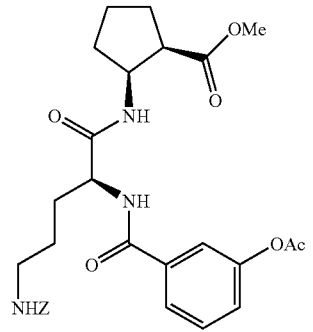
183 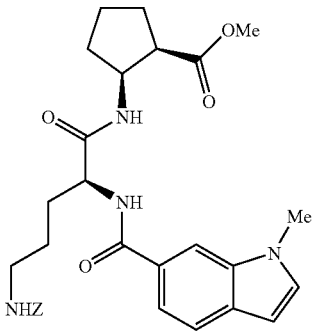
TABLE 36
184 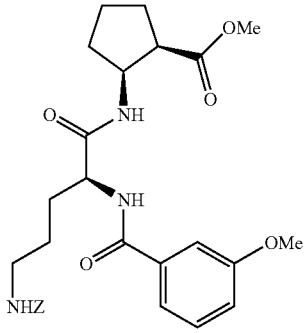
185 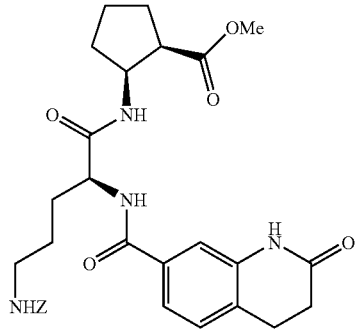
186 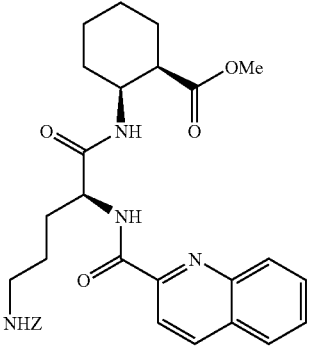
187 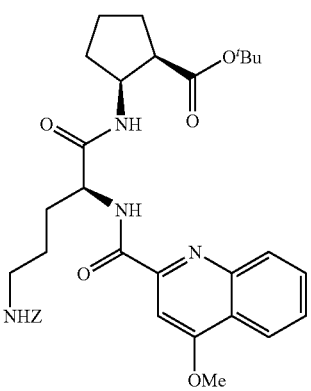

TABLE 36-continued
188 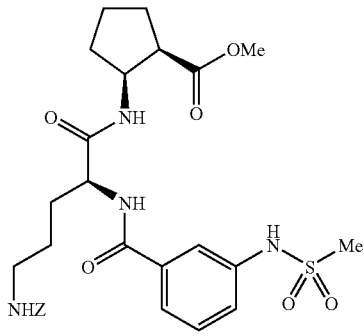
189 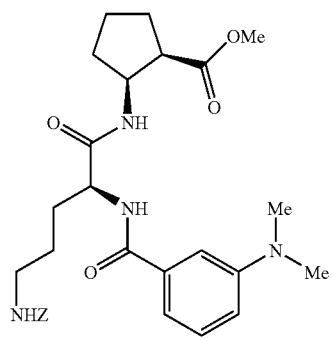
190 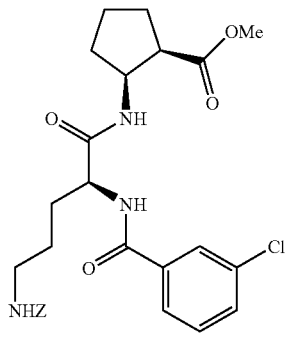
191 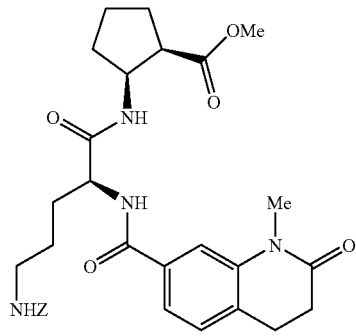
TABLE 37
192 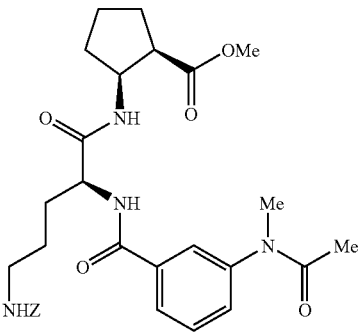
193 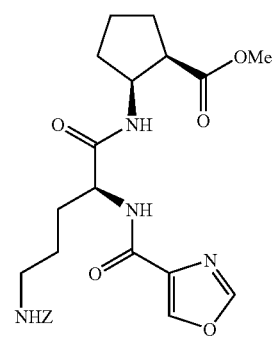
194 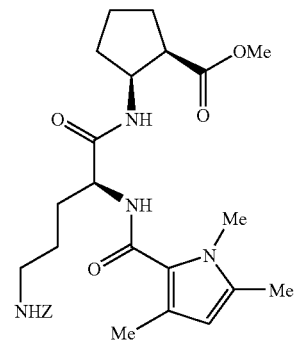
195 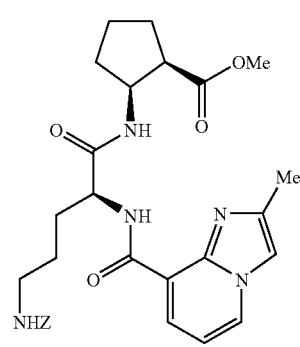

TABLE 37-continued
196 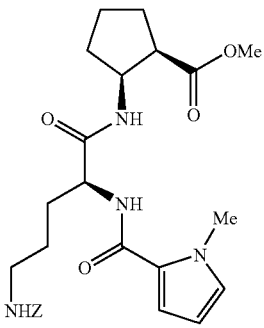
197 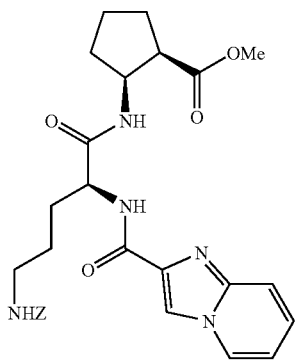
198 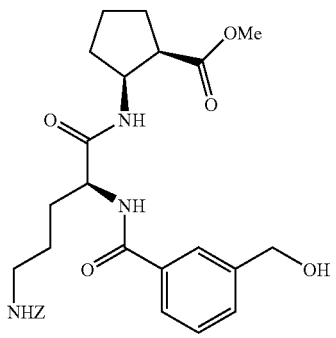
199 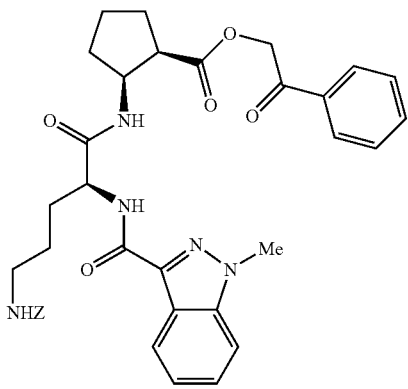
TABLE 38
200 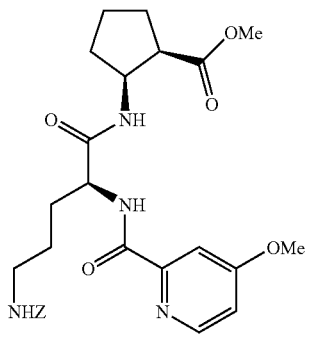
201 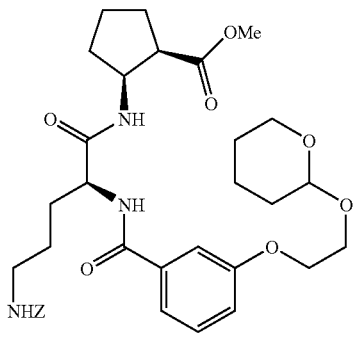
10 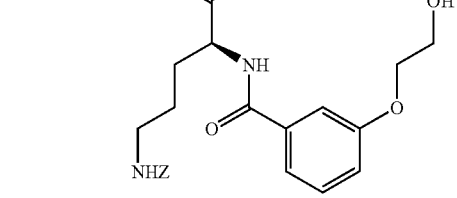
202 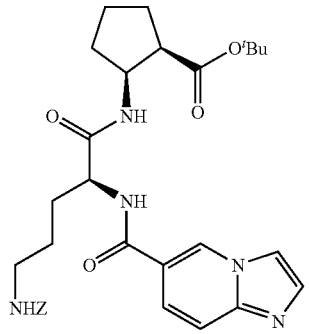
203 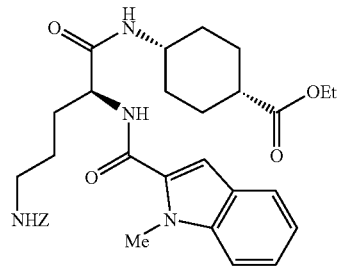

TABLE 38-continued
204 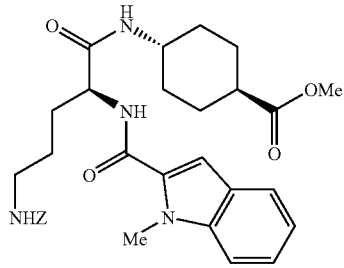
205 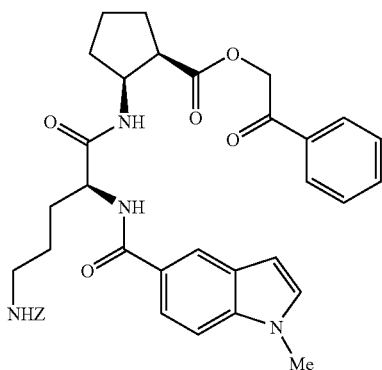
206 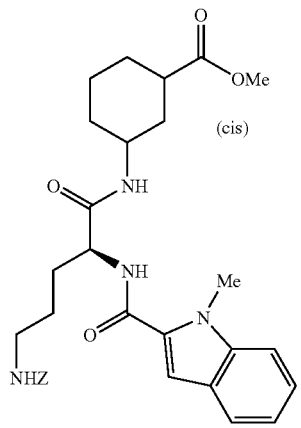
TABLE 39
207 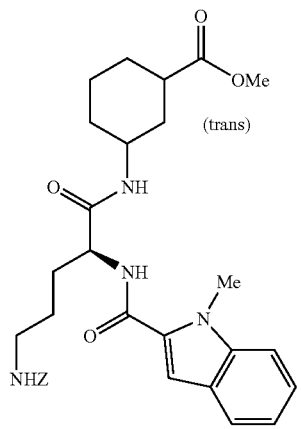
TABLE 3
208 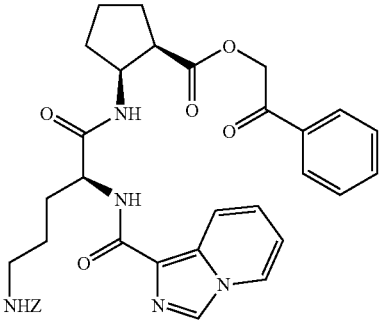
209 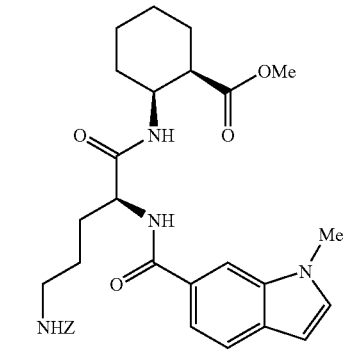
210 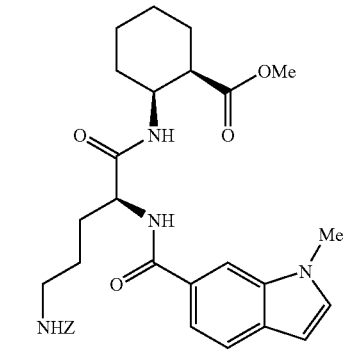
211 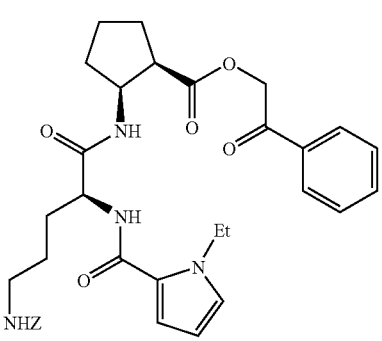

TABLE 39-continued
212 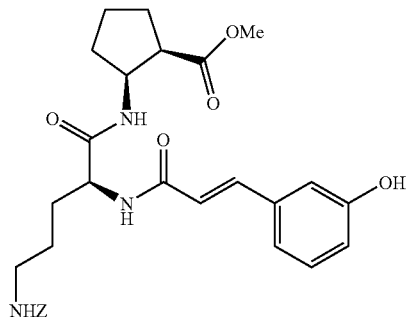
213 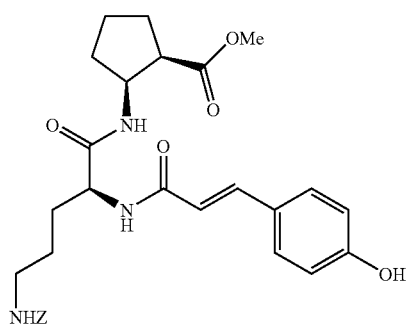
214 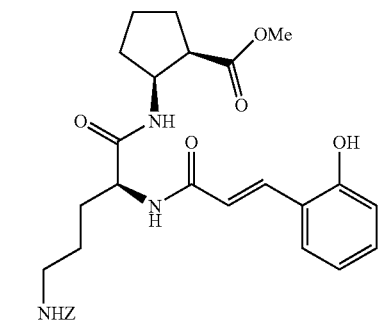
TABLE 40
215 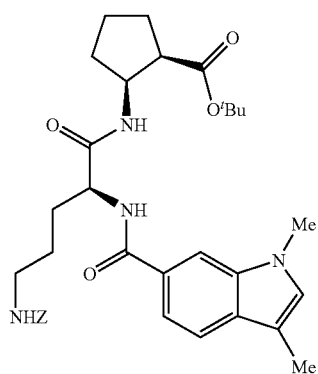
TABLE 40-continued
216 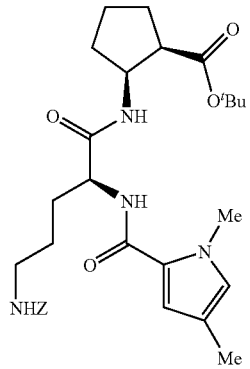
217 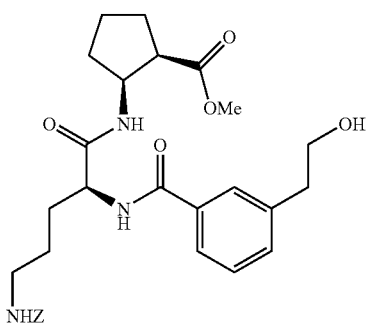
218 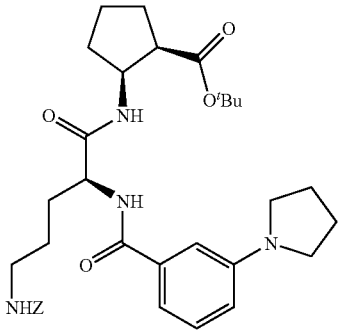
219 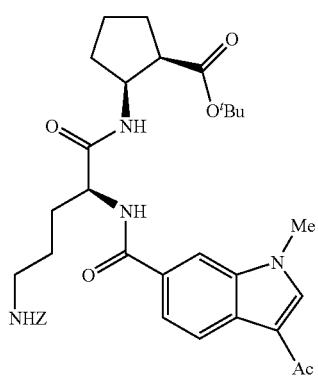

TABLE 40-continued
220 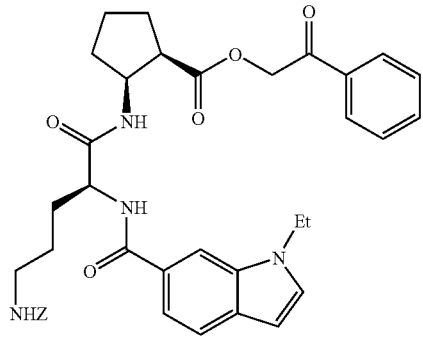
221 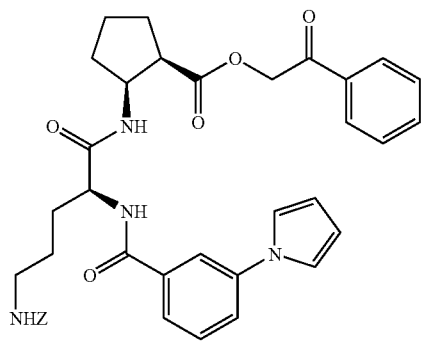
222 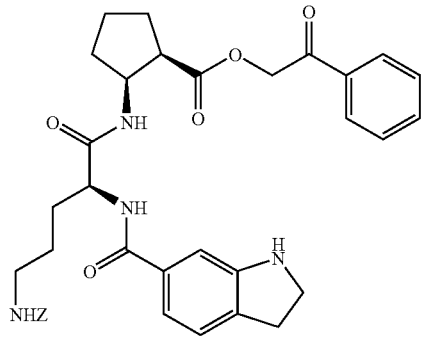
TABLE 41
223 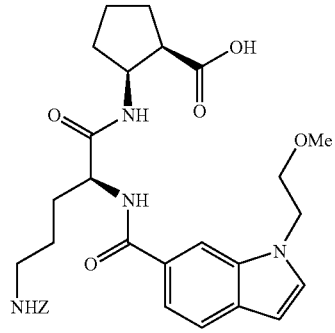
TABLE 41-continued
224 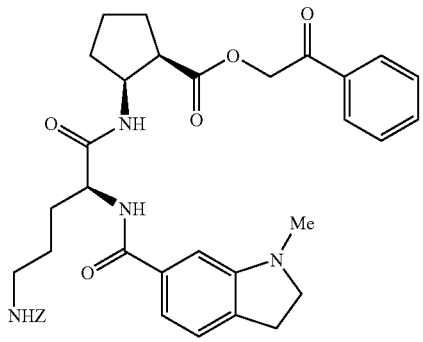
225 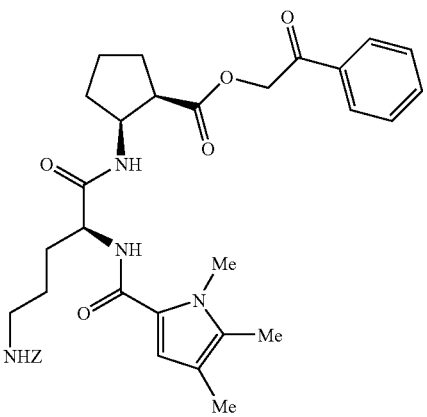
226 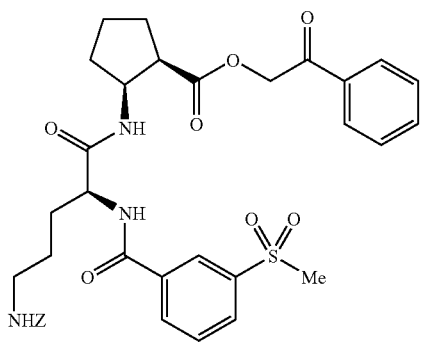
227 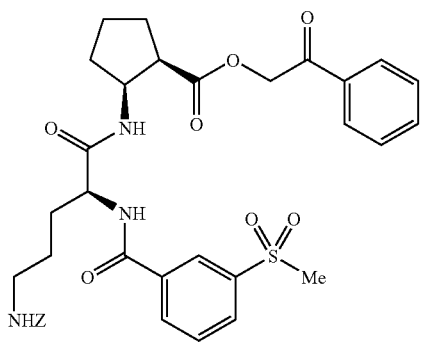

TABLE 41-continued
228 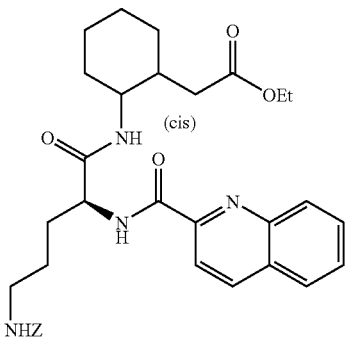
229 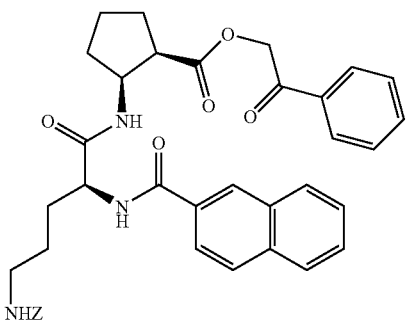
230 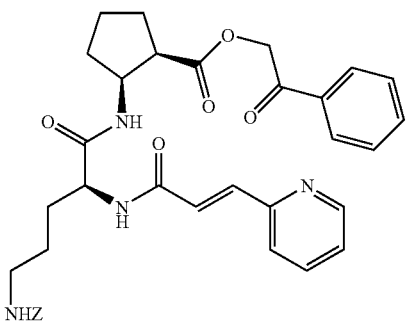
TABLE 42
231 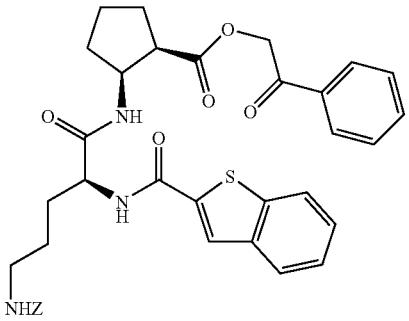
TABLE 42-continued
232 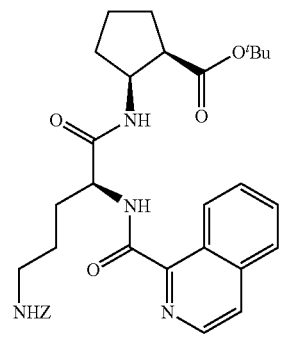
233 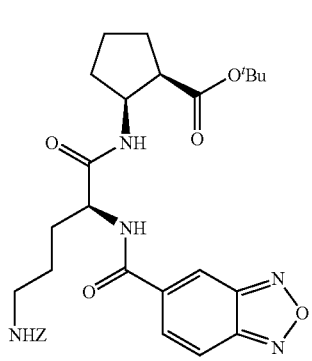
234 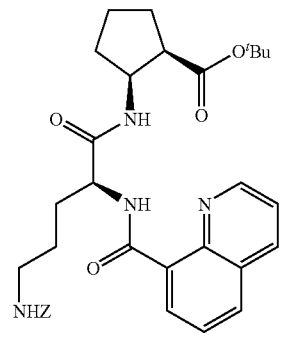
235 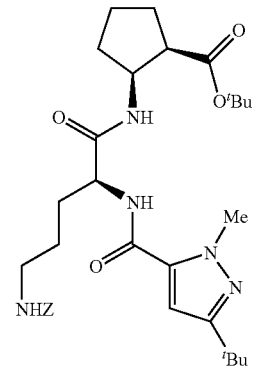

TABLE 42-continued
236 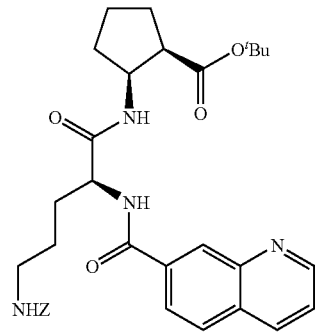
237 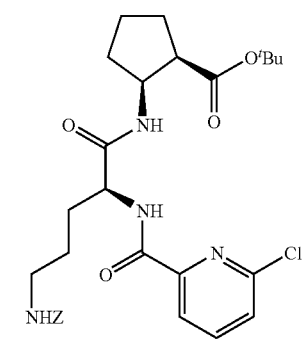
238 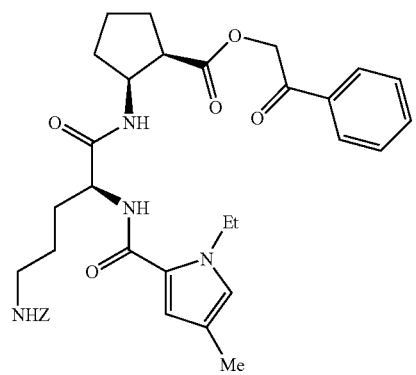
TABLE 43
239 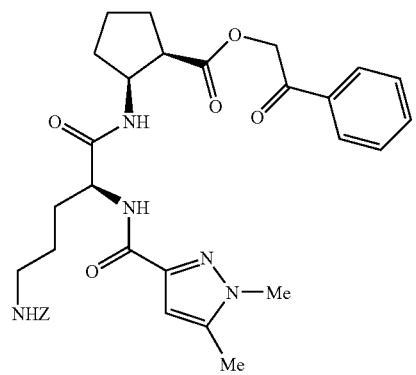
TABLE 43-continued
240 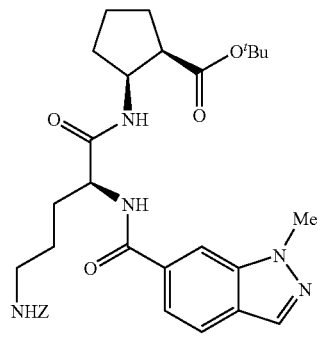
241 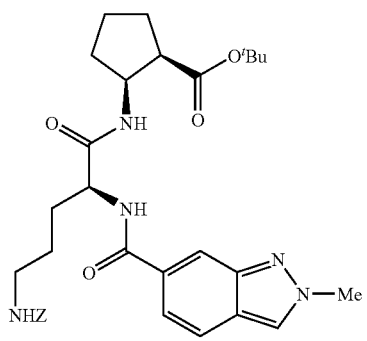
242 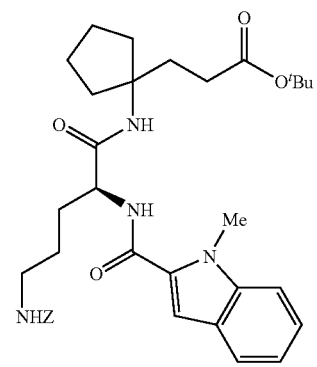
243 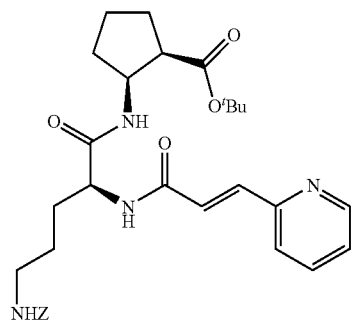

US 8,030,489 B2
TABLE 43-continued
244 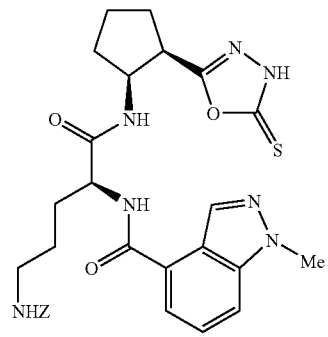
245 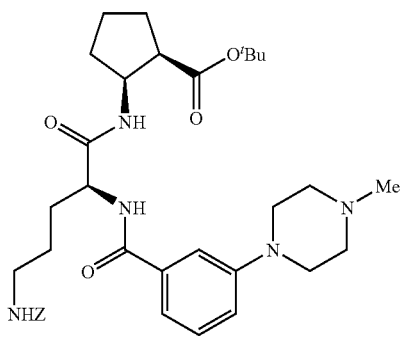
246 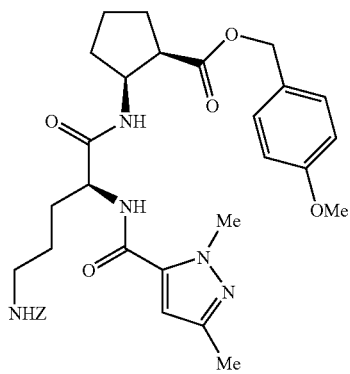
TABLE 44
247 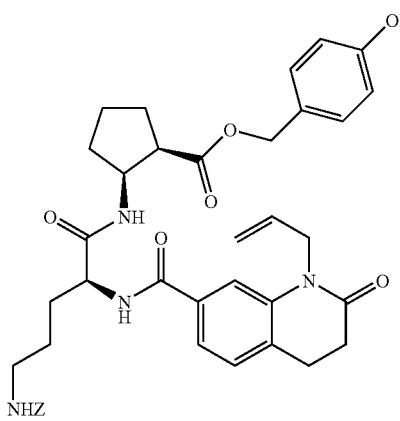
TABLE 44-continued
248 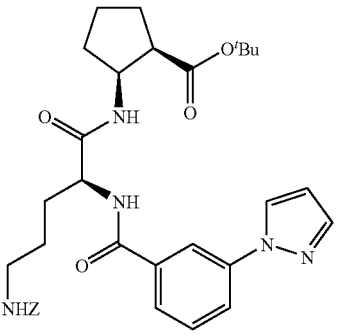
249 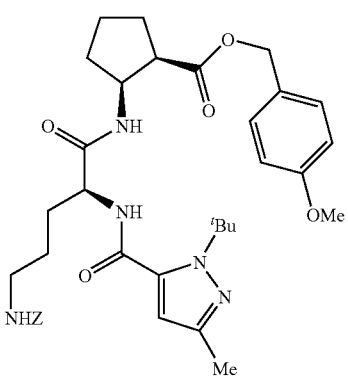
250 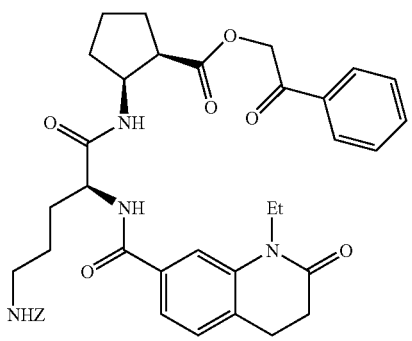
251 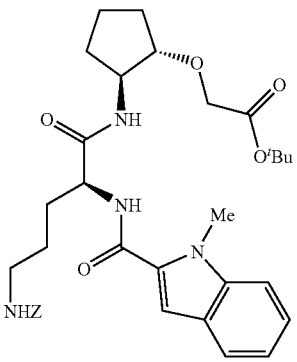

TABLE 44-continued
252 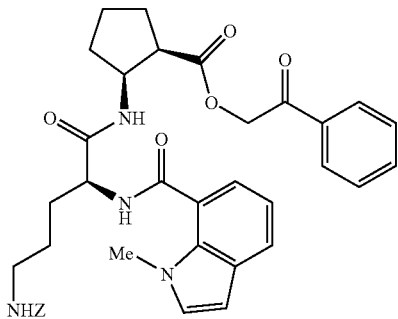
253 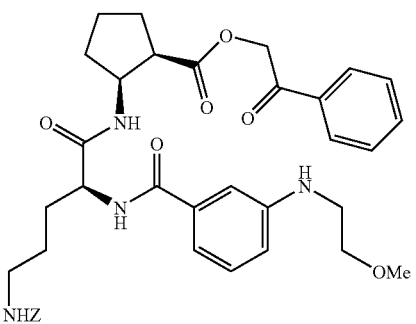
7 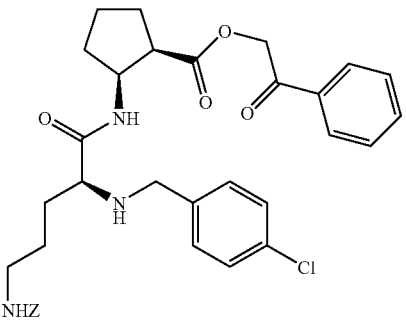
TABLE 45
254 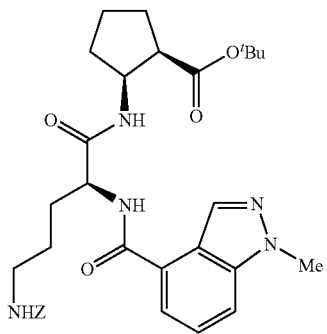
TABLE 45-continued
255 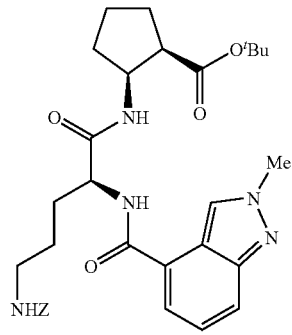
256 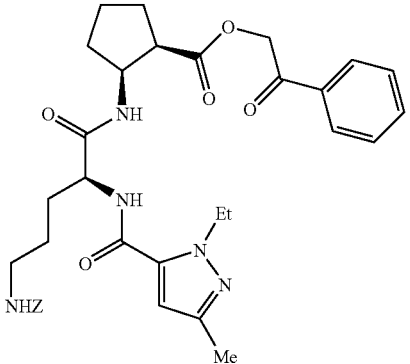
257 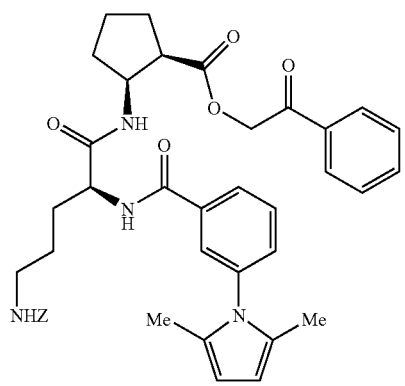
258 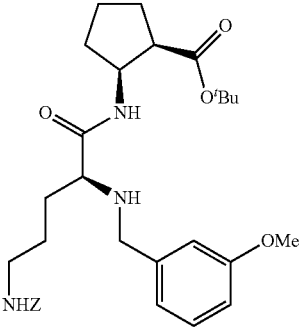

TABLE 45-continued
259 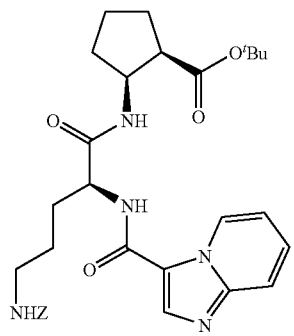
260 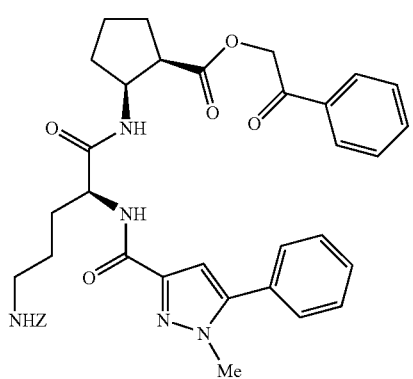
261 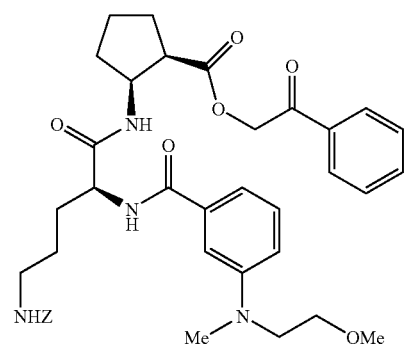
TABLE 46
262 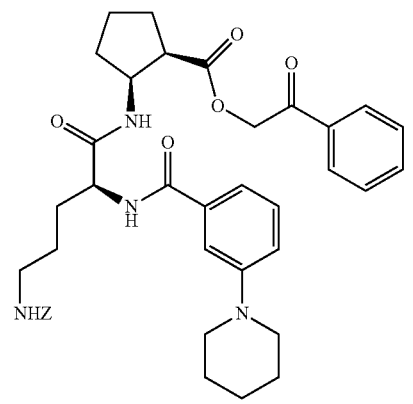
TABLE 46-continued
263 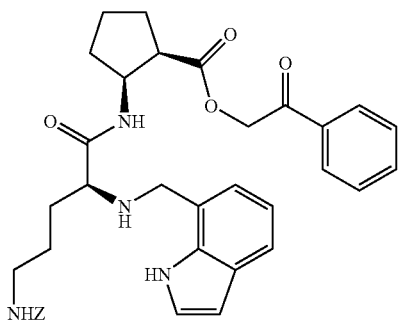
264 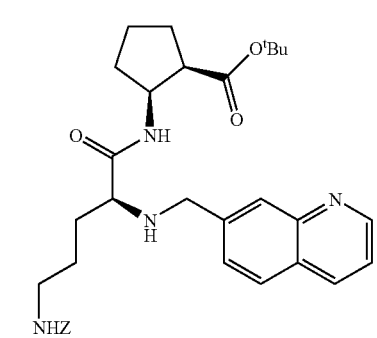
265 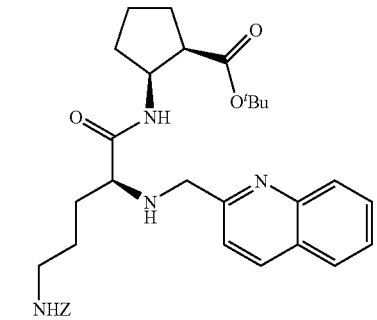
266 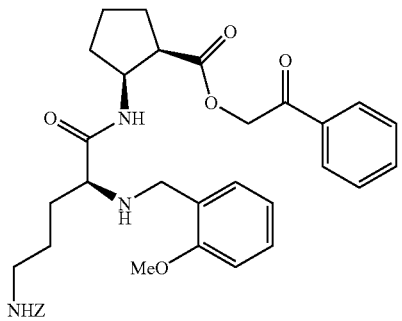

TABLE 46-continued
267 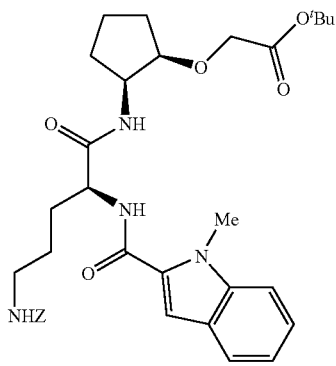
268 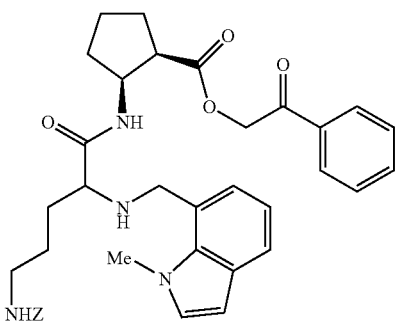
19 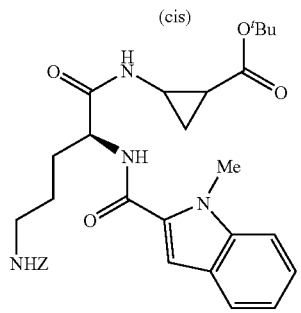
TABLE 47
20 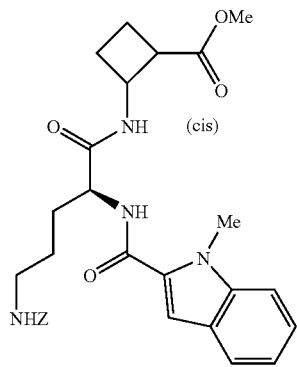
TABLE 47-continued
269 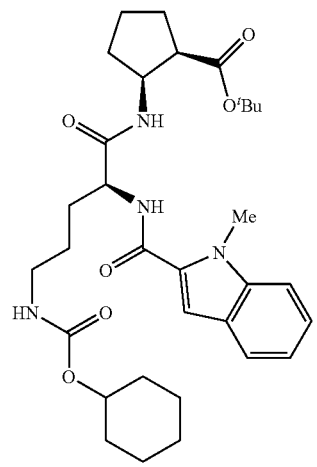
270 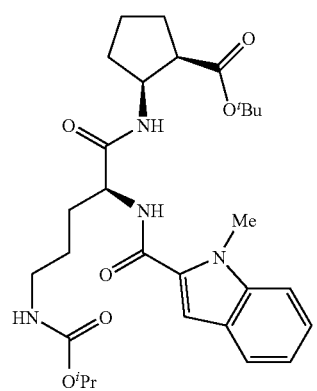
271 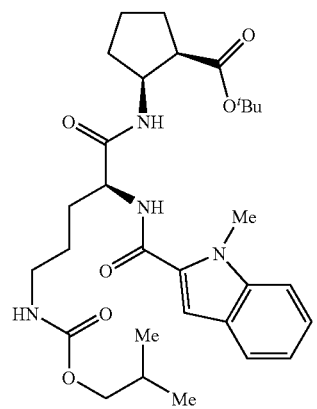

TABLE 47-continued
| 18 | 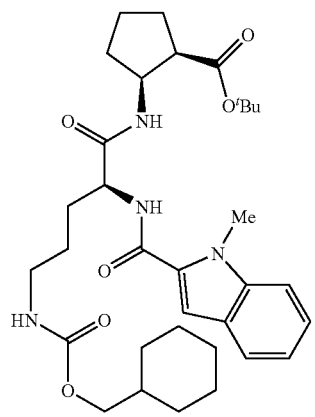 |
| 272 | 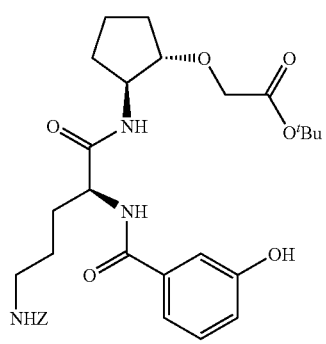 |
| 273 | 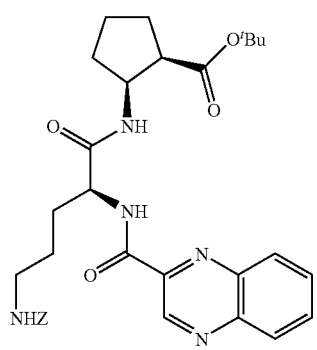 |
| 274 | 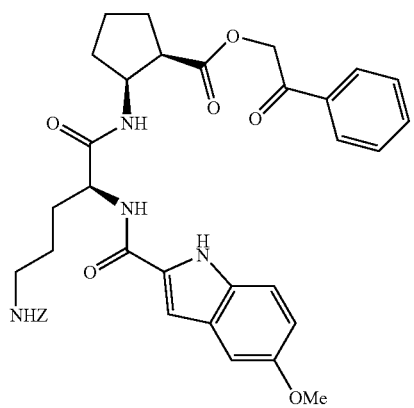 |
TABLE 48
| Ex | Str |
|---|---|
| 278 | 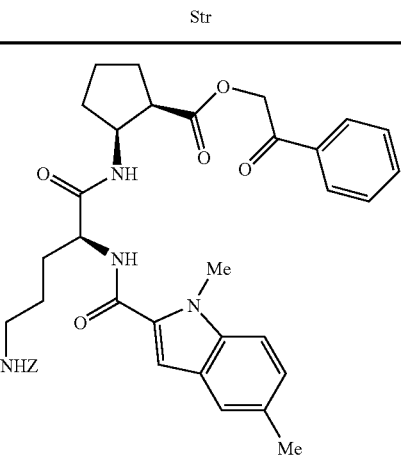 |
| 279 | 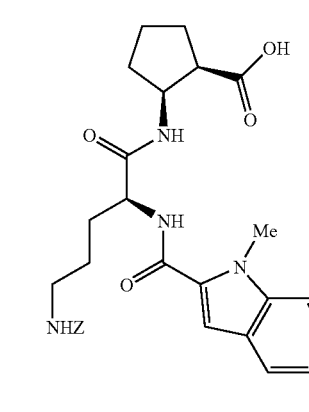 |
| 280 | 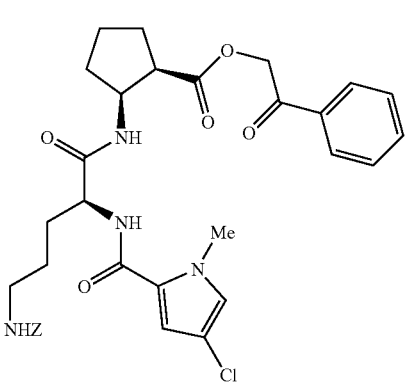 |
| 281 | 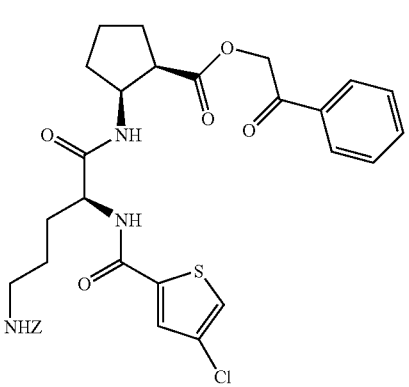 |

TABLE 48-continued

| Ex | Str |
|---|---|
| 282 | (structure: cyclopentane-carboxylic acid with NH linked to an amide-bearing chain containing NHZ and a 1-methyl-4-chloropyrrole-2-carbonyl group) |
| 283 | (structure: cyclopentane-carboxylic acid with NH linked to an amide-bearing chain containing NHZ and a 4-chlorothiophene-2-carbonyl group) |

TABLE 49

| Ex | Syn | Dat |
|---|---|---|
| 21 | B2 | ESI+: 563 |
| 2 | B1 | NMR1: 12.1-12.0 (1H, brs), 8.37 (1H, d, J = 8.3 Hz), 7.84 (1H, d, J = 8.4 Hz), 7.64 (1H, d, J = 7.9 Hz), 7.52 (1H, d, J = 8.4 Hz), 7.39-7.20 (7H, m), 7.19 (1H, s), 7.13-7.07 (1H, m), 5.01 (2H, s), 4.48-4.27 (2H, m), 3.95 (3H, s), 3.10-2.95 (2H, m), 2.90-2.80 (1H, m), 1.99-1.41 (10H, m); ESI+: 535 |
| 3 | B2 | ESI+: 535 |
| 22 | B2 | NMR1: 12.19 (1H, s), 8.45 (1H, d, J = 8.2 Hz), 7.69 (1H, d, J = 8.6 Hz), 7.64 (1H, d, J = 8.0 Hz), 7.52 (1H, d, J = 8.6 Hz), 7.39-7.20 (7H, m), 7.17 (1H, s), 7.14-7.07 (1H, m), 5.00 (2H, s), 4.50-4.40 (1H, m), 4.18-4.09 (1H, m), 3.95 (3H, s), 3.09-2.96 (2H, m), 2.63-2.56 (1H, m), 1.90-1.27 (12H, m); FAB+: 549 |
| 23 | B1 | NMR1: 12.1-11.9 (1H, brs), 8.75 (1H, d, J = 8.5 Hz), 8.59 (1H, d, J = 8.5 Hz), 8.21-8.13 (3H, m), 8.10 (1H, d, J = 8.1 Hz), 7.93-7.85 (1H, m), 7.78-7.70 (1H, m), 7.38-7.14 (6H, m), 4.98 (2H, s), 4.70-4.58 (1H, m), 4.46-4.33 (1H, m), 3.10-2.95 (2H, m), 2.93-2.83 (1H, m), 2.01-1.40 (10H, m); ESI+: 533 |
| 24 | B2 | ESI−: 519 |
| 9 | B3 | FAB+: 498 |
| 25 | B2 | NMR1: 12.1-11.9 (1H, brs), 8.23 (1H, d, J = 8.3 Hz), 8.06 (1H, s), 7.87 (1H, d, J = 8.3 Hz), 7.58 (2H, s), 7.47-7.45 (1H, m), 7.38-7.19 (6H, m), 6.47 (1H, d, J = 2.9 Hz), 5.00 (2H, s), 4.57-4.47 (1H, m), 4.40-4.29 (1H, m), 3.86 (3H, s), 3.10-2.95 (2H, m), 2.91-2.80 (1H, m), 1.99-1.40 (10H, m); FAB+: 535 |
| 26 | B2 | NMR1: 12.1-11.9 (1H, brs), 8.33 (1H, d, J = 8.2 Hz), 7.84 (1H, d, J = 8.4 Hz), 7.52-7.14 (9H, m), 7.13-7.04 (1H, m), 5.00 (2H, s), 4.53-4.39 (1H, m), 4.38-4.26 (1H, m), 3.81 (3H, s), 3.13-2.92 (2H, m), 2.90-2.77 (1H, m), 2.00-1.35 (10H, m); FAB+: 512 |
| 27 | B2 | ESI−: 549 |
| 28 | B2 | ESI+: 547 |
| 29 | B1 | FAB+: 563 |
| 30 | B2 | ESI−: 573 |
| 31 | B2 | NMR1: 12.0 (1H, s), 8.21 (1H, d, J = 8.2 Hz), 7.82 (1H, d, J = 8.3 Hz), 7.41-7.08 (9H, m), 6.90-6.80 (1H, m), 5.00 (2H, s), 4.52-4.39 (1H, m), 4.38-4.28 (1H, m), 3.11-2.78 (9H, m), 2.00-1.36 (10H, m); FAB+: 525 |
| 32 | B2 | NMR1: 12.0 (1H, s), 8.52 (1H, d, J = 8.2 Hz), 7.98-7.92 (1H, m), 7.90-7.80 (2H, m), 7.61 (1H, d, J = 9.2 Hz), 7.54-7.47 (1H, m), 7.40-7.17 (6H, m), 5.01 (2H, s), 4.50-4.40 (1H, m), 4.38-4.27 (1H, m), 3.09-2.93 (2H, m), 2.90-2.79 (1H, m), 2.00-1.38 (10H, m); FAB+: 516 |
| 33 | B2 | ESI+: 565 |
| 34 | B2 | FAB+: 553 |
| 35 | B2 | NMR1: 11.99 (1H, s), 8.65 (1H, s), 8.53 (1H, s), 8.00 (1H, d, J = 8.3 Hz), 7.86 (1H, d, J = 8.5 Hz), 7.40-7.27 (5H, m), 7.21-7.15 (1H, m), 5.00 (2H, s), 4.53-4.45 (1H, m), 4.40-4.30 (1H, m), 3.04-2.93 (2H, m), 2.88-2.80 (1H, m), 1.97-1.35 (10H, m); ESI−: 471 |
| 36 | B2 | NMR1: 11.99 (1H, s), 7.81 (1H, d, J = 8.4 Hz), 7.40-7.18 (7H, m), 5.65 (1H, s), 5.00 (2H, s), 4.44-4.29 (2H, m), 3.52 (3H, s), 3.05-2.95 (2H, m), 2.88-2.80 (1H, m), 2.14 (3H, s), 2.12 (3H, s), 1.96-1.40 (10H, m); ESI−: 511 |
| 37 | B2 | FAB+: 536 |

TABLE 50

| | | |
|---|---|---|
| 38 | B2 | NMR1: 12.02 (1H, s), 7.78 (1H, d, J = 8.3 Hz), 7.77 (1H, d, J = 8.3 Hz), 7.40-7.27 (5H, m), 7.23-7.16 (1H, m), 6.91-6.88 (1H, m), 6.86 (1H, dd, J = 1.6, 4.0 Hz), 6.00 (1H, dd, J = 2.8, 4.0 Hz), 5.00 (2H, s), 4.40-4.27 (2H, m), 3.80 (3H, s), 3.07-2.94 (2H, m), 2.88-2.78 (1H, m), 1.95-1.36 (10H, m); FAB+: 485 |
| 39 | B2 | NMR1: 12.07-11.96 (1H, brs), 8.58 (1H, d, J = 6.8 Hz), 8.38 (1H, s), 8.10-8.01 (2H, m), 7.63 (1H, d, J = 8.7 Hz), 7.40-7.16 (7H, m), 7.20-6.95 (1H, m), 4.99 (2H, s), 4.60-4.51 (1H, m), 4.42-4.32 (1H, m), 3.07-2.95 (2H, m), 2.90-2.82 (1H, m), 2.00-1.35 (10H, m); FAB+: 522 |
| 40 | B2 | ESI−: 510 |
| 41 | D1 | FAB+: 536 |
| 15 | B5 | Sal: HCl<br>FAB+: 513 |
| 42 | B2 | ESI−: 540 |
| 43 | B1 | NMR1: 12.30-11.70 (1H, br), 9.46 (1H, s), 8.92 (1H, d, J = 8.1 Hz), 8.43 (1H, d, J = 2.0 Hz), 8.34 (1H, d, J = 9.5 Hz), 8.25 (1H, d, J = 2.0 Hz), 8.03 (1H, d, J = 9.5 Hz), 7.98 (1H, d, J = 8.1 Hz), 7.38-7.24 (6H, m), 5.01 (2H, s), 4.58-4.47 (1H, m), 4.40-4.30 (1H, m), 3.10-2.97 (2H, m), 2.90-2.83 (1H, m), 1.98-1.43 (10H, m); ESI+: 522 |
| 44 | B2 | ESI+: 549 |
| 45 | B2 | ESI+: 549 |
| 46 | D1 | NMR1: 12.01 (1H, s), 8.18-8.13 (2H, m), 7.83 (1H, d, J = 8.4 Hz), 7.70 (1H, dd, J = 1.6, 8.7 Hz), 7.47 (1H, d, J = 8.7 Hz), 7.40 (1H, d, J = 3.1 Hz), 7.38-7.18 (6H, m), 6.53 (1H, d, J = 3.1 Hz), 5.00 (2H, s), 4.52-4.43 (1H, m), 4.38-4.28 (1H, m), 3.82 (3H, s), 3.08-2.97 (2H, m), 2.89-2.80 (1H, m), 1.99-1.41 (10H, m); ESI+: 535 |
| 47 | B2 | ESI+: 549 |
| 48 | B2 | ESI+: 549 |
| 49 | D1 | NMR1: 8.53-8.45 (2H, m), 8.10-8.00 (2H, m), 7.82-7.74 (1H, m), 7.40-7.18 (6H, m), 7.13 (1H, dd, J = 6.5, 9.2 Hz), 6.91-6.85 (1H, m), 4.99 (2H, s), 4.61-4.52 (1H, m), 4.42-4.30 (1H, m), 3.07-2.96 (2H, m), 2.90-2.80 (1H, m), 1.99-1.33 (10H, m); ESI−: 520 |
| 50 | D1 | NMR1: 12.02 (1H, s), 7.96 (1H, d, J = 8.4 Hz), 7.92 (1H, d, J = 8.4 Hz), 7.60 (1H, d, J = 8.1 Hz), 7.50 (1H, d, J = 7.3 Hz), 7.42 (1H, d, J = 3.1 Hz), 7.38-7.26 (6H, m), 7.24-7.18 (1H, m), 6.84 (1H, d, J = 3.1 Hz), 5.00 (2H, s), 4.60-4.50 (1H, m), 4.41-4.32 (1H, m), 3.83 (3H, s), 3.07-2.97 (2H, m), 2.90-2.82 (1H, m), 1.99-1.42 (10H, m); FAB+: 535 |
| 51 | B2 | ESI−: 547 |
| 52 | D1 | FAB+: 499 |
| 53 | B2 | ESI+: 524 |
| 54 | B2 | ESI+: 524 |
| 55 | B2 | ESI−: 522 |
| 56 | B1 | NMR1: 12.0-11.9 (1H, brs), 8.20 (1H, d, J = 8.3 Hz), 8.00 (1H, s), 7.87 (1H, d, J = 8.3 Hz), 7.60-7.55 (1H, m), 7.51 (1H, d, J = 8.3 Hz), 7.39-7.18 (7H, m), 5.00 (2H, s), 4.56-4.47 (1H, m), 4.40-4.29 (1H, m), 3.79 (3H, s), 3.10-2.96 (2H, m), 2.89-2.81 (1H, m), 2.26 (3H, s), 2.00-1.41 (10H, m); ESI+: 549 |

TABLE 51

| | | |
|---|---|---|
| 57 | B1 | NMR1: 12.0 (1H, s), 7.75 (1H, d, J = 8.4 Hz), 7.66 (1H, d, J = 8.4 Hz), 7.40-7.26 (5H, m), 7.24-7.16 (1H, m), 6.69-6.63 (2H, m), 5.01 (2H, s), 4.37-4.25 (2H, m), 3.73 (3H, s), 3.06-2.92 (2H, m), 288-2.78 (1H, m), 1.98 (3H, s), 1.95-1.34 (10H, m); ESI+: 499 |
| 58 | B2 | ESI−: 524 |
| 59 | B1 | ESI−: 549 |
| 60 | B1 | NMR1: 12.1-11.9 (1H, brs), 8.46 (1H, s), 8.34 (1H, d, J = 8.2 Hz), 8.19 (1H, d, J = 8.3 Hz), 8.14 (1H, s), 7.89 (1H, d, J = 8.3 Hz), 7.80-7.75 (1H, m), 7.39-7.18 (6H, m), 5.00 (2H, s), 4.57-4.47 (1H, m), 4.39-4.29 (1H, m), 3.93 (3H, s), 3.10-2.95 (2H, m), 2.90-2.80 (1H, m), 2.45 (3H, s), 2.00-1.41 (10H, m); ESI+: 577 |
| 61 | D1 | FAB+: 549 |
| 62 | D1 | FAB+: 547 |
| 63 | D1 | ESI−: 521 |
| 64 | D1 | FAB+: 579 |
| 65 | D1 | FAB+: 537 |
| 66 | D1 | ESI−: 531 |
| 4 | D1 | ESI+: 513 |
| 67 | D1 | FAB+: 560 |
| 68 | B2 | FAB+: 561 |
| 69 | D1 | FAB+: 532 |
| 11 | D3 | ESI−: 509 |
| 70 | D1 | FAB+: 538 |
| 71 | B1 | FAB+: 533 |
| 72 | B1 | FAB+: 524 |
| 73 | B1 | FAB+: 533 |
| 74 | B1 | ESI+: 542 |
| 75 | B1 | ESI+: 533 |
| 76 | B1 | NMR1: 12.10-11.92 (1H, brs), 8.39 (1H, d, J = 8.4 Hz), 8.12 (1H, d, J = 8.4 Hz), 8.09-8.00 (2H, m), 7.76 (1H, d, J = 7.7 Hz), 7.38-7.26 (5H, m), 7.21-7.15 (1H, m), 4.99 (2H, s), 4.60-4.51 (1H, m), 4.42-4.32 (1H, m), 3.06-2.95 (2H, m), 2.90-2.84 (1H, m), 1.98-1.35 (10H, m); FAB+: 517 |

TABLE 51-continued

| | | |
|---|---|---|
| 77 | D1 | ESI+: 513 |
| 78 | D1 | ESI+: 500 |
| 79 | B1 | ESI−: 534 |
| 80 | B1 | ESI−: 534 |
| 81 | B1 | ESI+: 563 |
| 13 | B4 | ESI−: 507 |
| 6 | F | Sal: 2HCl |
| | | FAB+: 519 |
| 82 | B1 | FAB+: 580 |

TABLE 52

| | | |
|---|---|---|
| 83 | A1 | NMR1: 16.0-15.7 (1H, brs), 8.21 (1H, d, J = 8.2 Hz), 7.75 (1H, d, J = 8.0 Hz), 7.63 (1H, d, J = 8.0 Hz), 7.51 (1H, d, J = 8.2 Hz), 7.39-7.23 (6H, m), 7.19-7.06 (3H, m), 5.00 (2H, s), 4.52-4.42 (1H, m), 4.29-4.18 (1H, m), 3.93 (3H, s), 3.66-3.56 (1H, m), 3.01-2.86 (2H, m), 2.15-1.89 (4H, m), 1.81-1.60 (2H, m), 1.41-1.13 (4H, m); ESI+: 559 |
| 5 | H | NMR1: 12.0 (1H, s), 8.24 (1H, d, J = 8.2 Hz), 7.83 (1H, d, J = 8.3 Hz), 7.41-7.26 (5H, m), 7.23-7.16 (1H, m), 6.72 (1H, s), 5.00 (2H, s), 4.44-4.25 (2H, m), 3.93 (3H, s), 3.08-2.91 (2H, m), 2.89-2.79 (1H, m), 2.15 (3H, s), 1.97-1.34 (10H, m); ESI+: 500 |
| 84 | C | ESI+: 557 |
| 85 | H | ESI+: 591 |
| 86 | B1 | FAB+: 548 |
| 87 | A1 | NMR1: 12.09-11.95 (1H, brs), 8.35 (1H, d, J = 8.3 Hz), 7.90 (1H, d, J = 8.3 Hz), 7.63 (1H, d, J = 7.8 Hz), 7.51 (1H, d, J = 8.3 Hz), 7.38-7.16 (8H, m), 7.13-7.07 (1H, m), 5.00 (2H, s), 4.54-4.46 (1H, m), 4.44-4.36 (1H, m), 3.95 (3H, s), 3.14-2.94 (3H, m), 2.06-1.38 (10H, m); FAB+: 575 |
| 88 | H | ESI+: 542 |
| 89 | C | ESI+: 537 |
| 90 | C | ESI+: 575 |
| 91 | D1 | ESI+: 579 |
| 92 | B1 | NMR1: 12.6-12.3 (1H, brs), 8.36 (1H, d, J = 8.1 Hz), 7.97 (1H, d, J = 7.3 Hz), 7.64 (1H, d, J = 7.9 Hz), 7.52 (1H, d, J = 8.3 Hz), 7.39-7.18 (8H, m), 7.14-7.07 (1H, m), 5.00 (2H, s), 4.45-4.32 (1H, m), 4.08 (2H, s), 4.01-3.97 (4H, m), 3.75-3.66 (1H, m), 3.10-2.95 (2H, m), 2.01-1.37 (10H, m); ESI+: 565 |
| 93 | D1 | NMR1: 12.0 (1H, s), 8.51 (1H, d, J = 8.2 Hz), 7.82 (1H, d, J = 8.3 Hz), 7.63 (1H, d, J = 7.8 Hz), 7.42-7.14 (8H, m), 7.08-6.99 (1H, m), 6.49 (1H, d, J = 2.9 Hz), 5.02 (2H, s), 4.51-4.42 (1H, m), 4.41-4.31 (1H, m), 3.71 (3H, s), 3.12-2.95 (2H, m), 2.92-2.81 (1H, m), 2.00-1.43 (10H, m); FAB+: 535 |
| 94 | D1 | FAB+: 555 |
| 8 | D2 | FAB+: 502 |
| 95 | B1 | ESI−: 534 |
| 96 | B1 | ESI−: 534 |
| 97 | D1 | ESI+: 514 |
| 98 | C | ESI+: 589 |
| 99 | C | ESI+: 577 |
| 100 | C | ESI−: 571 |
| 101 | D1 | FAB+: 575 |
| 102 | B7 | Sal: HCl |
| | | FAB+: 498 |
| 103 | C | ESI+: 575 |
| 104 | B1 | ESI+: 522 |
| 105 | C | ESI+: 591 |

TABLE 53

| | | |
|---|---|---|
| 106 | C | ESI+: 559 |
| 107 | C | ESI+: 559 |
| 108 | C | ESI+: 524 |
| 109 | A1 | NMR1: 14.30-13.90 (1H, br), 8.34 (1H, d, J = 8.2 Hz), 7.97 (1H, d, J = 8.2 Hz), 7.63 (1H, d, J = 7.9 Hz), 7.50 (1H, d, J = 8.2 Hz), 7.39-7.14 (8H, m), 7.12-7.06 (1H, m), 5.00 (2H, s), 4.57-4.47 (1H, m), 4.42-4.32 (1H, m), 3.95 (3H, s), 3.42-3.16 (1H, m), 3.10-2.92 (2H, m), 2.08-1.35 (10H, m); ESI−: 589 |
| 110 | D1 | ESI+: 562 |
| 111 | A1 | NMR1: 11.30-11.12 (1H, brs), 8.26 (1H, d, J = 8.2 Hz), 7.79 (1H, d, J = 8.8 Hz), 7.63 (1H, d, J = 8.2 Hz), 7.51 (1H, d, J = 8.2 Hz), 7.39-7.06 (9H, m), 5.00 (2H, s), 4.59-4.32 (2H, m), 3.94 (3H, s), 3.31-3.14 (1H, m), 3.08-2.90 (2H, m), 2.10-1.34 (10H, m); ESI−: 593 |
| 112 | C | ESI+: 575 |
| 113 | D1 | FAB+: 569 |
| 114 | D1 | FAB+: 565 |
| 115 | D1 | FAB+: 507 |
| 16 | B6 | Sal: fumarate |
| | | FAB+: 519 |

TABLE 53-continued

| | | |
|---|---|---|
| 116 | B6 | Sal: fumarate<br>ESI+: 519 |
| 117 | D4 | Sal: oxalate<br>FAB+: 498 |
| 118 | B1 | NMR1: 12.6-12.4 (1H, brs), 8.43 (1H, d, J = 8.2 Hz), 7.75 (1H, d, J = 7.8 Hz),<br>7.64 (1H, d, J = 8.0 Hz), 7.52 (1H, d, J = 8.5 Hz), 7.39-7.16 (8H, m), 7.14-7.07 (1H, m),<br>5.00 (2H, s), 4.53-4.41 (1H, m), 4.07-3.88 (6H, m), 3.82-3.75 (1H, m), 3.09-2.96 (2H,<br>m), 1.94-1.39 (10H, m); ESI+: 565 |
| 14 | D4 | Sal: oxalate<br>FAB+: 521 |
| 119 | A1 | NMR1: 14.27 (1H, s), 8.35 (1H, d, J = 8.3 Hz), 8.10 (1H, d, J = 7.8 Hz), 7.63 (1H, d,<br>J = 8.0 Hz), 7.50 (1H, d, J = 8.3 Hz), 7.37-7.14 (8H, m), 7.12-7.07 (1H, m), 5.00 (2H,<br>s), 4.46-4.34 (2H, m), 3.94 (3H, s), 3.44-3.35 (1H, m), 3.14-2.94 (2H, m),<br>2.06-1.82 (4H, m), 1.71-1.36 (6H, m); ESI−: 589 |
| 120 | A1 | NMR1: 13.45 (1H, s), 8.30 (1H, d, J = 8.6 Hz), 7.97 (1H, d, J = 8.6 Hz), 7.61 (1H, d,<br>J = 8.1 Hz), 7.49 (1H, d, J = 8.1 Hz), 7.38-7.12 (8H, m), 7.11-7.06 (1H, m), 5.01 (2H,<br>s), 4.64-4.54 (1H, m), 4.35-4.25 (1H, m), 3.94 (3H, s), 3.44 (3H, s), 3.36-3.27 (1H,<br>m), 3.10-2.90 (2H, m), 2.23-2.02 (4H, m), 1.70-1.22 (6H, m): FAB+: 604 |
| 121 | A1 | NMR1: 12.55 (1H, s), 8.32 (1H, d, J = 8.2 Hz), 7.81 (1H, d, J = 8.6 Hz), 7.63 (1H, d,<br>J = 7.9 Hz), 7.51 (1H, d, J = 8.6 Hz), 7.39-7.14 (8H, m), 7.13-7.06 (1H, m), 5.01 (2H,<br>s), 4.60-4.50 (1H, m), 4.42-4.32 (1H, m), 3.95 (3H, s), 3.14-2.92 (3H, m),<br>2.22-1.80 (4H, m), 1.70-1.36 (6H, m); FAB+: 591 |
| 122 | C | ESI+: 538 |
| 123 | C | FAB+: 523 |
| 124 | C | ESI−: 539 |
| 125 | C | ESI+: 523 |

TABLE 54

| | | |
|---|---|---|
| 126 | C | ESI+: 566 |
| 127 | C | ESI+: 537 |
| 128 | C | ESI+: 536 |
| 129 | C | ESI+: 522 |
| 130 | C | ESI+: 557 |
| 131 | C | ESI+: 557 |
| 132 | C | FAB+: 607 |
| 133 | C | FAB+: 555 |
| 134 | C | FAB+: 559 |
| 135 | C | FAB+: 559 |
| 136 | C | FAB+: 540 |
| 137 | C | ESI+: 559 |
| 138 | C | FAB+: 549 |
| 139 | C | ESI−: 589 |
| 140 | C | FAB+: 539 |
| 141 | C | ESI−: 571 |
| 142 | C | ESI−: 587 |
| 143 | C | ESI−: 587 |
| 144 | C | FAB+: 553 |
| 145 | C | ESI+: 560 |
| 146 | C | ESI+: 560 |
| 147 | C | ESI+: 572 |
| 148 | C | FAB+: 546 |
| 149 | C | FAB+: 578 |
| 17 | A2 | ESI+: 589 |
| 150 | C | FAB+: 589 |
| 151 | C | FAB+: 619 |
| 152 | B1 | ESI+: 507 |
| 153 | C | ESI−: 567 |
| 154 | C | ESI−: 576 |
| 12 | S | ESI+: 521 |
| 155 | S | ESI+: 521 |
| 156 | C | FAB+: 592 |
| 157 | B1 | ESI+: 527 |

TABLE 55

| | | |
|---|---|---|
| 158 | B1 | ESI+: 487 |
| 159 | B1 | NMR1: 12.1-11.9 (1H, brs), 8.37 (1H, d, J = 8.3 Hz), 7.84 (1H, d, J = 8.4 Hz),<br>7.64 (1H, d, J = 7.9 Hz), 7.52 (1H, d, J = 8.5 Hz), 7.31-7.24 (1H, m), 7.19 (1H, s),<br>7.13-7.02 (2H, m), 4.48-4.28 (2H, m), 3.96 (3H, s), 3.71 (2H, d, J = 6.8 Hz),<br>3.07-2.91 (2H, m), 2.90-2.79 (1H, m), 1.98-1.39 (11H, m), 0.86 (6H, d, J = 6.7 Hz);<br>ESI+: 501 |
| 160 | B1 | NMR1: 12.1-11.9 (1H, brs), 8.36 (1H, d, J = 8.2 Hz), 7.84 (1H, d, J = 8.2 Hz),<br>7.64 (1H, d, J = 7.9 Hz), 7.52 (1H, d, J = 8.4 Hz), 7.31-7.24 (1H, m), 7.18 (1H, s),<br>7.13-7.07 (1H, m), 7.06-6.98 (1H, m), 4.48-4.27 (2H, m), 3.96 (3H, s), 3.74 (2H, d, J = 6.5 Hz),<br>3.07-2.91 (2H, m), 2.90-2.79 (1H, m), 2.00-1.37 (16H, m), 1.27-1.04 (3H,<br>m), 0.99-0.82 (2H, m); ESI+: 541 |
| 161 | B1 | ESI+: 528 |
| 162 | C, B1 | ESI+: 563 |
| 163 | C | FAB+: 603 |
| 164 | C | NMR1: 16.0-15.7 (1H, brs), 11.4 (1H, d, J = 1.5 Hz), 8.14 (1H, d, J = 8.3 Hz),<br>7.82 (1H, d, J = 8.0 Hz), 7.44-7.23 (6H, m), 7.19-7.01 (3H, m), 6.83 (1H, dd, J = 8.9, 2.4 Hz),<br>5.01 (2H, s), 4.54-4.42 (1H, m), 4.36-4.23 (1H, m), 3.75 (3H, s), 3.65-3.54 (1H,<br>m), 3.01-2.82 (2H, m), 2.17-1.89 (4H, m), 1.81-1.58 (2H, m), 1.38-1.11 (4H, m);<br>FAB+: 575 |
| 165 | D1 | NMR1: 12.0 (1H, s), 11.4 (1H, s), 8.30 (1H, d, J = 8.3 Hz), 7.89 (1H, d, J = 8.3 Hz),<br>7.42-7.02 (9H, m), 6.84 (1H, dd, J = 8.9, 2.4 Hz), 5.00 (2H, s), 4.56-4.43 (1H, m),<br>4.41-4.28 (1H, m), 3.76 (3H, s), 3.13-2.93 (2H, m), 2.91-2.78 (1H, m),<br>2.00-1.37 (10H, m); FAB+: 551 |
| 166 | C | FAB+: 576 |
| 167 | C | ESI−: 590 |
| 168 | C | ESI−: 558 |

TABLE 55-continued

| | | |
|---|---|---|
| 169 | C | NMR1: 16.0-15.7 (1H, brs), 8.15 (1H, d, J = 8.2 Hz), 7.75 (1H, d, J = 7.9 Hz), 7.46-7.23 (6H, m), 7.20-6.86 (4H, m), 5.01 (2H, s), 4.52-4.41 (1H, m), 4.28-4.17 (1H, m), 3.89 (3H, s), 3.77 (3H, s), 3.65-3.55 (1H, m), 3.01-2.83 (2H, m), 2.16-1.58 (6H, m), 1.45-1.10 (4H, m); ESI+: 589 |
| 170 | D1 | NMR1: 12.0 (1H, s), 8.31 (1H, d, J = 8.3 Hz), 7.84 (1H, d, J = 8.3 Hz), 7.43 (1H, d, J = 9.0 Hz), 7.38-7.17 (6H, m), 7.15-7.05 (2H, m), 6.92 (1H, dd, J = 9.0, 2.4 Hz), 5.01 (2H, s), 4.51-4.26 (2H, m), 3.92 (3H, s), 3.77 (3H, s), 3.13-2.94 (2H, m), 2.91-2.77 (1H, m), 1.97-1.40 (10H, m); ESI−: 563 |
| 171 | D1 | ESI+: 539 |
| 172 | D1 | FAB+: 555 |
| 173 | B1 | ESI+: 534 |
| 174 | C | ESI+: 577 |
| 175 | C | FAB+: 559 |
| 176 | A1 | NMR1: 11.9-11.4 (1H, brs), 8.33 (1H, d, J = 8.4 Hz), 7.83 (1H, d, J = 8.0 Hz), 7.64 (1H, d, J = 7.9 Hz), 7.52 (1H, d, J = 8.4 Hz), 7.41-7.03 (9H, m), 5.00 (2H, s), 4.75-4.60 (1H, brs), 4.50-4.35 (2H, m), 3.95 (3H, s), 3.55-3.40 (2H, m), 3.31-3.19 (1H, m), 3.11-2.95 (2H, m), 2.93-2.80 (1H, m), 2.04-1.37 (13H, m); FAB+: 656 |

TABLE 56

| | | |
|---|---|---|
| 177 | A1 | ESI+: 577 |
| 1 | A1 | ESI+: 591 |
| 178 | A1 | ESI+: 549 |
| 179 | A1 | ESI+: 563 |
| 180 | C | ESI+: 589 |
| 181 | C | FAB+: 535 |
| 182 | C | FAB+: 554 |
| 183 | C | FAB+: 549 |
| 184 | C | ESI−: 524 |
| 185 | C | FAB+: 565 |
| 186 | C | ESI+: 561 |
| 187 | C | ESI+: 619 |
| 188 | C | ESI+: 589 |
| 189 | C | FAB+: 539 |
| 190 | C | FAB+: 530 |
| 191 | C | FAB+: 579 |
| 192 | C | ESI+: 567 |
| 193 | C | ESI+: 487 |
| 194 | C | ESI+: 527 |
| 195 | C | ESI+: 550 |
| 196 | C | ESI+: 499 |
| 197 | C | ESI+: 536 |
| 198 | C | FAB+: 526 |
| 199 | C | FAB+: 654 |
| 200 | C | FAB+: 527 |
| 201 | C | FAB+: 640 |
| 10 | I | FAB+: 556 |
| 202 | C | ESI+: 578 |
| 203 | A1 | ESI+: 577 |
| 204 | A1 | ESI+: 563 |
| 205 | C | ESI+: 653 |
| 206 | A1 | ESI+: 563 |
| 207 | A1 | ESI+: 563 |
| 208 | C | ESI+: 640 |
| 209 | C | ESI+: 653 |

TABLE 57

| | | |
|---|---|---|
| 210 | C | ESI+: 563 |
| 211 | C | ESI+: 617 |
| 212 | C | FAB+: 538 |
| 213 | C | FAB+: 538 |
| 214 | C | FAB+: 538 |
| 215 | C | ESI+: 605 |
| 216 | C | ESI+: 555 |
| 217 | C | FAB+: 540 |
| 218 | C | FAB+: 607 |
| 219 | C | ESI+: 633 |
| 220 | C | ESI+: 667 |
| 221 | C | ESI+: 665 |
| 222 | B8 | ESI+: 641 |
| 223 | C | ESI+: 697 |
| 224 | C | ESI+: 655 |
| 225 | C | ESI+: 651 |
| 226 | C | ESI+: 631 |
| 227 | C | ESI+: 678 |

TABLE 57-continued

| | | |
|---|---|---|
| 228 | A1 | ESI+: 589 |
| 229 | C | FAB+: 650 |
| 230 | C | FAB+: 627 |
| 231 | C | ESI−: 654 |
| 232 | C | ESI+: 589 |
| 233 | C | ESI+: 580 |
| 234 | C | ESI+: 589 |
| 235 | C | ESI+: 598 |
| 236 | C | ESI+: 589 |
| 237 | C | ESI+: 573 |
| 238 | C | ESI+: 631 |
| 239 | C | ESI+: 618 |
| 240 | C | ESI+: 592 |
| 241 | C | ESI+: 592 |
| 242 | A1 | ESI+: 619 |
| 243 | C | FAB+: 565 |
| 244 | C | FAB+: 592 |

TABLE 58

| | | |
|---|---|---|
| 245 | C | ESI+: 636 |
| 246 | C | ESI+: 620 |
| 247 | C | ESI+: 711 |
| 248 | C | ESI+: 604 |
| 249 | C | ESI+: 662 |
| 250 | C | ESI+: 697 |
| 251 | A1 | ESI+: 621 |
| 252 | C | FAB+: 653 |
| 253 | C | FAB+: 673 |
| 7 | G | ESI+: 620 |
| 254 | C | ESI+: 592 |
| 255 | C | ESI+: 592 |
| 256 | C | ESI+: 632 |
| 257 | C | ESI−: 691 |
| 258 | G | FAB+: 554 |
| 259 | C | ESI+: 578 |
| 260 | C | ESI+: 680 |
| 261 | C | FAB+: 687 |
| 262 | C | FAB+: 683 |
| 263 | G | FAB+: 625 |
| 264 | G | FAB+: 575 |
| 265 | G | FAB+: 575 |
| 266 | G | FAB+: 616 |
| 267 | A1 | ESI+: 621 |
| 268 | G | FAB+: 639 |
| 19 | A4 | ESI+: 563 |
| 20 | A3 | ESI+: 535 |
| 269 | E | ESI+: 583 |
| 270 | E | ESI+: 543 |
| 271 | E | ESI+: 557 |
| 18 | E | ESI+: 597 |
| 272 | C | FAB+: 584 |
| 273 | C | ESI+: 590 |
| 274 | C | FAB+: 669 |
| 275 | C | FAB+: 683 |

TABLE 59

| | | |
|---|---|---|
| 276 | C | ESI−: 655 |
| 277 | C | FAB+: 673 |
| 278 | A1 | FAB+: 667 |
| 279 | D1 | NMR1: 12.0 (1H, s), 8.32 (1H, d, J = 8.3 Hz), 7.83 (1H, d, J = 8.3 Hz), 7.45-7.18 (8H, m), 7.13-7.07 (2H, m), 5.01 (2H, s), 4.49-4.27 (2H, m), 3.92 (3H, s), 3.09-2.80 (3H, m), 2.39 (3H, s), 1.98-1.39 (10H, m); FAB+: 549 |
| 280 | A1 | ESI+: 637 |
| 281 | A1 | ESI+: 640 |
| 282 | D1 | NMR1: 12.1-12.0 (1H, brs), 7.93 (1H, d, J = 8.0 Hz), 7.77 (1H, d, J = 8.7 Hz), 7.40-7.27 (5H, m), 7.22-7.16 (1H, m), 7.07 (1H, d, J = 2.0 Hz), 6.93 (1H, d, J = 2.0 Hz), 5.00 (2H, s), 4.38-4.25 (2H, m), 3.77 (3H, s), 3.07-2.90 (2H, m), 2.88-2.78 (1H, m), 1.96-1.33 (10H, m); ESI+: 519 |
| 283 | D1 | NMR1: 12.0-11.9 (1H, brs), 8.53 (1H, d, J = 8.0 Hz), 7.90 (1H, d, J = 10.0 Hz), 7.80 (1H, d, J = 4.6 Hz), 7.41-7.25 (5H, m), 7.24-7.14 (2H, m), 5.01 (2H, s), 4.44-4.28 (2H, m), 3.07-2.92 (2H, m), 2.89-2.80 (1H, m), 1.96-1.36 (10H, m); ESI+: 522 |

[Sequence List Free Text]

The following sequence numeral list <400> has a description of base sequences of a rat EP4 (sequence number 1).

SEQUENCE LISTING

<160> NUMBER OF SEQ ID NOS: 1

<210> SEQ ID NO 1
<211> LENGTH: 1501
<212> TYPE: DNA
<213> ORGANISM: Rattus sp.

<400> SEQUENCE: 1

```
aagctgtgta ctactgacca ccatcatgtc catccccgga gtcaacgcgt ccttctcctc    60
cactccggag aggttgaaca gcccagtgac cattcccgca gtgatgttta tcttcggggt   120
ggtgggcaac ctggtggcca tcgtagtatt gtgcaagtcg cgcaaggagc agaaggagac   180 tacctttac actctggtat gtgggctggc tgtcactgac ctactgggca cattgttggt   240
aagcccagtg accatcgcca catacatgaa gggccagtgg cccggagacc aggcattgtg   300
tgactacagc accttcatcc tacttttctt cggcctgtcg ggtctcagca tcatctgtgc   360
catgagcatt gagcgctacc tggccatcaa ccacgcctac ttctacagcc actacgtgga   420
caagcggctg gccggtctca cgctcttcgc cgtctatgca tctaacgtgc tcttctgcgc   480
actgcccaac atgggcctgg gtaggtccga gcggcagtac ccggggacct ggtgcttcat   540
cgactggacc accaacgtaa cggcctacgc cgccttctct tacatgtacg cgggcttcag   600
ttccttcctc atcctcgcca ccgtgctctg caatgtgctg gtgtgcggcg cgctgctccg   660
catgctccgc cagttcatgc gccgcacctc gctgggcacg gagcagcacc acgcggccgc   720
tgcagcagcg gtggcttcgg tggcctgtcg gggtcacgcg gccgcctccc cagccctgca   780
gcgcctcagt gactttcgcc gccgcaggag cttccggcgc atcgcgggtg cagagatcca   840
gatggtcatc ttactcatcg ccacctctct ggtggtgctc atctgctcca ttccgctcgt   900
ggtgcgagtg ttcatcaacc agttatatca gccaagtgtg gtgaaagaca tcagcagaaa   960
cccggatttg caggccatca gaattgcttc tgtgaacccc atcctggacc cttggatcta  1020
catccttctt cggaagactg tgctcagtaa agccatagaa aagatcaagt gcctcttctg  1080
ccgcattggt ggttctggca gagacggttc agcacagcac tgctcagaga gtcggaggac  1140
atcttctgcc atgtctggcc actcccgctc cttcctctcg cggagttgaa gggagatcag  1200
cagcacctct cacaccctcc tataccctgcc agacctaact gaaagcagcc tcggaggcaa  1260
```

| | |
|---|---|
| gaatttgctt ccaggtacgc atggcatggg cctgacccaa gcagacacca cctcgctgag | 1320 |
| aactttgcga atttcagaga cctcagactc ctcccagggc caggactctg agagtgtctt | 1380 |
| gttggtggat gaggttagtg ggagccagag agaggagcct gcctctaagg ggaactctct | 1440 |
| gcaagtcacg ttccccagtg aaacgctgaa attatctgaa aaatgtatat agtagcttaa | 1500 |
| a | 1501 |

The invention claimed is:

1. A compound of the formula (I) or a pharmaceutically acceptable salt thereof:

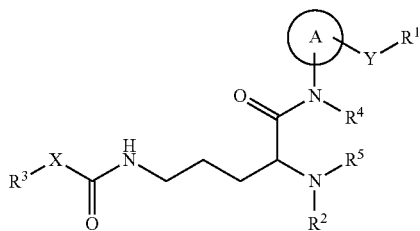

wherein:
A represents cycloalkanediyl,
X represents a single bond, —O—, —NH—, or —NR$^0$—,
Y represents a single bond, —R$^{00}$—, or —Y$^1$—R$^{00}$—,
Y$^1$ represents —O—, —S—, —S(O)—, —S(O)$_2$—, or —NHS(O)$_2$—,
R$^1$ represents —CO$_2$H, —CO$_2$—(C$_{1-4}$ alkyl), —CO—NH—SO$_2$—(C$_{1-4}$ alkylene)-OH, or tetrazol-5-yl,
R$^2$ represents —R$^0$, —C(O)—R$^0$, —R$^{21}$, or —C(O)—R$^{21}$,
R$^{21}$ represents phenyl, pyridyl, pyrrolyl, pyrazolyl, indolyl, imidazopyridyl, quinolyl, benzofuryl, or -(lower alkenylene)-(phenyl), each of which may be substituted with a member selected from the group consisting of —R$^0$, —OH, —OR$^0$, halogen, acetyl, and —N(R$^0$)$_2$,
R$^3$ represents —R$^0$, -(aryl which may be substituted), -(cycloalkyl which may be substituted), —R$^{00}$-(aryl which may be substituted), or —R$^{00}$-(cycloalkyl which may be substituted), wherein the substituent, if present, is a member selected from the group consisting of —R$^0$, —R$^{00}$—OH, —R$^{00}$—OR$^0$, —OH, —OR$^0$, —O—R$^{00}$—OH, —O—R$^{00}$—O-(hetero ring), —O—C(O)—R$^{00}$, halogen, oxo, —NR$^0{}_2$, —NH—SO$_2$—R$^0$, —NR$^0$—CO—R$^0$, —NH—R$^{00}$—OR$^0$, —NR$^0$—R$^{00}$—OR$^0$, —CO—R$^0$, —SO$_2$—R$^0$, -(lower alkenyl), phenyl, pyrrolidinyl, pyrrolyl which may be substituted with a lower alkyl group, pyrazolyl, piperidinyl, and piperazinyl,
R$^4$ and R$^5$ each represent H or R$^0$,
R$^0$ represents lower alkyl, and
R$^{00}$ represents lower alkylene.

2. The compound or a pharmaceutically acceptable salt thereof as described in claim 1, wherein
A is cyclopentane-1,2-diyl or cyclohexane-1,2-diyl,
X is —O—, and
R$^2$ is —C(O)—R$^{21}$, and
R$_3$ is —R$^0$, —R$^{00}$-(aryl which may be substituted), or —R$^{00}$-(cycloalkyl which may be substituted).

3. The compound or a pharmaceutically acceptable salt thereof as described in claim 2, wherein
A is cyclopentane-1,2-diyl, and
R$^{21}$ is phenyl, pyrrolyl, indolyl, quinolyl, or -(lower alkenylene)-(phenyl), each of which may be substituted with a group selected from —R$^0$, —OH, halogen, acetyl, and —N(R$^0$)$_2$, and
R$^3$ is benzyl.

4. A compound selected from:
(1R,2S)-2-({N$^5$-[(benzyloxy)carbonyl]-N$^2$-(quinolin-2-ylcarbonyl)-L-ornithyl}amino)cyclopentanecarboxylic acid,
(1R,2S)-2-({N$^5$-[(benzyloxy)carbonyl]-N$^2$-[(1-methyl-1H-indol-6-yl) carbonyl]-L-ornithyl}amino)cyclopentanecarboxylic acid,
(1R,2S)-2-({N$^5$-[(benzyloxy)carbonyl]-N$^2$-[3-(dimethylamino)benzoyl]-L-ornithyl}amino)cyclopentanecarboxylic acid,
(1R,2S)-2-({N$^5$-[(benzyloxy)carbonyl]-N$^2$-(3-chlorobenzoyl)-L-ornithyl}amino)cyclopentanecarboxylic acid,
(1R,2S)-2-({N$^5$-[(benzyloxy)carbonyl]-N$^2$-[(1-methyl-1H-indol-4-yl)carbonyl]-L-ornithyl }amino)cyclopentanecarboxylic acid,
(1R,2S)-2-({N$^5$-[(benzyloxy)carbonyl]-N$^2$-[(2E)-3-(2-hydroxyphenyl)prop-2-enoyl]-L-ornithyl}amino)cyclopentanecarboxylic acid,
(1R,2S)-2-({N$^5$-[(benzyloxy)carbonyl]-N$^2$-[(1,4-dimethyl-1H-pyrrol-2-yl)carbonyl]-L-ornithyl }amino)cyclopentanecarboxylic acid,
(1R,2S)-2-({N$^2$-[(3-acetyl-1-methyl-1H-indol-6-yl)carbonyl]-N$^5$-[(benzyloxy)carbonyl]-L-ornithyl }amino)cyclopentanecarboxylic acid, and
(1R,2S)-2-({N$^5$-[(benzyloxy)carbonyl]-N$^2$-[(1-methyl-1H-indol-7-yl)carbonyl]-L-ornithyl}amino)cyclopentanecarboxylic acid;
or a pharmaceutically acceptable salt thereof.

5. A pharmaceutical composition comprising the compound or a pharmaceutically acceptable salt thereof as described in claim 1, and a pharmaceutically acceptable excipient.

* * * * *